(12) United States Patent
Cianfriglia et al.

(10) Patent No.: US 8,822,648 B2
(45) Date of Patent: Sep. 2, 2014

(54) ANTIBODY DERIVATIVES

(71) Applicants: Instituto Superiore di Sanita, Rome (IT); Diatheva s.r.l., Fano (IT)

(72) Inventors: Maurizio Cianfriglia, Rome (IT); Michela Flego, Rome (IT); Alessandro Ascione, Rome (IT); Valentina Fiori, Fano (IT); Sabrina Domicini, Fano (IT); Alessandra Mallano, Rome (IT); Diego Moricoli, Fano (IT); Silvia Zamboni, Rome (IT)

(73) Assignees: Instituto Superiore di Sanita, Rome (IT); Diatheva s.r.l., Fano (IT)

( * ) Notice: Subject to any disclaimer, the term of this patent is extended or adjusted under 35 U.S.C. 154(b) by 0 days.

(21) Appl. No.: 13/725,712

(22) Filed: Dec. 21, 2012

(65) Prior Publication Data

US 2013/0203964 A1    Aug. 8, 2013

Related U.S. Application Data

(63) Continuation of application No. PCT/EP2011/003444, filed on Jun. 21, 2011.

(51) Int. Cl.
*C07K 19/00* (2006.01)
*C07K 16/30* (2006.01)

(52) U.S. Cl.
USPC ............... 530/387.3; 530/388.8; 530/388.85

(58) Field of Classification Search
None
See application file for complete search history.

(56) References Cited

PUBLICATIONS

Pavoni et al., BMC Cancer 2006: 6:41, pp. 1-15.*
Asano et al., J. Biochem 2002: 132: 903-09.*
Jantscheff et al., J Leukocyte Biol. 1996; 59:891-901.*
Viti et al., Methods Enzymol 2000; 326:480-505.*
Knappik et al., J Mol Biol 2000; 296:57-86.*
Robert et al., Int'l J Biol Macromol 2006; 39:51-59.*
Sanchez et al., J Biotechnol. 1999; 72:13-20.*
Wörn et al., J Mol. Biol. 2001; 305:989-1010.*
Zamboni et al., Int'l J. Oncol. 2008; 32:1245-51.*
Adams et al., "Highly Specific in Vivo Tumor Targeting by Monovalent and Divalent Forms of 741F8 Anti-c-*erb*B-2 Single-Chain Fv[1]", *Cancer Research* 1993; 53(17):4026-4034.
Adams et al., "Prolonged in vivo tumor retention of a human diabody targeting the extracellular domain of humanHER2/*neu*", *British Journal of Cancer* 1998; 77(9):1405-1412.
Albrecht et al., "Production of Soluble ScFvs with C-terminal-Free Thiol for Site-Specific Conjugation or Stable Dimeric ScFvs on Demand", *Bioconjugate Chem*. 2004; 15(1):16-26.
Asano et al., "Efficient Construction of a Diabody Using a Refolding System: Anticarcinoembryonic Antigen Recombinant Antibody Fragment", *Journal of Biochemistry, Japanese Biochemical Society*; 2002; 132(6):903-909.
Ayala et al., "Bacterial Single-Chain Antibody Fragments, Specific for the Carcinoembryonic Antigen", *Bio Techniques* 1992; 13(5):790-799.
Benhar, Itai, "Design of synthetic antibody libraries", *Expert Opin. Biol. Ther*. 2007; 7(5):763-779.
Better et al., "*Escherichia coli* Secretion of an Active Chimeric Antibody Fragment", *Science* 1988; 240:1041-1043.
Carter, Paul J., "Potent antibody therapeutics by design", *Nature Reviews Immunology* 2006; 6(5):343-357.
Choi et al., "Production of recombinant proteins by high cell density culture of *Escherichia coli*", *Chemical Engineering Science* 2006; 61:876-885.
George et al., "Redirection of Cellular Cytotoxicity. A Two-Step Approach Using Recombinant Single-Chain Fv Molecules", *Cell Biophysics* 1995; 26(3):153-65.
Goto, Y. and Hamaguchi, K., "The Role of the Intrachain Disulfide Bond in the Conformation and Stability of the Constant Fragment of the Immunoglobulin Light Chain[1]", *J Biochem*. 1979; 86(5):1433:1441.
Graumann K. and Premstaller A.,"Manufacturing of recombinant therapeutic proteins in microbial systems", *Biotechnology Journal* 2006; 1(2):164-186.
Hammarström Sten, "The carcinoembryonic antigen (CEA) family: structures, suggested functions and expression in normal and malignant tissues", *Seminars in Cancer Biology* 1999; 9:67-81.
Holliger et al., "'Diabodies': Small bivalent and bispecific antibody fragments", *Proc Natl Acad Sci USA* 1993 ;90:6444-6448.
Holliger P. and Hudson P.J., "Engineered antibody fragments and the rise of single domains", *Nature Biotechnology* 2005; 23(9):1126-1136.
Hoogenboom, Hennie, "Selecting and screening recombinant antibody libraries", *Nature Biotechnology* 2005; 23(9):1105-1116.
Hu et al., "Minibody: A novel Engineered Anti-Carcinoembryonic Antigen Antibody Fragment (Single-Chain Fv-$C_H3$) Which Exhibits Rapid, High-Level Targeting of Xenografts[1]", *Cancer Research* 1996; 56:3055-3061.
Kim et al., "Antibody Engineering for the Development of Therapeutic Antibodies", *Molecules and Cells* 2005; 20(1):17-29.
Kipriyanov, S.M. and Little, M., "Generation of Recombinant Antibodies", *Molecular Biotechnology* 1999; 12:173-201.
Kortt et al., "Dimeric and trimeric antibodies: high avidity scFvs for cancer targeting", *Biomolecular Engineering, Elsevier* 2001; 18:95-108.
Krop-Watorek et al., "Oligomerization of N-Terminal Domain of Carcinoembryonic Antigen (CEA) Expressed in *Escherichia coli*", *Biochemical and Biophysical Research Communications* 1998; 242:79-83.
Laack et al., "Expression of CEACAM1 in Adenocarcinoma of the Lung: A Factor of Independent Prognostic Significance", *Journal of Clinical Oncology* 2002; 20(21):4279-4284.
Milenic et al., "Construction, Binding Properties, Metabolism, and Tumor Targeting of a Single-Chain Fv Derived from the Pancarcinoma Monoclonal Antibody CC49", *Cancer Research* 1991; 51:6363-6371.

(Continued)

*Primary Examiner* — Sheela J Huff
*Assistant Examiner* — Jessica H Roark
(74) *Attorney, Agent, or Firm* — Kilpatrick Townsend & Stockton LLP

(57) ABSTRACT

An anti-CEA scFv having an uncleaved Pel B leader sequence is surprisingly stable and is highly specific for CEA and CEACAM1.

26 Claims, 28 Drawing Sheets

(56) References Cited

PUBLICATIONS

Mirick et al., "A review of human anti-globulin antibody (HAGA, HAMA, HACA, HAHA) responses to monoclonal antibodies. Not four letter words", *The Quarterly Journal of Nuclear Medicine and Molecular Imaging* 2004; 48(4):251-257.

Müller et al., "Improved Pharmacokinetics of Recombinant Bispecific Antibody Molecules by Fusion to Human Serum Album*", *The Journal of Biological Chemistry* 2007; 282(17):12650-12660.

Neri et al., "Radioactive labeling of recombinant antibody fragments by phosphorylation using human casein kinase II and [$\gamma$-$^{32}$-P]-ATP", *Nature Biotechnology* 1996; 14(4):485-490.

Nolan, O. and O'Kennedy, R., "Bifunctional antibodies: concept, production and applications", *Biochimica Biophysica Acta* 1990; 1040:1-11.

Olafsen et al., "Covalent disulfide-linked anti-CEA diabody allows site-specific conjugation and radiolabeling for tumor targeting applications", *Protein Engineering, Design & Selection* 2004; 17(1):21-27.

Oliveira-Ferrer et al., "Dual Role of Carcinoembryonic Antigen-Related Cell Adhesion Molecule 1 in Angiogenesis and Invasion of Human Urinary Bladder Cancer", *Cancer Research* 2004; 64:8932-8938.

Paetzel et al., "Signal Peptidases", *Chemical Reviews* 2002; 102(12):4549-4579.

Pavoni et al., "Selection, affinity maturation, and characterization of a human scFv antibody against CEA protein", *BMC Cancer* 2006; 6(41):1-15.

Pennacchioni et al., "Radiopharmaceuticals & Radiochemistry & Dosiometry: PET radiopharmaceutical evaluation", Internet citation; 2011, XP007919589.

Proba et al., "A Natural Antibody Missing a Cysteine in $V_H$: Consequences for Thermodynamic Stability and Folding", *J Mol. Biol.* 1997; 265:161-172.

Rath et al., "An inhibition enzyme immunoassay for estimating relative antibody affinity and affinity heterogeneity", *Journal of Immunoogical Methods, Elsevier* 1988; 106(2):245-249.

Rudikoff, S. and Pumphrey, J. G., "Functional antibody lacking a variable-region disulfide bridge", *Proc. Natl Acad. Sci. USA* 1986; 83:7875-7878.

Rudnick, S.I. and Adams, G.P., "Affinity and Avidity in Antibody-Based Tumor Targeting", *Cancer Biotherapy Radiopharmaceuticals* 2009; 24(2):155-161.

Sharkey, R.M. and Goldenberg, D.M., "Targeted Therapy of Cancer: New Prospects for Antibodies and Immunoconjugates[1]" *CA A Cancer Journal for Clinicians* 2006; 56(4):226-243.

Skerra, A. and Plückthun*, A., "Assembly of a Functional Immunoglobulin F$_v$Fragment in *Escherichia coli*", *Science* 1988; 240:1038-1041.

Sletta et al., "The Presence of N-terminal Secretion Signal Sequences Leads to Strong Stimulation of the Total Expression Levels of Three Tested Medically Important Proteins during High-Cell-Density Cultivations of *Escherichia coli*", *Applied Environmental Microbiology* 2007; 73(3):906-912.

Stork et al., "N-Glycosylation as Novel Strategy to Improve Pharmacokinetic Properties of Bispecific Single-chain Diabodies*", *The Journal of Biological Chemistry* 2008; 283(12):7804-7812.

Sundaresan et al., "$^{124}$I-Labeled Engineered Anti-CEA Minibodies and Diabodies Allow High-Contrast, Antigen- Specific Small-Animal PET Imaging of Xenografts in Athymic Mice", *The Journal of Nuclear Medicine* 2003; 44(12):1962-1969.

Thies et al., "Overexpression of the cell adhesion molecule L1 is associated with metastasis in cutaneous malignant melanoma", *European Journal of Cancer* 2002; 38:1708-1716.

Verel et al., "Tumor targeting of antibodies with different affinity for target antigen CD44V6 in nude mice bearing head and neck cancer xenograft", *Int. J. Cancer* 2002; 99:396-402.

Wang et al., "Cloning and expression of CEA single chain Fv gene in *E. coli*", *Chin. J. Microbiol. Immunol.; Zhongua Weishengwuxue He Mianyixue* 1998; 18(6):486-489, XP001526132, ISSN: 0254-5101 (English Abstract).

Wu et al., "Tumor localization of anti-CEA single-chain Fvs: improved targeting by non-covalent dimers", *Immunotechnology* 1996; 2:21-36.

Wu et al., "Anti-carcinoembryonic antigen (CEA) diabody for rapid tumor targeting and imaging", *Tumor Targeting* 1999; 4:47-58.

Yazaki et al., "Tumor Targeting of Radiometal Labeled Anti-CEA Recombinant T84.66 Diabody and T84.66 Minibody: Comparison to Radioiodinated Fragments", *Bioconjugate Chem.* 2001; 12:220-228.

Yokota et al., "Rapid Tumor Penetration of a Single-Chain Fv and Comparison with Other Immunoglobulin Forms", *Cancer Research* 1992; 52(12):3402-3408.

International Preliminary Report on Patentability and Written Opinion dated Dec. 28, 2012 for International Application No. PCT/EP2011/003444, 7 pages.

International Search Report dated Nov. 8, 2011 for International Applicaton No. PCT/EP2011/003444, 5 pages.

* cited by examiner

*Flow-scheme of Up-stream Processes*

```
STARTER CULTURE:
Inoculate basic media with transformed cells E.coli BL21 (DE3)
and incubate at 37°C at 200rpm for 16-18 h
           |
Measure O.D 600nm and
diluition of the starter culture for the fermentation phase
           |
FERMENTATION:
Inoculate in the BIOSTAT C15 for fermentation phase
           |
When O.D 600nm reach 10 Abs
add IPTG for induction DIATHIS-1
           |
after 4h from induction
harvesting and centrifugation
```

Fig. 3A

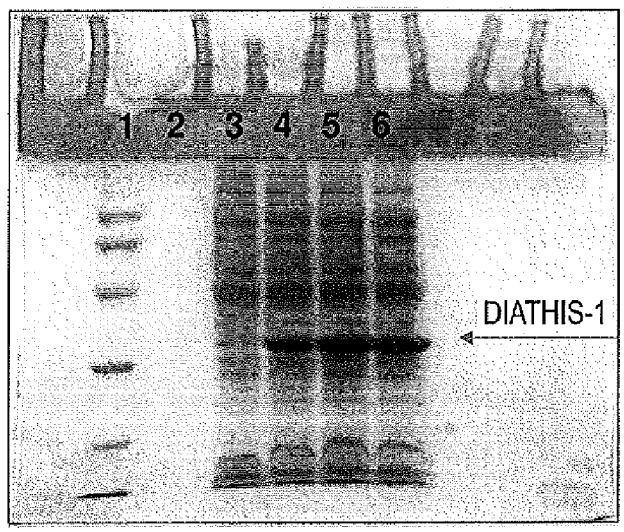

Fig. 3B

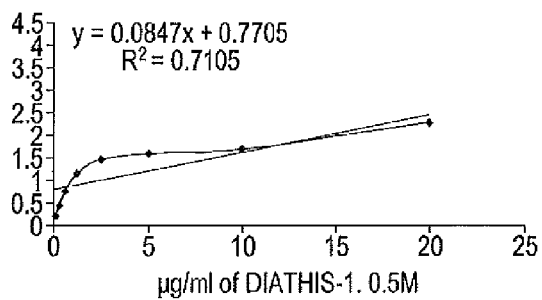 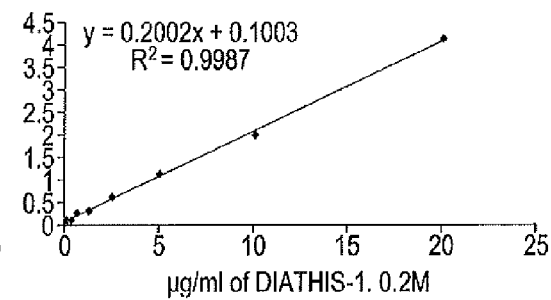
Fig. 6A  Fig. 6B
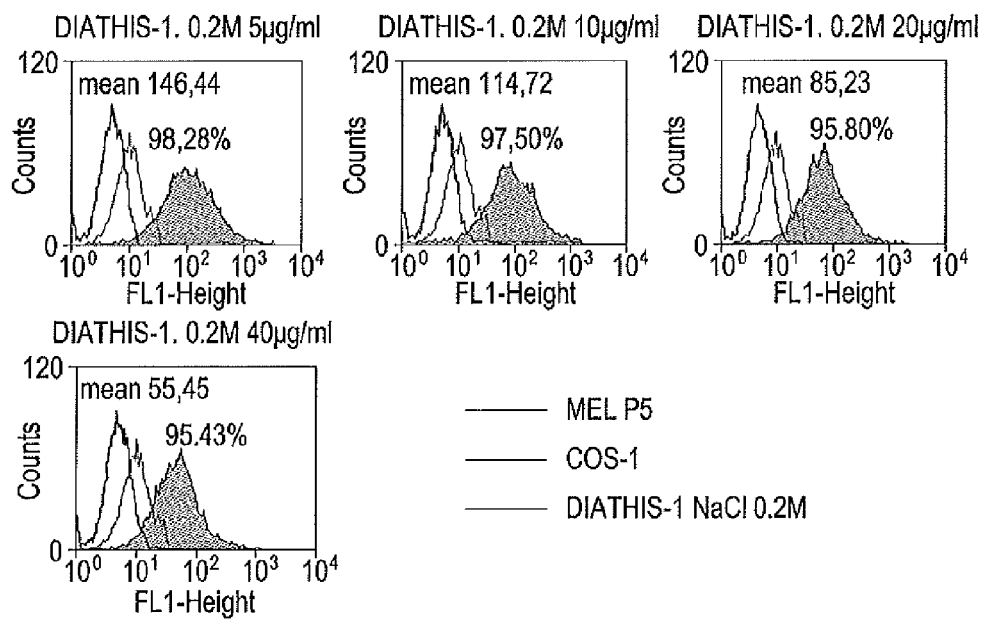
Fig. 7 scFv DIATHIS-1:Ubiquitin
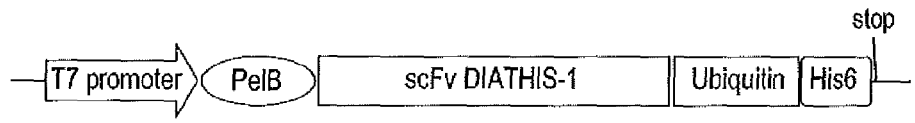
scFv DIATHIS-1:HIV-1 vpr
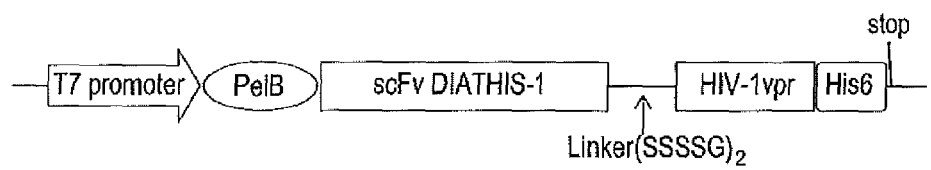
scFv DIATHIS-1:Yeast Cystosine Deaminase (YCD)
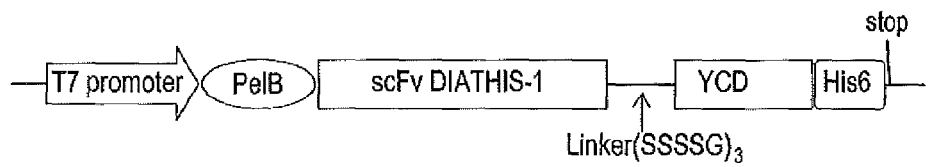
scFv DIATHIS-1:Listeriolysin-O (LLO) delta PEST
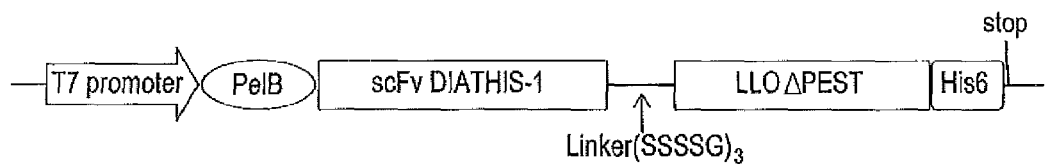
scF scFvDIATHIS-1:
Pel B sequence leader
```
  1  ATG AAA TAC CTG CTG CCG ACG GCT GCT GCT GGT CTG CTG CTC CTC
GCT GCC CAG CCG GCG  60
  1  Met Lys Tyr Leu Leu Pro Thr Ala Ala Ala Gly Leu Leu Leu Leu
Ala Ala Gln Pro Ala  20

61  ATG GCC  66
 21  Met Ala  22
```
VH
```
 67  ATG GCC GAG GTG CAG CTG GCG GAG TCT GGG GGA GGC TTG GTA CAG
CCT GGG GGG TCC CTG  126
 23  Met Ala Glu Val Gln Leu Ala Glu Ser Gly Gly Gly Leu Val Gln
Pro Gly Gly Ser Leu  42

127  AGA CTC TCC TGT GCC GCC TCT GGA TTC ACC TTT AGC AGC GAT GCC
ATG AGC TGG GTC CGC  186
 43  Arg Leu Ser Cys Ala Ala Ser Gly Phe Thr Phe Ser Ser Asp Ala
Met Ser Trp Val Arg  62

187  CAG GCT CCA GGG AAG GGG CTG GAG TGG GTC TCA GCT ATT AGT GGT
AGT GGT GGT AGC ACA  246
 63  Gln Ala Pro Gly Lys Gly Leu Glu Trp Val Ser Ala Ile Ser Gly
Ser Gly Gly Ser Thr  82

247  TAC TAC GCA GAC TCC GTG AAG GGC CGG TTC ACC ATC TCC AGA GAC
AAT TCC AAG AAC ACG  306
 83  Tyr Tyr Ala Asp Ser Val Lys Gly Arg Phe Thr Ile Ser Arg Asp
Asn Ser Lys Asn Thr  102

307  CTG TAT CTG CAA ATG AAC AGC CTG AGA GCC GAG GAC ACG GCC GTA
TAT TAC TGT GCG AAA  366
103  Leu Tyr Leu Gln Met Asn Ser Leu Arg Ala Glu Asp Thr Ala Val
Tyr Tyr Cys Ala Lys  122

367  AGT AAT GAG TTT CTT TTT GAC TAC TGG GGC CAG GGA ACT CTG GTC
ACC GTG TCG AGA  423
123  Ser Asn Glu Phe Leu Phe Asp Tyr Trp Gly Gln Gly Thr Leu Val
Thr Val Ser Arg  141
```

Linker:
```
424  GGT GGA GGC GGT TCA GGC GGA GGT GGC TCT GGC GGT GGC GGA TCG
468
142  Gly Gly Gly Gly Ser Gly Gly Gly Gly Ser Gly Gly Gly Gly Ser
156
```

VL
```
469  TCT GAG CTG ACT CAG GAC CCT GCT GTG TCT GTG GCC TTG GGA CAG
ACA GTC AGG ATC ACA  528
```

FIG. 15

```
157  Ser Glu Leu Thr Gln Asp Pro Ala Val Ser Val Ala Leu Gly Gln
Thr Val Arg Ile Thr  176

529  TGC CAA GGA GAC AGC CTC AGA AGC TCT TAT GCA AGC TGG TAC CGG
CAG AGG CCA GGA CAG  588
177  Cys Gln Gly Asp Ser Leu Arg Ser Ser Tyr Ala Ser Trp Tyr Arg
Gln Arg Pro Gly Gln  196

589  GCC *CCT GTA CCT GTC ATC TAT GGT AAG AAC AAC *TGG CCC TCA GGG
ATC CCA GAC CGG TTC  648
197  Ala *Pro Val Pro Val Ile Tyr Gly Lys Asn Asn *Trp Pro Ser Gly
Ile Pro Asp Arg Phe  216

649  TCT GGC TCC AGC TCA GGA AAC ACA GCT TCC TTG ACC ATC ACT GGG
GCT CAG GCG GAA GAT  708
217  Ser Gly Ser Ser Ser Gly Asn Thr Ala Ser Leu Thr Ile Thr Gly
Ala Gln Ala Glu Asp  236

709  GAG GCT GAC TAT TAC *TGT AAC TCC TCT TAT GCG TGG CTG CCC TAT
GTG GTA TTC GGC GGA  768
237  Glu Ala Asp Tyr Tyr *Cys Asn Ser Ser Tyr Ala Trp Leu Pro Tyr
Val Val Phe Gly Gly  256

769   GGG ACC AAG CTG ACC GTC CTA GGC GCG GCC GCA     801
257   Gly Thr Lys Leu Thr Val Leu Gly Ala Ala Ala     267

D3SD3-FLAG-His6 tag
802  GAT GAC GAT TCC GAC GAC GAT GAC TAC AAG GAC GAC GAT GAC AAG
CAC CAT CAC CAT CAC  861
268  Asp Asp Asp Ser Asp Asp Asp Asp Tyr Lys Asp Asp Asp Asp Lys
His His His His His  287

862  CAT  864
288  His  288
```

FIG. 15 (Con't)

scFvDIATHIS-1: Ubiquitin
Pel B sequence leader
  1 ATG AAA TAC CTG CTG CCG ACG GCT GCT GCT GGT CTG CTG CTC CTC
GCT GCC CAG CCG GCG   60
  1 Met Lys Tyr Leu Leu Pro Thr Ala Ala Ala Gly Leu Leu Leu Leu
Ala Ala Gln Pro Ala   20

61 ATG GCC   66
 21 Met Ala   22
VH
 67 ATG GCC GAG GTG CAG CTG GCG GAG TCT GGG GGA GGC TTG GTA CAG
CCT GGG GGG TCC CTG   126
 23 Met Ala Glu Val Gln Leu Ala Glu Ser Gly Gly Gly Leu Val Gln
Pro Gly Gly Ser Leu   42

127 AGA CTC TCC TGT GCC GCC TCT GGA TTC ACC TTT AGC AGC GAT GCC
ATG AGC TGG GTC CGC   186
 43 Arg Leu Ser Cys Ala Ala Ser Gly Phe Thr Phe Ser Ser Asp Ala
Met Ser Trp Val Arg   62

187 CAG GCT CCA GGG AAG GGG CTG GAG TGG GTC TCA GCT ATT AGT GGT
AGT GGT GGT AGC ACA   246
 63 Gln Ala Pro Gly Lys Gly Leu Glu Trp Val Ser Ala Ile Ser Gly
Ser Gly Gly Ser Thr   82

247 TAC TAC GCA GAC TCC GTG AAG GGC CGG TTC ACC ATC TCC AGA GAC
AAT TCC AAG AAC ACG   306
 83 Tyr Tyr Ala Asp Ser Val Lys Gly Arg Phe Thr Ile Ser Arg Asp
Asn Ser Lys Asn Thr   102

307 CTG TAT CTG CAA ATG AAC AGC CTG AGA GCC GAG GAC ACG GCC GTA
TAT TAC TGT GCG AAA   366
103 Leu Tyr Leu Gln Met Asn Ser Leu Arg Ala Glu Asp Thr Ala Val
Tyr Tyr Cys Ala Lys   122

367 AGT AAT GAG TTT CTT TTT GAC TAC TGG GGC CAG GGA ACT CTG GTC
ACC GTG TCG AGA   423
123 Ser Asn Glu Phe Leu Phe Asp Tyr Trp Gly Gln Gly Thr Leu Val
Thr Val Ser Arg   141

Linker:
424 GGT GGA GGC GGT TCA GGC GGA GGT GGC TCT GGC GGT GGC GGA TCG
468
142 Gly Gly Gly Gly Ser Gly Gly Gly Gly Ser Gly Gly Gly Ser
156

VL
469 TCT GAG CTG ACT CAG GAC CCT GCT GTG TCT GTG GCC TTG GGA CAG
ACA GTC AGG ATC ACA   528
157 Ser Glu Leu Thr Gln Asp Pro Ala Val Ser Val Ala Leu Gly Gln
Thr Val Arg Ile Thr   176

FIG. 16

```
529  TGC CAA GGA GAC AGC CTC AGA AGC TCT TAT GCA AGC TGG TAC CGG
CAG AGG CCA GGA CAG  588
177  Cys Gln Gly Asp Ser Leu Arg Ser Ser Tyr Ala Ser Trp Tyr Arg
Gln Arg Pro Gly Gln  196

589  GCC *CCT GTA CCT GTC ATC TAT GGT AAG AAC AAC *TGG CCC TCA GGG
ATC CCA GAC CGG TTC  648
197  Ala *Pro Val Pro Val Ile Tyr Gly Lys Asn Asn *Trp Pro Ser Gly
Ile Pro Asp Arg Phe  216

649  TCT GGC TCC AGC TCA GGA AAC ACA GCT TCC TTG ACC ATC ACT GGG
GCT CAG GCG GAA GAT  708
217  Ser Gly Ser Ser Ser Gly Asn Thr Ala Ser Leu Thr Ile Thr Gly
Ala Gln Ala Glu Asp  236

709  GAG GCT GAC TAT TAC *TGT AAC TCC TCT TAT GCG TGG CTG CCC TAT
GTG GTA TTC GGC GGA  768
237  Glu Ala Asp Tyr Tyr *Cys Asn Ser Ser Tyr Ala Trp Leu Pro Tyr
Val Val Phe Gly Gly  256

769  GGG ACC AAG CTG ACC GTC CTA GGC GCG GCC GCA   801
257  Gly Thr Lys Leu Thr Val Leu Gly Ala Ala Ala   267
```
Ubiquitin:
```
802  ATG CAG ATC TTC GTC AAG ACG TTA ACC GGT AAA ACC ATA ACT CTA
GAA GTT GAA CCA TCC  861
268  Met Gln Ile Phe Val Lys Thr Leu Thr Gly Lys Thr Ile Thr Leu
Glu Val Glu Pro Ser  287

862  GAT ACC ATC GAA AAC GTT AAG GCT AAA ATT CAA GAC AAG GAA GGC
ATT CCA CCT GAT CAA  921
288  Asp Thr Ile Glu Asn Val Lys Ala Lys Ile Gln Asp Lys Glu Gly
Ile Pro Pro Asp Gln  307

922  CAA AGA TTG ATC TTT GCC GGT AAG CAG CTC GAG GAC GGT AGA ACG
CTG TCT GAT TAC AAC  981
308  Gln Arg Leu Ile Phe Ala Gly Lys Gln Leu Glu Asp Gly Arg Thr
Leu Ser Asp Tyr Asn  327

982  ATT CAG AAG GAG TCG ACC TTA CAT CTT GTC TTA AGA CTA AGA GGT
GCG GCC GCA CTC GAG 1041
328  Ile Gln Lys Glu Ser Thr Leu His Leu Val Leu Arg Leu Arg Gly
Ala Ala Ala Leu Glu  347
```
His 6 tag:
```
1042  CAC CAC CAC CAC CAC CAC   1059
348   His His His His His His    353
```

FIG. 16 (Con't)

scFvDIATHIS-1:HIV-vpr
Pel B sequence leader
  1  ATG AAA TAC CTG CTG CCG ACG GCT GCT GCT GGT CTG CTG CTC CTC GCT GCC CAG CCG GCG  60
  1  Met Lys Tyr Leu Leu Pro Thr Ala Ala Ala Gly Leu Leu Leu Leu Ala Ala Gln Pro Ala  20

61  ATG GCC  66
 21  Met Ala  22
VH
 67  ATG GCC GAG GTG CAG CTG GCG GAG TCT GGG GGA GGC TTG GTA CAG CCT GGG GGG TCC CTG  126
 23  Met Ala Glu Val Gln Leu Ala Glu Ser Gly Gly Gly Leu Val Gln Pro Gly Gly Ser Leu  42

127  AGA CTC TCC TGT GCC GCC TCT GGA TTC ACC TTT AGC AGC GAT GCC ATG AGC TGG GTC CGC  186
 43  Arg Leu Ser Cys Ala Ala Ser Gly Phe Thr Phe Ser Ser Asp Ala Met Ser Trp Val Arg  62

187  CAG GCT CCA GGG AAG GGG CTG GAG TGG GTC TCA GCT ATT AGT GGT AGT GGT GGT AGC ACA  246
 63  Gln Ala Pro Gly Lys Gly Leu Glu Trp Val Ser Ala Ile Ser Gly Ser Gly Gly Ser Thr  82

247  TAC TAC GCA GAC TCC GTG AAG GGC CGG TTC ACC ATC TCC AGA GAC AAT TCC AAG AAC ACG  306
 83  Tyr Tyr Ala Asp Ser Val Lys Gly Arg Phe Thr Ile Ser Arg Asp Asn Ser Lys Asn Thr  102

307  CTG TAT CTG CAA ATG AAC AGC CTG AGA GCC GAG GAC ACG GCC GTA TAT TAC TGT GCG AAA  366
103  Leu Tyr Leu Gln Met Asn Ser Leu Arg Ala Glu Asp Thr Ala Val Tyr Tyr Cys Ala Lys  122

367  AGT AAT GAG TTT CTT TTT GAC TAC TGG GGC CAG GGA ACT CTG GTC ACC GTG TCG AGA  423
123  Ser Asn Glu Phe Leu Phe Asp Tyr Trp Gly Gln Gly Thr Leu Val Thr Val Ser Arg  141

Linker:
424  GGT GGA GGC GGT TCA GGC GGA GGT GGC TCT GGC GGT GGC GGA TCG  468
142  Gly Gly Gly Gly Ser Gly Gly Gly Ser Gly Gly Gly Ser  156

VL
469  TCT GAG CTG ACT CAG GAC CCT GCT GTG TCT GTG GCC TTG GGA CAG ACA GTC AGG ATC ACA  528
157  Ser Glu Leu Thr Gln Asp Pro Ala Val Ser Val Ala Leu Gly Gln Thr Val Arg Ile Thr  176

FIG. 17

529  TGC CAA GGA GAC AGC CTC AGA AGC TCT TAT GCA AGC TGG TAC CGG CAG AGG CCA GGA CAG  588
177  Cys Gln Gly Asp Ser Leu Arg Ser Ser Tyr Ala Ser Trp Tyr Arg Gln Arg Pro Gly Gln  196

589  GCC *CCT GTA CCT GTC ATC TAT GGT AAG AAC AAC *TGG CCC TCA GGG ATC CCA GAC CGG TTC  648
197  Ala *Pro Val Pro Val Ile Tyr Gly Lys Asn Asn *Trp Pro Ser Gly Ile Pro Asp Arg Phe  216

649  TCT GGC TCC AGC TCA GGA AAC ACA GCT TCC TTG ACC ATC ACT GGG GCT CAG GCG GAA CAT  708
217  Ser Gly Ser Ser Ser Gly Asn Thr Ala Ser Leu Thr Ile Thr Gly Ala Gln Ala Glu Asp  236

709  GAG GCT GAC TAT TAC *TGT AAC TCC TCT TAT GCG TGG CTG CCC TAT GTG GTA TTC GGC GGA  768
237  Glu Ala Asp Tyr Tyr *Cys Asn Ser Ser Tyr Ala Trp Leu Pro Tyr Val Val Phe Gly Gly  256

769  GGG ACC AAG CTG ACC GTC CTA GGC GCG GCC GCA  801
257  Gly Thr Lys Leu Thr Val Leu Gly Ala Ala Ala  267
Linker:
802  TCT TCC TCA TCG GGT AGT AGC TCT TCC GGC  831
268  Ser Ser Ser Ser Gly Ser Ser Ser Ser Gly  277
HIV-vpr
832  ATG GAA CAA GCC CCA GAA GAC CAA GGG CCA CAG AGG GAG CCA CAC AAT GAA TGG ACA CTA  891
278  Met Glu Gln Ala Pro Glu Asp Gln Gly Pro Gln Arg Glu Pro His Asn Glu Trp Thr Leu  297

892  GAG CTT TTA GAG GAG CTT AAG AAT GAA GCT GTT AGA CAT TTT CCT AGG ATT TGG CTC CAT  951
298  Glu Leu Leu Glu Glu Leu Lys Asn Glu Ala Val Arg His Phe Pro Arg Ile Trp Leu His  317

852  GGC TTA GGG CAA CAT ATC TAT GAA ACT TAT GGG GAT ACT TGG GCA GGA GTG GAA GCC ATA  1011
318  Gly Leu Gly Gln His Ile Tyr Glu Thr Tyr Gly Asp Thr Trp Ala Gly Val Glu Ala Ile  337

1012 ATA AGA ATT CTG CAA CAA CTG CTG TTT ATC CAT TTC AGA ATT GGG TGT CGA CAT AGC AGA  1071
338  Ile Arg Ile Leu Gln Gln Leu Leu Phe Ile His Phe Arg Ile Gly Cys Arg His Ser Arg  357

1072 ATA GGC GTT ACT CAA CAG AGG AGA GCA AGA AAT GGA GCC AGT AGA TCC GCG GCC GCA CTC  1131
358  Ile Gly Val Thr Gln Gln Arg Arg Ala Arg Asn Gly Ala Ser Arg Ser Ala Ala Ala Leu  377

FIG. 17 (Con't)

1132 GAG 1134
378  Glu 378
His6
1135 CAC CAC CAC CAC CAC CAC 1152
379  His His His His His His 384

FIG. 17 (Con't)

scFvDIATHIS-1:YCD
Pel B sequence leader
  1 ATG AAA TAC CTG CTG CCG ACG GCT GCT GCT GGT CTG CTG CTC CTC
GCT GCC CAG CCG GCG   60
  1 Met Lys Tyr Leu Leu Pro Thr Ala Ala Ala Gly Leu Leu Leu Leu
Ala Ala Gln Pro Ala   20

61 ATG GCC   66
 21 Met Ala   22
VH
 67 ATG GCC GAG GTG CAG CTG GCG GAG TCT GGG GGA GGC TTG GTA CAG
CCT GGG GGG TCC CTG   126
 23 Met Ala Glu Val Gln Leu Ala Glu Ser Gly Gly Gly Leu Val Gln
Pro Gly Gly Ser Leu   42

127 AGA CTC TCC TGT GCC GCC TCT GGA TTC ACC TTT AGC AGC GAT GCC
ATG AGC TGG GTC CGC   186
 43 Arg Leu Ser Cys Ala Ala Ser Gly Phe Thr Phe Ser Ser Asp Ala
Met Ser Trp Val Arg   62

187 CAG GCT CCA GGG AAG GGG CTG GAG TGG GTC TCA GCT ATT AGT GGT
AGT GGT GGT AGC ACA   246
 63 Gln Ala Pro Gly Lys Gly Leu Glu Trp Val Ser Ala Ile Ser Gly
Ser Gly Gly Ser Thr   82

247 TAC TAC GCA GAC TCC GTG AAG GGC CGG TTC ACC ATC TCC AGA GAC
AAT TCC AAG AAC ACG   306
 83 Tyr Tyr Ala Asp Ser Val Lys Gly Arg Phe Thr Ile Ser Arg Asp
Asn Ser Lys Asn Thr   102

307 CTG TAT CTG CAA ATG AAC AGC CTG AGA GCC GAG GAC ACG GCC GTA
TAT TAC TGT GCG AAA   366
103 Leu Tyr Leu Gln Met Asn Ser Leu Arg Ala Glu Asp Thr Ala Val
Tyr Tyr Cys Ala Lys   122

367 AGT AAT GAG TTT CTT TTT GAC TAC TGG GGC CAG GGA ACT CTG GTC
ACC GTG TCG AGA   423
123 Ser Asn Glu Phe Leu Phe Asp Tyr Trp Gly Gln Gly Thr Leu Val
Thr Val Ser Arg   141

Linker:

FIG. 18

```
424  GGT GGA GGC GGT TCA GGC GGA GGT GGC TCT GGC GGT GGC GGA TCG
468
142  Gly Gly Gly Gly Ser Gly Gly Gly Gly Ser Gly Gly Gly Gly Ser
156

VL
469  TCT GAG CTG ACT CAG GAC CCT GCT GTG TCT GTG GCC TTG GGA CAG
ACA GTC AGG ATC ACA  528
157  Ser Glu Leu Thr Gln Asp Pro Ala Val Ser Val Ala Leu Gly Gln
Thr Val Arg Ile Thr  176

529  TGC CAA GGA GAC AGC CTC AGA AGC TCT TAT GCA AGC TGG TAC CGG
CAG AGG CCA GGA CAG  588
177  Cys Gln Gly Asp Ser Leu Arg Ser Ser Tyr Ala Ser Trp Tyr Arg
Gln Arg Pro Gly Gln  196

589 GCC *CCT GTA CCT GTC ATC TAT GGT AAG AAC AAC *TGG CCC TCA GGG
ATC CCA GAC CGG TTC 648
197 Ala *Pro Val Pro Val Ile Tyr Gly Lys Asn Asn *Trp Pro Ser Gly
Ile Pro Asp Arg Phe 216

649  TCT GGC TCC AGC TCA GGA AAC ACA GCT TCC TTG ACC ATC ACT GGG
GCT CAG GCG GAA GAT  708
217  Ser Gly Ser Ser Ser Gly Asn Thr Ala Ser Leu Thr Ile Thr Gly
Ala Gln Ala Glu Asp  236

709  GAG GCT GAC TAT TAC *TGT AAC TCC TCT TAT GCG TGG CTG CCC TAT
GTG GTA TTC GGC GGA 768
237  Glu Ala Asp Tyr Tyr *Cys Asn Ser Ser Tyr Ala Trp Leu Pro Tyr
Val Val Phe Gly Gly 256

769  GGG ACC AAG CTG ACC GTC CTA GGC GCG GCC GCA       801
257  Gly Thr Lys Leu Thr Val Leu Gly Ala Ala Ala       267

Linker
802  TCT TCC TCA TCG GGT AGT AGC TCT TCC GGC TCA TCG TCC AGC GGC
846
268  Ser Ser Ser Ser Gly Ser Ser Ser Ser Gly Ser Ser Ser Ser Gly
282
YCD
847  ATG GTG ACA GGG GGA ATG GCA AGC AAG TGG GAT CAG AAA GGC ATG
GAC ATT GCC TAT GAA 906
283  Met Val Thr Gly Gly Met Ala Ser Lys Trp Asp Gln Lys Gly Met
Asp Ile Ala Tyr Glu 302

907  GAG GCC GCA CTG GGC TAC AAA GAA GGC GGT GTG CCG ATT GGC GGT
TGT CTG ATC AAT AAC 966
303  Glu Ala Ala Leu Gly Tyr Lys Glu Gly Gly Val Pro Ile Gly Gly
Cys Leu Ile Asn Asn 322
```

FIG. 18 (Con't)

967  AAA GAC GGC TCC GTG CTG GGC CGT GGG CAC AAC ATG CGC TTC CAG
AAA GGC AGC GCC ACC 1026
323  Lys Asp Gly Ser Val Leu Gly Arg Gly His Asn Met Arg Phe Gln
Lys Gly Ser Ala Thr  342

1027 CTG CAC GGC GAA ATC TCC ACC CTG GAA AAC TGC GGG CGT CTC GAG
GGC AAA GTG TAC AAA 1086
343  Leu His Gly Glu Ile Ser Thr Leu Glu Asn Cys Gly Arg Leu Glu
Gly Lys Val Tyr Lys 362

1087 GAT ACC ACC CTG TAT ACG ACC CTG AGC CCG TGC GAC ATG TGT ACG
GGC GCC ATC ATC ATG 1146
363  Asp Thr Thr Leu Tyr Thr Thr Leu Ser Pro Cys Asp Met Cys Thr
Gly Ala Ile Ile Met 382

1147 TAC GGC ATT CCA CGC TGC GTG GTC GGC GAA AAC GTG AAT TTC AAA
TCC AAG GGC GAG AAA 1206
383  Tyr Gly Ile Pro Arg Cys Val Val Gly Glu Asn Val Asn Phe Lys
Ser Lys Gly Glu Lys 402

1207 TAC CTG CAG ACC CGC GGC CAC GAA GTG GTC GTG GTG GAC GAT GAA
CGC TGC AAA AAG ATC 1266
403  Tyr Leu Gln Thr Arg Gly His Glu Val Val Val Val Asp Asp Glu
Arg Cys Lys Lys Ile 422

1267 ATG AAA CAG TTC ATC GAT GAG CGT CCA CAG GAT TGG TTT GAA GAT
ATT CCT GAG GCG GCC 1326
423  Met Lys Gln Phe Ile Asp Glu Arg Pro Gln Asp Trp Phe Glu Asp
Ile Pro Glu Ala Ala 442

1327  GCA CTC GAG 1335
443   Ala Leu Glu 445
His6
1336  CAC CAC CAC CAC CAC CAC 1353
446   His His His His His His 451

FIG. 18 (Con't)

scFvDIATHIS-1:LLOΔPEST
Pel B sequence leader
 1  ATG AAA TAC CTG CTG CCG ACG GCT GCT GCT GGT CTG CTG CTC CTC
GCT GCC CAG CCG GCG  60
 1  Met Lys Tyr Leu Leu Pro Thr Ala Ala Ala Gly Leu Leu Leu Leu
Ala Ala Gln Pro Ala  20

61  ATG GCC  66
21  Met Ala  22
VH
67   ATG GCC GAG GTG CAG CTG GCG GAG TCT GGG GGA GGC TTG GTA CAG
CCT GGG GGG TCC CTG  126
23   Met Ala Glu Val Gln Leu Ala Glu Ser Gly Gly Gly Leu Val Gln
Pro Gly Gly Ser Leu  42

FIG. 19

```
127  AGA CTC TCC TGT GCC GCC TCT GGA TTC ACC TTT AGC AGC GAT GCC
ATG AGC TGG GTC CGC  186
 43  Arg Leu Ser Cys Ala Ala Ser Gly Phe Thr Phe Ser Ser Asp Ala
Met Ser Trp Val Arg   62

187  CAG GCT CCA GGG AAG GGG CTG GAG TGG GTC TCA GCT ATT AGT GGT
AGT GGT GGT AGC ACA  246
 63  Gln Ala Pro Gly Lys Gly Leu Glu Trp Val Ser Ala Ile Ser Gly
Ser Gly Gly Ser Thr   82

247  TAC TAC GCA GAC TCC GTG AAG GGC CGG TTC ACC ATC TCC AGA GAC
AAT TCC AAG AAC ACG  306
 83  Tyr Tyr Ala Asp Ser Val Lys Gly Arg Phe Thr Ile Ser Arg Asp
Asn Ser Lys Asn Thr  102

307  CTG TAT CTG CAA ATG AAC AGC CTG AGA GCC GAG GAC ACG GCC GTA
TAT TAC TGT GCG AAA  366
103  Leu Tyr Leu Gln Met Asn Ser Leu Arg Ala Glu Asp Thr Ala Val
Tyr Tyr Cys Ala Lys  122

367  AGT AAT GAG TTT CTT TTT GAC TAC TGG GGC CAG GGA ACT CTG GTC
ACC GTG TCG AGA  423
123  Ser Asn Glu Phe Leu Phe Asp Tyr Trp Gly Gln Gly Thr Leu Val
Thr Val Ser Arg  141

Linker:
424  GGT GGA GGC GGT TCA GGC GGA GGT GGC TCT GGC GGT GGC GGA TCG
468
142  Gly Gly Gly Gly Ser Gly Gly Gly Gly Ser Gly Gly Gly Gly Ser
156

VL
469  TCT GAG CTG ACT CAG GAC CCT GCT GTG TCT GTG GCC TTG GGA CAG
ACA GTC AGG ATC ACA  528
157  Ser Glu Leu Thr Gln Asp Pro Ala Val Ser Val Ala Leu Gly Gln
Thr Val Arg Ile Thr  176

529  TGC CAA GGA GAC AGC CTC AGA AGC TCT TAT GCA AGC TGG TAC CGG
CAG AGG CCA GGA CAG  588
177  Cys Gln Gly Asp Ser Leu Arg Ser Ser Tyr Ala Ser Trp Tyr Arg
Gln Arg Pro Gly Gln  196

589  GCC *CCT GTA CCT GTC ATC TAT GGT AAG AAC AAC *TGG CCC TCA GGG
ATC CCA GAC CGG TTC  648
197  Ala *Pro Val Pro Val Ile Tyr Gly Lys Asn Asn *Trp Pro Ser Gly
Ile Pro Asp Arg Phe  216

649  TCT GGC TCC AGC TCA GGA AAC ACA GCT TCC TTG ACC ATC ACT GGG
GCT CAG GCG AAA GAT  708
```

FIG. 19 (Con't)

```
217  Ser Gly Ser Ser Ser Gly Asn Thr Ala Ser Leu Thr Ile Thr Gly
Ala Gln Ala Glu Asp  236

709  GAG GCT GAC TAT TAC *TGT AAC TCC TCT TAT GCG TGG CTG CCC TAT
GTG GTA TTC GGC GGA 768
237  Glu Ala Asp Tyr Tyr *Cys Asn Ser Ser Tyr Ala Trp Leu Pro Tyr
Val Val Phe Gly Gly 256

769  GGG ACC AAG CTG ACC GTC CTA GGC GCG GCC GCA    801
257  Gly Thr Lys Leu Thr Val Leu Gly Ala Ala Ala    267
Linker
802  TCT TCC TCA TCG GGT AGT AGC TCT TCC GGC TCA TCG TCC AGC GGC
846
268  Ser Ser Ser Ser Gly Ser Ser Ser Ser Gly Ser Ser Ser Ser Gly
282
LLOAPEST
847  ATG GAA ATC GAT AAG TAT ATA CAA GGA TTG GAT TAC AAT AAA AAC
AAT GTA TTA GTA TAC  906
283  Met Glu Ile Asp Lys Tyr Ile Gln Gly Leu Asp Tyr Asn Lys Asn
Asn Val Leu Val Tyr  302

907  CAC GGA GAT GCA GTG ACA AAT GTG CCG CCA AGA AAA GGT TAC AAA
GAT GGA AAT GAA TAT  966
303  His Gly Asp Ala Val Thr Asn Val Pro Pro Arg Lys Gly Tyr Lys
Asp Gly Asn Glu Tyr  322

967  ATC GTT GTG GAG AAA AAG AAG AAA TCC ATC AAT CAA AAT AAT GCA
GAC ATC CAA GTT GTA  1026
323  Ile Val Val Glu Lys Lys Lys Lys Ser Ile Asn Gln Asn Asn Ala
Asp Ile Gln Val Val  342

1027 AAT GCA ATT TCG AGC CTA ACA TAT CCA GGT GCT CTC GTA AAA GCG
AAT TCG GAA TTA GTA 1086
343  Asn Ala Ile Ser Ser Leu Thr Tyr Pro Gly Ala Leu Val Lys Ala
Asn Ser Glu Leu Val  362

1087 GAA AAT CAA CCA GAT GTT CTC CCT GTA AAA CGT GAT TCA TTA ACA
CTT AGC ATC GAT TTG 1146
363  Glu Asn Gln Pro Asp Val Leu Pro Val Lys Arg Asp Ser Leu Thr
Leu Ser Ile Asp Leu 382

1147 CCA GGA ATG ACT AAT CAA GAC AAT AAA ATC GTT GTA AAA AAT GCT
ACT AAA TCG AAT GTT 1206
383  Pro Gly Met Thr Asn Gln Asp Asn Lys Ile Val Val Lys Asn Ala
Thr Lys Ser Asn Val 402

1207 AAC AAC GCA GTA AAT ACA TTA GTG GAA AGA TGG AAT GAA AAA TAT
GCT CAA GCT TAT CCG 1266
403  Asn Asn Ala Val Asn Thr Leu Val Glu Arg Trp Asn Glu Lys Tyr
Ala Gln Ala Tyr Pro 422
```

FIG. 19 (Con't)

```
1267 AAT GTA AGT GCA AAA ATT GAT TAT GAT GAC GAA ATG GCT TAC AGT
GAA TCA CAA TTA ATT 1326
423  Asn Val Ser Ala Lys Ile Asp Tyr Asp Asp Glu Met Ala Tyr Ser
Glu Ser Gln Leu Ile 442

1327 GCA AAA TTT GGT ACT GCA TTT AAA GCT GTA AAT AAT AGT TTG AAT
GTA AAC TTC GGC GCA 1386
443  Ala Lys Phe Gly Thr Ala Phe Lys Ala Val Asn Asn Ser Leu Asn
Val Asn Phe Gly Ala  462

1387 ATC AGT GAA GGG AAA ATG CAA GAA GAA GTC ATT AGT TTT AAA CAA
ATT TAC TAT AAC GTG 1446
463  Ile Ser Glu Gly Lys Met Gln Glu Glu Val Ile Ser Phe Lys Gln
Ile Tyr Tyr Asn Val 482

1447 AAT GTT AAT GAA CCT ACA AGA CCT TCC AGA TTT TTC GGC AAA GCT
GTT ACT AAA GAG CAG 1506
483  Asn Val Asn Glu Pro Thr Arg Pro Ser Arg Phe Phe Gly Lys Ala
Val Thr Lys Glu Gln 502

1507 TTG CAA GCG CTT GGA GTA AAT GCA GAA AAT CCT CCT GCA TAT ATC
TCA AGT GTG GCA TAC 1566
503  Leu Gln Ala Leu Gly Val Asn Ala Glu Asn Pro Pro Ala Tyr Ile
Ser Ser Val Ala Tyr 522

1567 GGC CGT CAA GTT TAT TTG AAA TTA TCG ACT AAT TCC CAT AGT ACT
AAA GTA AAA GCT GCT 1626
523  Gly Arg Gln Val Tyr Leu Lys Leu Ser Thr Asn Ser His Ser Thr
Lys Val Lys Ala Ala 542

1627 TTT GAT GCT GCC GTA AGT GGG AAA TCT GTC TCA GGT GAT GTA GAA
TTA ACA AAT ATC ATC 1686
543  Phe Asp Ala Ala Val Ser Gly Lys Ser Val Ser Gly Asp Val Glu
Leu Thr Asn Ile Ile 562

1687 AAA AAT TCT TCC TTC AAA GCC GTA ATT TAC GGT GGT TCC GCA AAA
GAT GAA GTT CAA ATC 1746
563 Lys Asn Ser Ser Phe Lys Ala Val Ile Tyr Gly Gly Ser Ala Lys
Asp Glu Val Gln Ile 582

1747 ATC GAT GGC AAC CTC GGA GAC TTA CGA GAT ATT TTG AAA AAA GGT
GCT ACT TTT AAT CGA 1806
583  Ile Asp Gly Asn Leu Gly Asp Leu Arg Asp Ile Leu Lys Lys Gly
Ala Thr Phe Asn Arg 602

1807 GAA ACA CCA GGA GTT CCC ATT GCT TAT ACA ACA AAT TTC TTA AAA
GAC AAT GAA TTA GCT 1866
603 Glu Thr Pro Gly Val Pro Ile Ala Tyr Thr Thr Asn Phe Leu Lys
Asp Asn Glu Leu Ala 622
```

FIG. 19 (Con't)

1867 GTT ATT AAA AAC AAC TCA GAA TAT ATT GAA ACA ACT TCA AAA GCT
TAT ACA GAT GGA AAA 1926
623  Val Ile Lys Asn Asn Ser Glu Tyr Ile Glu Thr Thr Ser Lys Ala
Tyr Thr Asp Gly Lys  642

1927 ATT AAT ATT GAT CAC TCT GGA GGC TAC GTT GCT CAA TTC AAC ATC
TCT TGG GAT GAA ATA 1986
643  Ile Asn Ile Asp His Ser Gly Gly Tyr Val Ala Gln Phe Asn Ile
Ser Trp Asp Glu Ile  662

1987 AAT TAT GAT CCT GAA GGT AAC GAA ATT GTT CAA CAT AAA AAC TGG
AGC GAA AAC AAT AAA 2046
 663 Asn Tyr Asp Pro Glu Gly Asn Glu Ile Val Gln His Lys Asn Trp
Ser Glu Asn Asn Lys  682

2047 AGC AAG CTA GCT CAT TTC ACA TCG TCC ATC TAT TTG CCA GGT AAC
GCA AGA AAT ATT AAT 2106
683  Ser Lys Leu Ala His Phe Thr Ser Ser Ile Tyr Leu Pro Gly Asn
Ala Arg Asn Ile Asn  702

2107 GTT TAC GCC AAA GAA TGC ACT GGT TTA GCT TGG GAA TGG TGG AGA
ACG GTA ATT GAT GAC 2166
 703 Val Tyr Ala Lys Glu Cys Thr Gly Leu Ala Trp Glu Trp Trp Arg
Thr Val Ile Asp Asp  722

2167 CGG AAC TTA CCA CTT GTG AAA AAT AGA AAT ATC TCC ATC TGG GGC
ACT ACG CTT TAT CCG 2226
 723 Arg Asn Leu Pro Leu Val Lys Asn Arg Asn Ile Ser Ile Trp Gly
Thr Thr Leu Tyr Pro  742

2227  AAA TAT AGT AAT AGT GTA GAT AAT CCA ATC GAA GCG GCC GCA CTC
GAG 2274
 743  Lys Tyr Ser Asn Ser Val Asp Asn Pro Ile Glu Ala Ala Ala Leu
Glu 758
His6
2275  CAC CAC CAC CAC CAC CAC 2292
 759  His His His His His His  764

FIG. 19 (Con't)

scFvDIATHIS-1:IL-2
Pel B sequence leader
 1    ATG AAA TAC CTG CTG CCG ACG GCT GCT GCT GGT CTG CTG CTC CTC
GCT GCC CAG CCG GCG   60
 1    Met Lys Tyr Leu Leu Pro Thr Ala Ala Ala Gly Leu Leu Leu Leu
Ala Ala Gln Pro Ala   20

61   ATG GCC   66
21   Met Ala   22
VH

FIG. 20

```
67   ATG GCC GAG GTG CAG CTG GCG GAG TCT GGG GGA GGC TTG GTA CAG
CCT GGG GGG TCC CTG   126
23   Met Ala Glu Val Gln Leu Ala Glu Ser Gly Gly Gly Leu Val Gln
Pro Gly Gly Ser Leu   42

127   AGA CTC TCC TGT GCC GCC TCT GGA TTC ACC TTT AGC AGC GAT GCC
ATG AGC TGG GTC CGC   186
43   Arg Leu Ser Cys Ala Ala Ser Gly Phe Thr Phe Ser Ser Asp Ala
Met Ser Trp Val Arg   62

187   CAG GCT CCA GGG AAG GGG CTG GAG TGG GTC TCA GCT ATT AGT GGT
AGT GGT GGT AGC ACA   246
63   Gln Ala Pro Gly Lys Gly Leu Glu Trp Val Ser Ala Ile Ser Gly
Ser Gly Gly Ser Thr   82

247   TAC TAC GCA GAC TCC GTG AAG GGC CGG TTC ACC ATC TCC AGA GAC
AAT TCC AAG AAC ACG   306
83   Tyr Tyr Ala Asp Ser Val Lys Gly Arg Phe Thr Ile Ser Arg Asp
Asn Ser Lys Asn Thr   102

307   CTG TAT CTG CAA ATG AAC AGC CTG AGA GCC GAG GAC ACG GCC GTA
TAT TAC TGT GCG AAA   366
103   Leu Tyr Leu Gln Met Asn Ser Leu Arg Ala Glu Asp Thr Ala Val
Tyr Tyr Cys Ala Lys   122

367   AGT AAT GAG TTT CTT TTT GAC TAC TGG GGC CAG GGA ACT CTG GTC
ACC GTG TCG AGA   423
123   Ser Asn Glu Phe Leu Phe Asp Tyr Trp Gly Gln Gly Thr Leu Val
Thr Val Ser Arg   141

Linker:
424   GGT GGA GGC GGT TCA GGC GGA GGT GGC TCT GGC GGT GGC GGA TCG
468
142   Gly Gly Gly Gly Ser Gly Gly Gly Gly Ser Gly Gly Gly Gly Ser
156

VL
469   TCT GAG CTG ACT CAG GAC CCT GCT GTG TCT GTG GCC TTG GGA CAG
ACA GTC AGG ATC ACA   528
157   Ser Glu Leu Thr Gln Asp Pro Ala Val Ser Val Ala Leu Gly Gln
Thr Val Arg Ile Thr   176

529   TGC CAA GGA GAC AGC CTC AGA AGC TCT TAT GCA AGC TGG TAC CGG
CAG AGG CCA GGA CAG   588
177   Cys Gln Gly Asp Ser Leu Arg Ser Ser Tyr Ala Ser Trp Tyr Arg
Gln Arg Pro Gly Gln   196

589   GCC *CCT GTA CCT GTC ATC TAT GGT AAG AAC AAC *TGG CCC TCA GGG
ATC CCA GAC CGG TTC   648
197   Ala *Pro Val Pro Val Ile Tyr Gly Lys Asn Asn *Trp Pro Ser Gly
Ile Pro Asp Arg Phe   216
```

FIG. 20 (Con't)

```
649  TCT GGC TCC AGC TCA GGA AAC ACA GCT TCC TTG ACC ATC ACT GGG
GCT CAG GCG GAA GAT  708
217  Ser Gly Ser Ser Ser Gly Asn Thr Ala Ser Leu Thr Ile Thr Gly
Ala Gln Ala Glu Asp  236

709  GAG GCT GAC TAT TAC *TGT AAC TCC TCT TAT GCG TGG CTG CCC TAT
GTG GTA TTC GGC GGA 768
237  Glu Ala Asp Tyr Tyr *Cys Asn Ser Ser Tyr Ala Trp Leu Pro Tyr
Val Val Phe Gly Gly 256

769   GGG ACC AAG CTG ACC GTC CTA GGC GCG GCC GCA    801
257   Gly Thr Lys Leu Thr Val Leu Gly Ala Ala Ala    267
Linker
802  TCT TCC TCA TCG GGT AGT AGC TCT TCC GGC TCA TCG TCC AGC GGC
846
268  Ser Ser Ser Ser Gly Ser Ser Ser Ser Gly Ser Ser Ser Ser Gly
282
IL-2
847  GCA CCT ACT TCA AGT TCT ACA AAG AAA ACA CAG CTA CAA CTG GAG
CAT TTA CTG CTG GAT 906
283  Ala Pro Thr Ser Ser Ser Thr Lys Lys Thr Gln Leu Gln Leu Glu
His Leu Leu Leu Asp 302

907  TTA CAG ATG ATT TTG AAT GGA ATT AAT AAT TAC AAG AAT CCC AAA
CTC ACC AGG ATG CTC 966
303  Leu Gln Met Ile Leu Asn Gly Ile Asn Asn Tyr Lys Asn Pro Lys
Leu Thr Arg Met Leu 322

967  ACA TTT AAG TTT TAC ATG CCC AAG AAG GCC ACA GAA CTG AAA CAT
CTT CAG TGT CTA GAA 1026
323  Thr Phe Lys Phe Tyr Met Pro Lys Lys Ala Thr Glu Leu Lys His
Leu Gln Cys Leu Glu 342

1027 GAA GAA CTC AAA CCT CTG GAG GAA GTG CTA AAT TTA GCT CAA AGC
AAA AAC TTT CAC TTA 1086
343  Glu Glu Leu Lys Pro Leu Glu Glu Val Leu Asn Leu Ala Gln Ser
Lys Asn Phe His Leu 362

1087 AGA CCC AGG GAC TTA ATC AGC AAT ATC AAC GTA ATA GTT CTG GAA
CTA AAG GGA TCT GAA 1146
363  Arg Pro Arg Asp Leu Ile Ser Asn Ile Asn Val Ile Val Leu Glu
Leu Lys Gly Ser Glu 382

1147 ACA ACA TTC ATG TGT GAA TAT GCT GAT GAG ACA GCA ACC ATT GTA
GAA TTT CTG AAC AGA 1206
383  Thr Thr Phe Met Cys Glu Tyr Ala Asp Glu Thr Ala Thr Ile Val
Glu Phe Leu Asn Arg 402

1207  TGG ATT ACC TTT TGT CAA AGC ATC ATC TCA ACA CTG ACT GCG GCC
GCA CTC GAG  1260
```

FIG. 20 (Con't)

```
403    Trp Ile Thr Phe Cys Gln Ser Ile Ile Ser Thr Leu Thr Ala Ala
Ala Leu Glu    420
His6
1261   CAC CAC CAC CAC CAC CAC  1278
 421   His His His His His His  426
```

FIG. 20 (Con't)

SEQUENCE LISTING

```
<160> NUMBER OF SEQ ID NOS: 30

<210> SEQ ID NO 1
<211> LENGTH: 864
<212> TYPE: DNA
```

<213> ORGANISM: Artificial
<220> FEATURE:
<223> OTHER INFORMATION: synthetic human anti-carcinoembryonic antigen
      (CEA) monoclonal antibody recombinant single chain variable
      fragment (scFv) fusion protein having E. coli Pel B leader
      sequence (scFvDIATHIS-1)
<220> FEATURE:
<221> NAME/KEY: CDS
<222> LOCATION: (1)..(864)
<223> OTHER INFORMATION: scFvDIATHIS-1

<400> SEQUENCE: 1

```
atg aaa tac ctg ctg ccg acg gct gct gct ggt ctg ctg ctc ctc gct      48
Met Lys Tyr Leu Leu Pro Thr Ala Ala Ala Gly Leu Leu Leu Leu Ala
1               5                   10                  15 gcc cag ccg gcg atg gcc atg gcc gag gtg cag ctg gcg gag tct ggg      96
Ala Gln Pro Ala Met Ala Met Ala Glu Val Gln Leu Ala Glu Ser Gly
                20                  25                  30 gga ggc ttg gta cag cct ggg ggg tcc ctg aga ctc tcc tgt gcc gcc     144
Gly Gly Leu Val Gln Pro Gly Gly Ser Leu Arg Leu Ser Cys Ala Ala
            35                  40                  45 tct gga ttc acc ttt agc agc gat gcc atg agc tgg gtc cgc cag gct     192
Ser Gly Phe Thr Phe Ser Ser Asp Ala Met Ser Trp Val Arg Gln Ala
50                  55                  60 cca ggg aag ggg ctg gag tgg gtc tca gct att agt ggt agt ggt ggt     240
Pro Gly Lys Gly Leu Glu Trp Val Ser Ala Ile Ser Gly Ser Gly Gly
65                  70                  75                  80 agc aca tac tac gca gac tcc gtg aag ggc cgg ttc acc atc tcc aga     288
Ser Thr Tyr Tyr Ala Asp Ser Val Lys Gly Arg Phe Thr Ile Ser Arg
                85                  90                  95 gac aat tcc aag aac acg ctg tat ctg caa atg aac agc ctg aga gcc     336
Asp Asn Ser Lys Asn Thr Leu Tyr Leu Gln Met Asn Ser Leu Arg Ala
                100                 105                 110 gag gac acg gcc gta tat tac tgt gcg aaa agt aat gag ttt ctt ttt     384
Glu Asp Thr Ala Val Tyr Tyr Cys Ala Lys Ser Asn Glu Phe Leu Phe
            115                 120                 125 gac tac tgg ggc cag gga act ctg gtc acc gtc tcg aga ggt gga ggc     432
Asp Tyr Trp Gly Gln Gly Thr Leu Val Thr Val Ser Arg Gly Gly Gly
130                 135                 140 ggt tca ggc gga ggt ggc tct ggc ggt ggc gga tcg tct gag ctg act     480
Gly Ser Gly Gly Gly Gly Ser Gly Gly Gly Gly Ser Ser Glu Leu Thr
145                 150                 155                 160 cag gac cct gct gtg tct gtg gcc ttg gga cag aca gtc agg atc aca     528
Gln Asp Pro Ala Val Ser Val Ala Leu Gly Gln Thr Val Arg Ile Thr
                165                 170                 175 tgc caa gga gac agc ctc aga agc tct tat gca agc tgg tac cgg cag     576
Cys Gln Gly Asp Ser Leu Arg Ser Ser Tyr Ala Ser Trp Tyr Arg Gln
                180                 185                 190 agg cca gga cag gcc cct gta cct gtc atc tat ggt aag aac aac tgg     624
Arg Pro Gly Gln Ala Pro Val Pro Val Ile Tyr Gly Lys Asn Asn Trp
            195                 200                 205 ccc tca ggg atc cca gac cgg ttc tct ggc tcc agc tca gga aac aca     672
Pro Ser Gly Ile Pro Asp Arg Phe Ser Gly Ser Ser Ser Gly Asn Thr
        210                 215                 220 gct tcc ttg acc atc act ggg gct cag gcg gaa gat gag gct gac tat     720
Ala Ser Leu Thr Ile Thr Gly Ala Gln Ala Glu Asp Glu Ala Asp Tyr
225                 230                 235                 240 tac tgt aac tcc tct tat gcg tgg ctg ccc tat gtg gta ttc ggc gga     768
Tyr Cys Asn Ser Ser Tyr Ala Trp Leu Pro Tyr Val Val Phe Gly Gly
                245                 250                 255 ggg acc aag ctg acc gtc cta ggc gcg gcc gca gat gac gat tcc gac     816
Gly Thr Lys Leu Thr Val Leu Gly Ala Ala Ala Asp Asp Asp Ser Asp
```

```
                    260                 265                 270
gac gat gac tac aag gac gac gat gac aag cac cat cac cat cac cat       864
Asp Asp Asp Tyr Lys Asp Asp Asp Asp Lys His His His His His His
            275                 280                 285

<210> SEQ ID NO 2
<211> LENGTH: 288
<212> TYPE: PRT
<213> ORGANISM: Artificial
<220> FEATURE:
<223> OTHER INFORMATION: synthetic human anti-carcinoembryonic antigen
      (CEA) monoclonal antibody recombinant single chain variable
      fragment (scFv) fusion protein having E. coli Pel B leader
      sequence (scFvDIATHIS-1)

<400> SEQUENCE: 2
```

Met Lys Tyr Leu Leu Pro Thr Ala Ala Gly Leu Leu Leu Ala
1               5                   10                  15

Ala Gln Pro Ala Met Ala Met Ala Glu Val Gln Leu Ala Glu Ser Gly
                20                  25                  30

Gly Leu Val Gln Pro Gly Gly Ser Leu Arg Leu Ser Cys Ala Ala
            35                  40                  45

Ser Gly Phe Thr Phe Ser Ser Asp Ala Met Ser Trp Val Arg Gln Ala
    50                  55                  60

Pro Gly Lys Gly Leu Glu Trp Val Ser Ala Ile Ser Gly Ser Gly Gly
65                  70                  75                  80

Ser Thr Tyr Tyr Ala Asp Ser Val Lys Gly Arg Phe Thr Ile Ser Arg
                85                  90                  95

Asp Asn Ser Lys Asn Thr Leu Tyr Leu Gln Met Asn Ser Leu Arg Ala
                100                 105                 110

Glu Asp Thr Ala Val Tyr Tyr Cys Ala Lys Ser Asn Glu Phe Leu Phe
            115                 120                 125

Asp Tyr Trp Gly Gln Gly Thr Leu Val Thr Val Ser Arg Gly Gly Gly
    130                 135                 140

Gly Ser Gly Gly Gly Gly Ser Gly Gly Gly Gly Ser Ser Glu Leu Thr
145                 150                 155                 160

Gln Asp Pro Ala Val Ser Val Ala Leu Gly Gln Thr Val Arg Ile Thr
                165                 170                 175

Cys Gln Gly Asp Ser Leu Arg Ser Ser Tyr Ala Ser Trp Tyr Arg Gln
            180                 185                 190

Arg Pro Gly Gln Ala Pro Val Pro Val Ile Tyr Gly Lys Asn Asn Trp
    195                 200                 205

Pro Ser Gly Ile Pro Asp Arg Phe Ser Gly Ser Ser Ser Gly Asn Thr
210                 215                 220

Ala Ser Leu Thr Ile Thr Gly Ala Gln Ala Glu Asp Glu Ala Asp Tyr
225                 230                 235                 240

Tyr Cys Asn Ser Ser Tyr Ala Trp Leu Pro Tyr Val Val Phe Gly Gly
                245                 250                 255

Gly Thr Lys Leu Thr Val Leu Gly Ala Ala Asp Asp Asp Ser Asp
            260                 265                 270

Asp Asp Asp Tyr Lys Asp Asp Asp Asp Lys His His His His His His
    275                 280                 285

```
<210> SEQ ID NO 3
<211> LENGTH: 22
<212> TYPE: DNA
<213> ORGANISM: Artificial
<220> FEATURE:
```

```
<223> OTHER INFORMATION: synthetic scFv amplification degenerated
      forward primer aCEANcoI5'

<400> SEQUENCE: 3
ccagccggcc atggccgagg tg                                              22

<210> SEQ ID NO 4
<211> LENGTH: 30
<212> TYPE: DNA
<213> ORGANISM: Artificial
<220> FEATURE:
<223> OTHER INFORMATION: synthetic scFv amplification degenerated
      reverse primer CEA EcoRI3'

<400> SEQUENCE: 4
acaaccatat gcagtctaat ggtgatggtg                                      30

<210> SEQ ID NO 5
<211> LENGTH: 27
<212> TYPE: DNA
<213> ORGANISM: Artificial
<220> FEATURE:
<223> OTHER INFORMATION: synthetic human ubiquitin PCR amplification
      forward primer Ub WT NotI5'

<400> SEQUENCE: 5
gaaggagcgg ccgctatgca gatcttc                                         27

<210> SEQ ID NO 6
<211> LENGTH: 29
<212> TYPE: DNA
<213> ORGANISM: Artificial
<220> FEATURE:
<223> OTHER INFORMATION: synthetic human ubiquitin PCR amplification
      reverse primer UbWTNotI3'

<400> SEQUENCE: 6
caagaatgcg gccgcacctc ttagtctta                                       29

<210> SEQ ID NO 7
<211> LENGTH: 70
<212> TYPE: DNA
<213> ORGANISM: Artificial
<220> FEATURE:
<223> OTHER INFORMATION: synthetic HIV-1 Vpr PCR amplification forward
      primer VPRNotI+link5'

<400> SEQUENCE: 7
ttccgcgtgc ggccgcatct tcctcatcgg gtagtagctc ttccggcatg gaacaagccc     60
cagaagacca                                                            70

<210> SEQ ID NO 8
<211> LENGTH: 36
<212> TYPE: DNA
<213> ORGANISM: Artificial
<220> FEATURE:
<223> OTHER INFORMATION: synthetic HIV-1 Vpr PCR amplification reverse
      primer VPRNotI3'

<400> SEQUENCE: 8
attcccgggg cggccgcgga tctactggct ccattt                               36

<210> SEQ ID NO 9
<211> LENGTH: 26
<212> TYPE: DNA
<213> ORGANISM: Artificial
```

```
<220> FEATURE:
<223> OTHER INFORMATION: synthetic yeast cytosine deaminase (YCD) PCR
      amplification forward primer LinYCD NotI 5'

<400> SEQUENCE: 9
ctaggcgcgg ccgcttccca tcgggt                                          26

<210> SEQ ID NO 10
<211> LENGTH: 27
<212> TYPE: DNA
<213> ORGANISM: Artificial
<220> FEATURE:
<223> OTHER INFORMATION: synthetic yeast cytosine deaminase (YCD) PCR
      amplification reverse primer YCD NotI3'

<400> SEQUENCE: 10
ggctgcgcgg ccgcctcagg aatatct                                         27

<210> SEQ ID NO 11
<211> LENGTH: 72
<212> TYPE: DNA
<213> ORGANISM: Artificial
<220> FEATURE:
<223> OTHER INFORMATION: synthetic listeriolysin-O (LLO) depleted of the
      PEST degradation signal PCR amplification forward primer
      LLONotI+link5'

<400> SEQUENCE: 11
tgaccgtcct aggctcttcc tcatcgggta gtagctcttc cggctcatcg tccagcggct      60
ccatggaaat cg                                                         72

<210> SEQ ID NO 12
<211> LENGTH: 31
<212> TYPE: DNA
<213> ORGANISM: Artificial
<220> FEATURE:
<223> OTHER INFORMATION: synthetic listeriolysin-O (LLO) depleted of the
      PEST degradation signal PCR amplification reverse primer LLONotI3'

<400> SEQUENCE: 12
atcgaagcgg ccgcagctag catgactggt g                                    31

<210> SEQ ID NO 13
<211> LENGTH: 35
<212> TYPE: DNA
<213> ORGANISM: Artificial
<220> FEATURE:
<223> OTHER INFORMATION: synthetic interleukin 2 (IL-2) PCR
      amplification forward primer Lin-IL2 NotI 5'

<400> SEQUENCE: 13
ctgaccgcgg ccgcctcttc ctcatcgggt agtag                                35

<210> SEQ ID NO 14
<211> LENGTH: 33
<212> TYPE: DNA
<213> ORGANISM: Artificial
<220> FEATURE:
<223> OTHER INFORMATION: synthetic interleukin 2 (IL-2) PCR
      amplification reverse primer IL2-NotI 3'

<400> SEQUENCE: 14
agactcggcg gccgcagtca gtgttgagat gat                                  33

<210> SEQ ID NO 15
<211> LENGTH: 5
```

```
<212> TYPE: PRT
<213> ORGANISM: Artificial
<220> FEATURE:
<223> OTHER INFORMATION: synthetic linker monomer between V-H and V-L
      portions of scFv

<400> SEQUENCE: 15

Gly Gly Gly Gly Ser
1               5

<210> SEQ ID NO 16
<211> LENGTH: 6
<212> TYPE: PRT
<213> ORGANISM: Artificial
<220> FEATURE:
<223> OTHER INFORMATION: synthetic His6 tag, 6xHis tag

<400> SEQUENCE: 16

His His His His His His
1               5

<210> SEQ ID NO 17
<211> LENGTH: 5
<212> TYPE: PRT
<213> ORGANISM: Artificial
<220> FEATURE:
<223> OTHER INFORMATION: synthetic linker monomer between effector and
      scFv

<400> SEQUENCE: 17

Ser Ser Ser Ser Gly
1               5

<210> SEQ ID NO 18
<211> LENGTH: 288
<212> TYPE: PRT
<213> ORGANISM: Artificial
<220> FEATURE:
<223> OTHER INFORMATION: synthetic human anti-carcinoembryonic antigen
      (CEA) monoclonal antibody recombinant single chain variable
      fragment (scFv) fusion protein having E. coli Pel B leader
      sequence (scFvDIATHIS-1)

<400> SEQUENCE: 18

Met Lys Tyr Leu Leu Pro Thr Ala Ala Ala Gly Leu Leu Leu Leu Ala
1               5                   10                  15

Ala Gln Pro Ala Met Ala Met Ala Glu Val Gln Leu Ala Glu Ser Gly
                20                  25                  30

Gly Gly Leu Val Gln Pro Gly Gly Ser Leu Arg Leu Ser Cys Ala Ala
            35                  40                  45

Ser Gly Phe Thr Phe Ser Ser Asp Ala Met Ser Trp Val Arg Gln Ala
        50                  55                  60

Pro Gly Lys Gly Leu Glu Trp Val Ser Ala Ile Ser Gly Ser Gly Gly
65                  70                  75                  80

Ser Thr Tyr Tyr Ala Asp Ser Val Lys Gly Arg Phe Thr Ile Ser Arg
                85                  90                  95

Asp Asn Ser Lys Asn Thr Leu Tyr Leu Gln Met Asn Ser Leu Arg Ala
            100                 105                 110

Glu Asp Thr Ala Val Tyr Tyr Cys Ala Lys Ser Asn Glu Phe Leu Phe
        115                 120                 125

Asp Tyr Tyr Trp Gly Gln Gly Thr Leu Val Thr Val Ser Arg Gly Gly
    130                 135                 140

Gly Gly Ser Gly Gly Gly Gly Ser Gly Gly Gly Gly Ser Ser Glu Leu
```

```
                    145                 150                 155                 160
Thr Gln Asp Pro Ala Val Ser Val Ala Leu Gly Gln Thr Val Arg Ile
                165                 170                 175

Thr Cys Gln Gly Asp Ser Leu Arg Ser Ser Tyr Ala Ser Trp Tyr Arg
                180                 185                 190

Gln Arg Pro Gly Gln Ala Pro Val Pro Val Ile Tyr Gly Lys Asn Asn
            195                 200                 205

Trp Pro Ser Gly Ile Pro Asp Arg Phe Ser Gly Ser Ser Ser Gly Asn
        210                 215                 220

Thr Ala Ser Leu Thr Ile Thr Gly Ala Gln Ala Glu Asp Glu Ala Asp
225                 230                 235                 240

Tyr Tyr Cys Asn Ser Ser Tyr Ala Trp Leu Pro Tyr Val Val Phe Gly
                245                 250                 255

Gly Gly Thr Lys Leu Thr Val Leu Gly Ala Ala Ala Asp Asp Asp Ser
            260                 265                 270

Asp Asp Asp Tyr Lys Asp Asp Asp Lys His His His His His His
        275                 280                 285

<210> SEQ ID NO 19
<211> LENGTH: 10
<212> TYPE: PRT
<213> ORGANISM: Artificial
<220> FEATURE:
<223> OTHER INFORMATION: synthetic linker at 5' terminus of HIV-1 Vpr
      in scFv DIATHI

```
                Ala Gln Pro Ala Met Ala Met Ala Glu Val Gln Leu Ala Glu Ser Gly
                            20                  25                  30 gga ggc ttg gta cag cct ggg ggg tcc ctg aga ctc tcc tgt gcc gcc         144
Gly Gly Leu Val Gln Pro Gly Gly Ser Leu Arg Leu Ser Cys Ala Ala
        35                  40                  45 tct gga ttc acc ttt agc agc gat gcc atg agc tgg gtc cgc cag gct         192
Ser Gly Phe Thr Phe Ser Ser Asp Ala Met Ser Trp Val Arg Gln Ala
50                  55                  60 cca ggg aag ggg ctg gag tgg gtc tca gct att agt ggt agt ggt ggt         240
Pro Gly Lys Gly Leu Glu Trp Val Ser Ala Ile Ser Gly Ser Gly Gly
65                  70                  75                  80 agc aca tac tac gca gac tcc gtg aag ggc cgg ttc acc atc tcc aga         288
Ser Thr Tyr Tyr Ala Asp Ser Val Lys Gly Arg Phe Thr Ile Ser Arg
            85                  90                  95 gac aat tcc aag aac acg ctg tat ctg caa atg aac agc ctg aga gcc         336
Asp Asn Ser Lys Asn Thr Leu Tyr Leu Gln Met Asn Ser Leu Arg Ala
            100                 105                 110 gag gac acg gcc gta tat tac tgt gcg aaa agt aat gag ttt ctt ttt         384
Glu Asp Thr Ala Val Tyr Tyr Cys Ala Lys Ser Asn Glu Phe Leu Phe
        115                 120                 125 gac tac tgg ggc cag gga act ctg gtc acc gtg tcg aga ggt gga ggc         432
Asp Tyr Trp Gly Gln Gly Thr Leu Val Thr Val Ser Arg Gly Gly Gly
130                 135                 140 ggt tca ggc gga ggt ggc tct ggc ggt ggc gga tcg tct gag ctg act         480
Gly Ser Gly Gly Gly Gly Ser Gly Gly Gly Gly Ser Ser Glu Leu Thr
145                 150                 155                 160 cag gac cct gct gtg tct gtg gcc ttg gga cag aca gtc agg atc aca         528
Gln Asp Pro Ala Val Ser Val Ala Leu Gly Gln Thr Val Arg Ile Thr
            165                 170                 175 tgc caa gga gac agc ctc aga agc tct tat gca agc tgg tac cgg cag         576
Cys Gln Gly Asp Ser Leu Arg Ser Ser Tyr Ala Ser Trp Tyr Arg Gln
            180                 185                 190 agg cca gga cag gcc cct gta cct gtc atc tat ggt aag aac aac tgg         624
Arg Pro Gly Gln Ala Pro Val Pro Val Ile Tyr Gly Lys Asn Asn Trp
        195                 200                 205 ccc tca ggg atc cca gac cgg ttc tct ggc tcc agc tca gga aac aca         672
Pro Ser Gly Ile Pro Asp Arg Phe Ser Gly Ser Ser Ser Gly Asn Thr
210                 215                 220 gct tcc ttg acc atc act ggg gct cag gcg gaa gat gag gct gac tat         720
Ala Ser Leu Thr Ile Thr Gly Ala Gln Ala Glu Asp Glu Ala Asp Tyr
225                 230                 235                 240 tac tgt aac tcc tct tat gcg tgg ctg ccc tat gtg gta ttc ggc gga         768
Tyr Cys Asn Ser Ser Tyr Ala Trp Leu Pro Tyr Val Val Phe Gly Gly
            245                 250                 255 ggg acc aag ctg acc gtc cta ggc gcg gcc gca atg cag atc ttc gtc         816
Gly Thr Lys Leu Thr Val Leu Gly Ala Ala Ala Met Gln Ile Phe Val
        260                 265                 270 aag acg tta acc ggt aaa acc ata act cta gaa gtt gaa cca tcc gat         864
Lys Thr Leu Thr Gly Lys Thr Ile Thr Leu Glu Val Glu Pro Ser Asp
275                 280                 285 acc atc gaa aac gtt aag gct aaa att caa gac aag gaa ggc att cca         912
Thr Ile Glu Asn Val Lys Ala Lys Ile Gln Asp Lys Glu Gly Ile Pro
        290                 295                 300 cct gat caa caa aga ttg atc ttt gcc ggt aag cag ctc gag gac ggt         960
Pro Asp Gln Gln Arg Leu Ile Phe Ala Gly Lys Gln Leu Glu Asp Gly
305                 310                 315                 320 aga acg ctg tct gat tac aac att cag aag gag tcg acc tta cat ctt        1008
Arg Thr Leu Ser Asp Tyr Asn Ile Gln Lys Glu Ser Thr Leu His Leu
            325                 330                 335
```

```
gtc tta aga cta aga ggt gcg gcc gca ctc gag cac cac cac cac cac      1056
Val Leu Arg Leu Arg Gly Ala Ala Ala Leu Glu His His His His His
                340                 345                 350 cac                                                                   1059
His

<210> SEQ ID NO 22
<211> LENGTH: 353
<212> TYPE: PRT
<213> ORGANISM: Artificial
<220> FEATURE:
<223> OTHER INFORMATION: synthetic human anti-carcinoembryonic antigen
      (CEA) monoclonal antibody recombinant single chain variable
      fragment (scFv) fusion protein having E. coli Pel B leader
      sequence (scFvDIATHIS-1) with human ubiquitin insert at C-terminus
      (scFvDIATHIS-1:Ubiquitin)

<400> SEQUENCE: 22

Met Lys Tyr Leu Leu Pro Thr Ala Ala Ala Gly Leu Leu Leu Ala
1               5                   10                  15

Ala Gln Pro Ala Met Ala Met Ala Glu Val Gln Leu Ala Glu Ser Gly
                20                  25                  30

Gly Gly Leu Val Gln Pro Gly Gly Ser Leu Arg Leu Ser Cys Ala Ala
            35                  40                  45

Ser Gly Phe Thr Phe Ser Ser Asp Ala Met Ser Trp Val Arg Gln Ala
    50                  55                  60

Pro Gly Lys Gly Leu Glu Trp Val Ser Ala Ile Ser Gly Ser Gly Gly
65              70                  75                  80

Ser Thr Tyr Tyr Ala Asp Ser Val Lys Gly Arg Phe Thr Ile Ser Arg
                85                  90                  95

Asp Asn Ser Lys Asn Thr Leu Tyr Leu Gln Met Asn Ser Leu Arg Ala
                100                 105                 110

Glu Asp Thr Ala Val Tyr Tyr Cys Ala Lys Ser Asn Glu Phe Leu Phe
            115                 120                 125

Asp Tyr Trp Gly Gln Gly Thr Leu Val Thr Val Ser Arg Gly Gly Gly
    130                 135                 140

Gly Ser Gly Gly Gly Gly Ser Gly Gly Gly Gly Ser Ser Glu Leu Thr
145                 150                 155                 160

Gln Asp Pro Ala Val Ser Val Ala Leu Gly Gln Thr Val Arg Ile Thr
                165                 170                 175

Cys Gln Gly Asp Ser Leu Arg Ser Ser Tyr Ala Ser Trp Tyr Arg Gln
            180                 185                 190

Arg Pro Gly Gln Ala Pro Val Pro Val Ile Tyr Gly Lys Asn Asn Trp
    195                 200                 205

Pro Ser Gly Ile Pro Asp Arg Phe Ser Gly Ser Ser Ser Gly Asn Thr
    210                 215                 220

Ala Ser Leu Thr Ile Thr Gly Ala Gln Ala Glu Asp Glu Ala Asp Tyr
225                 230                 235                 240

Tyr Cys Asn Ser Ser Tyr Ala Trp Leu Pro Tyr Val Val Phe Gly Gly
                245                 250                 255

Gly Thr Lys Leu Thr Val Leu Gly Ala Ala Ala Met Gln Ile Phe Val
            260                 265                 270

Lys Thr Leu Thr Gly Lys Thr Ile Thr Leu Glu Val Glu Pro Ser Asp
    275                 280                 285

Thr Ile Glu Asn Val Lys Ala Lys Ile Gln Asp Lys Glu Gly Ile Pro
    290                 295                 300

Pro Asp Gln Gln Arg Leu Ile Phe Ala Gly Lys Gln Leu Glu Asp Gly
```

```
                    305                 310                 315                 320
Arg Thr Leu Ser Asp Tyr Asn Ile Gln Lys Glu Ser Thr Leu His Leu
                325                 330                 335

Val Leu Arg Leu Arg Gly Ala Ala Ala Leu Glu His His His His His
                340                 345                 350

His

<210> SEQ ID NO 23
<211> LENGTH: 1152
<212> TYPE: DNA
<213> ORGANISM: Artificial
<220> FEATURE:
<223> OTHER INFORMATION: scFvDIATHIS-1:HIV-1 vpr
<220> FEATURE:
<223> OTHER INFORMATION: synthetic human anti-carcinoembryonic antigen
      (CEA) monoclonal antibody recombinant single chain variable
      fragment (scFv) fusion protein having E. coli

```
Arg Pro Gly Gln Ala Pro Val Pro Val Ile Tyr Gly Lys Asn Asn Trp
        195                 200                 205 ccc tca ggg atc cca gac cgg ttc tct ggc tcc agc tca gga aac aca        672
Pro Ser Gly Ile Pro Asp Arg Phe Ser Gly Ser Ser Ser Gly Asn Thr
210                 215                 220 gct tcc ttg acc atc act ggg gct cag gcg gaa gat gag gct gac tat        720
Ala Ser Leu Thr Ile Thr Gly Ala Gln Ala Glu Asp Glu Ala Asp Tyr
225                 230                 235                 240 tac tgt aac tcc tct tat gcg tgg ctg ccc tat gtg gta ttc ggc gga        768
Tyr Cys Asn Ser Ser Tyr Ala Trp Leu Pro Tyr Val Val Phe Gly Gly
                245                 250                 255 ggg acc aag ctg acc gtc cta ggc gcg gcc gca tct tcc tca tcg ggt        816
Gly Thr Lys Leu Thr Val Leu Gly Ala Ala Ala Ser Ser Ser Ser Gly
            260                 265                 270 agt agc tct tcc ggc atg gaa caa gcc cca gaa gac caa ggg cca cag        864
Ser Ser Ser Ser Gly Met Glu Gln Ala Pro Glu Asp Gln Gly Pro Gln
        275                 280                 285 agg gag cca cac aat gaa tgg aca cta gag ctt tta gag gag ctt aag        912
Arg Glu Pro His Asn Glu Trp Thr Leu Glu Leu Leu Glu Glu Leu Lys
    290                 295                 300 aat gaa gct gtt aga cat ttt cct agg att tgg ctc cat ggc tta ggg        960
Asn Glu Ala Val Arg His Phe Pro Arg Ile Trp Leu His Gly Leu Gly
305                 310                 315                 320 caa cat atc tat gaa act tat ggg gat act tgg gca gga gtg gaa gcc       1008
Gln His Ile Tyr Glu Thr Tyr Gly Asp Thr Trp Ala Gly Val Glu Ala
                325                 330                 335 ata ata aga att ctg caa caa ctg ctg ttt atc cat ttc aga att ggg       1056
Ile Ile Arg Ile Leu Gln Gln Leu Leu Phe Ile His Phe Arg Ile Gly
            340                 345                 350 tgt cga cat agc aga ata ggc gtt act caa cag agg aga gca aga aat       1104
Cys Arg His Ser Arg Ile Gly Val Thr Gln Gln Arg Arg Ala Arg Asn
        355                 360                 365 gga gcc agt aga tcc gcg gcc gca ctc gag cac cac cac cac cac cac       1152
Gly Ala Ser Arg Ser Ala Ala Ala Leu Glu His His His His His His
    370                 375                 380

<210> SEQ ID NO 24
<211> LENGTH: 384
<212> TYPE: PRT
<213> ORGANISM: Artificial
<220> FEATURE:
<223> OTHER INFORMATION: synthetic human anti-carcinoembryonic antigen
      (CEA) monoclonal antibody recombinant single chain variable
      fragment (scFv) fusion protein having E. coli Pel B leader
      sequence (scFvDIATHIS-1) with HIV-1 Vpr insert at C-terminus
      (scFvDIATHIS-1:HIV-1 vpr)

<400> SEQUENCE: 24

Met Lys Tyr Leu Leu Pro Thr Ala Ala Ala Gly Leu Leu Leu Leu Ala
1               5                   10                  15

Ala Gln Pro Ala Met Ala Met Ala Glu Val Gln Leu Ala Glu Ser Gly
            20                  25                  30

Gly Gly Leu Val Gln Pro Gly Gly Ser Leu Arg Leu Ser Cys Ala Ala
        35                  40                  45

Ser Gly Phe Thr Phe Ser Ser Asp Ala Met Ser Trp Val Arg Gln Ala
    50                  55                  60

Pro Gly Lys Gly Leu Glu Trp Val Ser Ala Ile Ser Gly Ser Gly Gly
65                  70                  75                  80

Ser Thr Tyr Tyr Ala Asp Ser Val Lys Gly Arg Phe Thr Ile Ser Arg
                85                  90                  95
```

```
Asp Asn Ser Lys Asn Thr Leu Tyr Leu Gln Met Asn Ser Leu Arg Ala
                100                 105                 110

Glu Asp Thr Ala Val Tyr Tyr Cys Ala Lys Ser Asn Glu Phe Leu Phe
            115                 120                 125

Asp Tyr Trp Gly Gln Gly Thr Leu Val Thr Val Ser Arg Gly Gly Gly
        130                 135                 140

Gly Ser Gly Gly Gly Ser Gly Gly Gly Ser Ser Glu Leu Thr
145             150                 155                 160

Gln Asp Pro Ala Val Ser Val Ala Leu Gly Gln Thr Val Arg Ile Thr
                165                 170                 175

Cys Gln Gly Asp Ser Leu Arg Ser Ser Tyr Ala Ser Trp Tyr Arg Gln
            180                 185                 190

Arg Pro Gly Gln Ala Pro Val Pro Val Ile Tyr Gly Lys Asn Asn Trp
        195                 200                 205

Pro Ser Gly Ile Pro Asp Arg Phe Ser Gly Ser Ser Ser Gly Asn Thr
210                 215                 220

Ala Ser Leu Thr Ile Thr Gly Ala Gln Ala Glu Asp Glu Ala Asp Tyr
225                 230                 235                 240

Tyr Cys Asn Ser Ser Tyr Ala Trp Leu Pro Tyr Val Val Phe Gly Gly
            245                 250                 255

Gly Thr Lys Leu Thr Val Leu Gly Ala Ala Ala Ser Ser Ser Ser Gly
        260                 265                 270

Ser Ser Ser Ser Gly Met Glu Gln Ala Pro Glu Asp Gln Gly Pro Gln
    275                 280                 285

Arg Glu Pro His Asn Glu Trp Thr Leu Glu Leu Leu Glu Glu Leu Lys
290                 295                 300

Asn Glu Ala Val Arg His Phe Pro Arg Ile Trp Leu His Gly Leu Gly
305                 310                 315                 320

Gln His Ile Tyr Glu Thr Tyr Gly Asp Thr Trp Ala Gly Val Glu Ala
            325                 330                 335

Ile Ile Arg Ile Leu Gln Gln Leu Leu Phe Ile His Phe Arg Ile Gly
        340                 345                 350

Cys Arg His Ser Arg Ile Gly Val Thr Gln Gln Arg Arg Ala Arg Asn
    355                 360                 365

Gly Ala Ser Arg Ser Ala Ala Ala Leu Glu His His His His His His
370                 375                 380
```

<210> SEQ ID NO 25
<211> LENGTH: 1353
<212> TYPE: DNA
<213> ORGANISM: Artificial
<220> FEATURE:
<223> OTHER INFORMATION: scFvDIATHIS-1:Yeast Cytosine Deaminase (YCD)
<220> FEATURE:
<223> OTHER INFORMATION: synthetic human anti-carcinoembryonic antigen
    (CEA) monoclonal antibody recombinant single chain variable
    fragment (scFv) fusion protein having E. coli Pel B leader
    sequence (scFvDIATHIS-1) with yeast cytosine deaminase insert at
    C-terminus (scFvDIATHIS-1:YCD)
<220> FEATURE:
<221> NAME/KEY: CDS
<222> LOCATION: (1)..(1353)
<223> OTHER INFORMATION: scFvDIATHIS-1:Yeast Cytosine Deaminase (YCD)

<400> SEQUENCE: 25

```
atg aaa tac ctg ctg ccg acg gct gct gct ggt ctg ctc ctc gct      48
Met Lys Tyr Leu Leu Pro Thr Ala Ala Ala Gly Leu Leu Leu Leu Ala
1               5                   10                  15 gcc cag ccg gcg atg gcc atg gcc gag gtg cag ctg gcg gag tct ggg  96
```

|   |   |   |   |   |   |   |   |   |   |   |   |   |   |   |   |
|---|---|---|---|---|---|---|---|---|---|---|---|---|---|---|---|
| Ala | Gln | Pro | Ala | Met | Ala | Met | Ala | Glu | Val | Gln | Leu | Ala | Glu | Ser | Gly |
|   |   |   | 20 |   |   |   | 25 |   |   |   |   | 30 |   |   |   |

```
gga ggc ttg gta cag cct ggg ggg tcc ctg aga ctc tcc tgt gcc gcc       144
Gly Gly Leu Val Gln Pro Gly Gly Ser Leu Arg Leu Ser Cys Ala Ala
            35                  40                  45 tct gga ttc acc ttt agc agc gat gcc atg agc tgg gtc cgc cag gct       192
Ser Gly Phe Thr Phe Ser Ser Asp Ala Met Ser Trp Val Arg Gln Ala
 50                  55                  60 cca ggg aag ggg ctg gag tgg gtc tca gct att agt ggt agt ggt ggt       240
Pro Gly Lys Gly Leu Glu Trp Val Ser Ala Ile Ser Gly Ser Gly Gly
 65                  70                  75                  80 agc aca tac tac gca gac tcc gtg aag ggc cgg ttc acc atc tcc aga       288
Ser Thr Tyr Tyr Ala Asp Ser Val Lys Gly Arg Phe Thr Ile Ser Arg
                 85                  90                  95 gac aat tcc aag aac acg ctg tat ctg caa atg aac agc ctg aga gcc       336
Asp Asn Ser Lys Asn Thr Leu Tyr Leu Gln Met Asn Ser Leu Arg Ala
             100                 105                 110 gag gac acg gcc gta tat tac tgt gcg aaa agt aat gag ttt ctt ttt       384
Glu Asp Thr Ala Val Tyr Tyr Cys Ala Lys Ser Asn Glu Phe Leu Phe
         115                 120                 125 gac tac tgg ggc cag gga act ctg gtc acc gtg tcg aga ggt gga ggc       432
Asp Tyr Trp Gly Gln Gly Thr Leu Val Thr Val Ser Arg Gly Gly Gly
 130                 135                 140 ggt tca ggc gga ggt ggc tct ggc ggt ggc gga tcg tct gag ctg act       480
Gly Ser Gly Gly Gly Gly Ser Gly Gly Gly Gly Ser Ser Glu Leu Thr
145                 150                 155                 160 cag gac cct gct gtg tct gtg gcc ttg gga cag aca gtc agg atc aca       528
Gln Asp Pro Ala Val Ser Val Ala Leu Gly Gln Thr Val Arg Ile Thr
                 165                 170                 175 tgc caa gga gac agc ctc aga agc tct tat gca agc tgg tac cgg cag       576
Cys Gln Gly Asp Ser Leu Arg Ser Ser Tyr Ala Ser Trp Tyr Arg Gln
             180                 185                 190 agg cca gga cag gcc cct gta cct gtc atc tat ggt aag aac aac tgg       624
Arg Pro Gly Gln Ala Pro Val Pro Val Ile Tyr Gly Lys Asn Asn Trp
         195                 200                 205 ccc tca ggg atc cca gac cgg ttc tct ggc tcc agc tca gga aac aca       672
Pro Ser Gly Ile Pro Asp Arg Phe Ser Gly Ser Ser Ser Gly Asn Thr
 210                 215                 220 gct tcc ttg acc atc act ggg gct cag gcg gaa gat gag gct gac tat       720
Ala Ser Leu Thr Ile Thr Gly Ala Gln Ala Glu Asp Glu Ala Asp Tyr
225                 230                 235                 240 tac tgt aac tcc tct tat gcg tgg ctg ccc tat gtg gta ttc ggc gga       768
Tyr Cys Asn Ser Ser Tyr Ala Trp Leu Pro Tyr Val Val Phe Gly Gly
                 245                 250                 255 ggg acc aag ctg acc gtc cta ggc gcg gcc gca tct tcc tca tcg ggt       816
Gly Thr Lys Leu Thr Val Leu Gly Ala Ala Ala Ser Ser Ser Ser Gly
             260                 265                 270 agt agc tct tcc ggc tca tcg tcc agc ggc atg gtg aca ggg gga atg       864
Ser Ser Ser Ser Gly Ser Ser Ser Ser Gly Met Val Thr Gly Gly Met
         275                 280                 285 gca agc aag tgg gat cag aaa ggc atg gac att gcc tat gaa gag gcc       912
Ala Ser Lys Trp Asp Gln Lys Gly Met Asp Ile Ala Tyr Glu Glu Ala
 290                 295                 300 gca ctg ggc tac aaa gaa ggc ggt gtg ccg att ggc ggt tgt ctg atc       960
Ala Leu Gly Tyr Lys Glu Gly Gly Val Pro Ile Gly Gly Cys Leu Ile
305                 310                 315                 320 aat aac aaa gac ggc tcc gtg ctg ggc cgt ggg cac aac atg cgc ttc      1008
Asn Asn Lys Asp Gly Ser Val Leu Gly Arg Gly His Asn Met Arg Phe
                 325                 330                 335
```

```
cag aaa ggc agc gcc acc ctg cac ggc gaa atc tcc acc ctg gaa aac    1056
Gln Lys Gly Ser Ala Thr Leu His Gly Glu Ile Ser Thr Leu Glu Asn
            340                 345                 350 tgc ggg cgt ctc gag ggc aaa gtg tac aaa gat acc acc ctg tat acg    1104
Cys Gly Arg Leu Glu Gly Lys Val Tyr Lys Asp Thr Thr Leu Tyr Thr
        355                 360                 365 acc ctg agc ccg tgc gac atg tgt acg ggc gcc atc atc atg tac ggc    1152
Thr Leu Ser Pro Cys Asp Met Cys Thr Gly Ala Ile Ile Met Tyr Gly
370                 375                 380 att cca cgc tgc gtg gtc ggc gaa aac gtg aat ttc aaa tcc aag ggc    1200
Ile Pro Arg Cys Val Val Gly Glu Asn Val Asn Phe Lys Ser Lys Gly
385                 390                 395                 400 gag aaa tac ctg cag acc cgc ggc cac gaa gtg gtc gtg gtg gac gat    1248
Glu Lys Tyr Leu Gln Thr Arg Gly His Glu Val Val Val Val Asp Asp
            405                 410                 415 gaa cgc tgc aaa aag atc atg aaa cag ttc atc gat gag cgt cca cag    1296
Glu Arg Cys Lys Lys Ile Met Lys Gln Phe Ile Asp Glu Arg Pro Gln
        420                 425                 430 gat tgg ttt gaa gat att cct gag gcg gcc gca ctc gag cac cac cac    1344
Asp Trp Phe Glu Asp Ile Pro Glu Ala Ala Ala Leu Glu His His His
    435                 440                 445 cac cac cac                                                         1353
His His His
    450

<210> SEQ ID NO 26
<211> LENGTH: 451
<212> TYPE: PRT
<213> ORGANISM: Artificial
<220> FEATURE:
<223> OTHER INFORMATION: synthetic human anti-carcinoembryonic antigen
      (CEA) monoclonal antibody recombinant single chain variable
      fragment (scFv) fusion protein having E. coli Pel B leader
      sequence (scFvDIATHIS-1) with yeast cytosine deaminase insert at
      C-terminus (scFvDIATHIS-1:YCD)

<400> SEQUENCE: 26

Met Lys Tyr Leu Leu Pro Thr Ala Ala Ala Gly Leu Leu Leu Leu Ala
1               5                   10                  15

Ala Gln Pro Ala Met Ala Met Ala Glu Val Gln Leu Ala Glu Ser Gly
            20                  25                  30

Gly Gly Leu Val Gln Pro Gly Gly Ser Leu Arg Leu Ser Cys Ala Ala
        35                  40                  45

Ser Gly Phe Thr Phe Ser Ser Asp Ala Met Ser Trp Val Arg Gln Ala
    50                  55                  60

Pro Gly Lys Gly Leu Glu Trp Val Ser Ala Ile Ser Gly Ser Gly Gly
65                  70                  75                  80

Ser Thr Tyr Tyr Ala Asp Ser Val Lys Gly Arg Phe Thr Ile Ser Arg
                85                  90                  95

Asp Asn Ser Lys Asn Thr Leu Tyr Leu Gln Met Asn Ser Leu Arg Ala
            100                 105                 110

Glu Asp Thr Ala Val Tyr Tyr Cys Ala Lys Ser Asn Glu Phe Leu Phe
        115                 120                 125

Asp Tyr Trp Gly Gln Gly Thr Leu Val Thr Val Ser Arg Gly Gly Gly
    130                 135                 140

Gly Ser Gly Gly Gly Gly Ser Gly Gly Gly Gly Ser Ser Glu Leu Thr
145                 150                 155                 160

Gln Asp Pro Ala Val Ser Val Ala Leu Gly Gln Thr Val Arg Ile Thr
                165                 170                 175
```

Cys Gln Gly Asp Ser Leu Arg Ser Ser Tyr Ala Ser Trp Tyr Arg Gln
            180                 185                 190

Arg Pro Gly Gln Ala Pro Val Pro Val Ile Tyr Gly Lys Asn Asn Trp
        195                 200                 205

Pro Ser Gly Ile Pro Asp Arg Phe Ser Gly Ser Ser Ser Gly Asn Thr
    210                 215                 220

Ala Ser Leu Thr Ile Thr Gly Ala Gln Ala Glu Asp Glu Ala Asp Tyr
225                 230                 235                 240

Tyr Cys Asn Ser Ser Tyr Ala Trp Leu Pro Tyr Val Val Phe Gly Gly
                245                 250                 255

Gly Thr Lys Leu Thr Val Leu Gly Ala Ala Ala Ser Ser Ser Ser Gly
            260                 265                 270

Ser Ser Ser Ser Gly Ser Ser Ser Gly Met Val Thr Gly Gly Met
        275                 280                 285

Ala Ser Lys Trp Asp Gln Lys Gly Met Asp Ile Ala Tyr Glu Glu Ala
        290                 295                 300

Ala Leu Gly Tyr Lys Glu Gly Val Pro Ile Gly Gly Cys Leu Ile
305                 310                 315                 320

Asn Asn Lys Asp Gly Ser Val Leu Gly Arg Gly His Asn Met Arg Phe
                325                 330                 335

Gln Lys Gly Ser Ala Thr Leu His Gly Glu Ile Ser Thr Leu Glu Asn
            340                 345                 350

Cys Gly Arg Leu Glu Gly Lys Val Tyr Lys Asp Thr Thr Leu Tyr Thr
                355                 360                 365

Thr Leu Ser Pro Cys Asp Met Cys Thr Gly Ala Ile Ile Met Tyr Gly
        370                 375                 380

Ile Pro Arg Cys Val Val Gly Glu Asn Val Asn Phe Lys Ser Lys Gly
385                 390                 395                 400

Glu Lys Tyr Leu Gln Thr Arg Gly His Glu Val Val Val Asp Asp
                405                 410                 415

Glu Arg Cys Lys Lys Ile Met Lys Gln Phe Ile Asp Glu Arg Pro Gln
            420                 425                 430

Asp Trp Phe Glu Asp Ile Pro Glu Ala Ala Ala Leu Glu His His His
        435                 440                 445

His His His
    450

<210> SEQ ID NO 27
<211> LENGTH: 2292
<212> TYPE: DNA
<213> ORGANISM: Artificial
<220> FEATURE:
<223> OTHER INFORMATION: scFvDIATHIS-1:Listeriolysin (LLO) delta PEST
<220> FEATURE:
<223> OTHER INFORMATION: synthetic human anti-carcinoembryonic antigen
      (CEA) monoclonal antibody recombinant single chain variable
      fragment (scFv) fusion protein having E. coli Pel B leader
      sequence (scFvDIATHIS-1) with listeriolysin-O (LLO) delta PEST
      insert at C-terminus
<220> FEATURE:
<221> NAME/KEY: CDS
<222> LOCATION: (1)..(2292)
<223> OTHER INFORMATION: scFvDIATHIS-1:Listeriolysin (LLO) delta PEST,
      scFvDIATHIS-1:LLOdeltaPEST

<400> SEQUENCE: 27 atg aaa tac ctg ctg ccg acg gct gct gct ggt ctg ctg ctc ctc gct    48
Met Lys Tyr Leu Leu Pro Thr Ala Ala Ala Gly Leu Leu Leu Leu Ala
1               5                   10                  15

| | | |
|---|---|---|
| gcc cag ccg gcg atg gcc atg gcc gag gtg cag ctg gcg gag tct ggg<br>Ala Gln Pro Ala Met Ala Met Ala Glu Val Gln Leu Ala Glu Ser Gly<br>     20                  25                 30 | | 96 |
| gga ggc ttg gta cag cct ggg ggg tcc ctg aga ctc tcc tgt gcc gcc<br>Gly Gly Leu Val Gln Pro Gly Gly Ser Leu Arg Leu Ser Cys Ala Ala<br>         35                  40                45 | | 144 |
| tct gga ttc acc ttt agc agc gat gcc atg agc tgg gtc cgc cag gct<br>Ser Gly Phe Thr Phe Ser Ser Asp Ala Met Ser Trp Val Arg Gln Ala<br>50                  55                60 | | 192 |
| cca ggg aag ggg ctg gag tgg gtc tca gct att agt ggt agt ggt ggt<br>Pro Gly Lys Gly Leu Glu Trp Val Ser Ala Ile Ser Gly Ser Gly Gly<br>65                  70              75              80 | | 240 |
| agc aca tac tac gca gac tcc gtg aag ggc cgg ttc acc atc tcc aga<br>Ser Thr Tyr Tyr Ala Asp Ser Val Lys Gly Arg Phe Thr Ile Ser Arg<br>               85                90              95 | | 288 |
| gac aat tcc aag aac acg ctg tat ctg caa atg aac agc ctg aga gcc<br>Asp Asn Ser Lys Asn Thr Leu Tyr Leu Gln Met Asn Ser Leu Arg Ala<br>            100                105             110 | | 336 |
| gag gac acg gcc gta tat tac tgt gcg aaa agt aat gag ttt ctt ttt<br>Glu Asp Thr Ala Val Tyr Tyr Cys Ala Lys Ser Asn Glu Phe Leu Phe<br>        115                120             125 | | 384 |
| gac tac tgg ggc cag gga act ctg gtc acc gtg tcg aga ggt gga ggc<br>Asp Tyr Trp Gly Gln Gly Thr Leu Val Thr Val Ser Arg Gly Gly Gly<br>130                 135                140 | | 432 |
| ggt tca ggc gga ggt ggc tct ggc ggt ggc gga tcg tct gag ctg act<br>Gly Ser Gly Gly Gly Gly Ser Gly Gly Gly Gly Ser Ser Glu Leu Thr<br>145                 150                155              160 | | 480 |
| cag gac cct gct gtg tct gtg gcc ttg gga cag aca gtc agg atc aca<br>Gln Asp Pro Ala Val Ser Val Ala Leu Gly Gln Thr Val Arg Ile Thr<br>                  165             170              175 | | 528 |
| tgc caa gga gac agc ctc aga agc tct tat gca agc tgg tac cgg cag<br>Cys Gln Gly Asp Ser Leu Arg Ser Ser Tyr Ala Ser Trp Tyr Arg Gln<br>                180                185             190 | | 576 |
| agg cca gga cag gcc cct gta cct gtc atc tat ggt aag aac aac tgg<br>Arg Pro Gly Gln Ala Pro Val Pro Val Ile Tyr Gly Lys Asn Asn Trp<br>195                 200                205 | | 624 |
| ccc tca ggg atc cca gac cgg ttc tct ggc tcc agc tca gga aac aca<br>Pro Ser Gly Ile Pro Asp Arg Phe Ser Gly Ser Ser Ser Gly Asn Thr<br>210                 215                220 | | 672 |
| gct tcc ttg acc atc act ggg gct cag gcg gaa gat gag gct gac tat<br>Ala Ser Leu Thr Ile Thr Gly Ala Gln Ala Glu Asp Glu Ala Asp Tyr<br>225                 230                235              240 | | 720 |
| tac tgt aac tcc tct tat gcg tgg ctg ccc tat gtg gta ttc ggc gga<br>Tyr Cys Asn Ser Ser Tyr Ala Trp Leu Pro Tyr Val Val Phe Gly Gly<br>                  245             250              255 | | 768 |
| ggg acc aag ctg acc gtc cta ggc gcg gcc gca tct tcc tca tcg ggt<br>Gly Thr Lys Leu Thr Val Leu Gly Ala Ala Ala Ser Ser Ser Ser Gly<br>                  260             265              270 | | 816 |
| agt agc tct tcc ggc tca tcg tcc agc ggc atg gaa atc gat aag tat<br>Ser Ser Ser Ser Gly Ser Ser Ser Ser Gly Met Glu Ile Asp Lys Tyr<br>275                 280                285 | | 864 |
| ata caa gga ttg gat tac aat aaa aac aat gta tta gta tac cac gga<br>Ile Gln Gly Leu Asp Tyr Asn Lys Asn Asn Val Leu Val Tyr His Gly<br>290                 295                300 | | 912 |
| gat gca gtg aca aat gtg ccg cca aga aaa ggt tac aaa gat gga aat<br>Asp Ala Val Thr Asn Val Pro Pro Arg Lys Gly Tyr Lys Asp Gly Asn<br>305                 310                315              320 | | 960 |
| gaa tat atc gtt gtg gag aaa aag aag aaa tcc atc aat caa aat aat<br>Glu Tyr Ile Val Val Glu Lys Lys Lys Lys Ser Ile Asn Gln Asn Asn<br>                  325             330              335 | | 1008 |

```
                                                       -continued gca gac atc caa gtt gta aat gca att tcg agc cta aca tat cca ggt    1056
Ala Asp Ile Gln Val Val Asn Ala Ile Ser Ser Leu Thr Tyr Pro Gly
            340                 345                 350 gct ctc gta aaa gcg aat tcg gaa tta gta gaa aat caa cca gat gtt    1104
Ala Leu Val Lys Ala Asn Ser Glu Leu Val Glu Asn Gln Pro Asp Val
355                 360                 365 ctc cct gta aaa cgt gat tca tta aca ctt agc atc gat ttg cca gga    1152
Leu Pro Val Lys Arg Asp Ser Leu Thr Leu Ser Ile Asp Leu Pro Gly
    370                 375                 380 atg act aat caa gac aat aaa atc gtt gta aaa aat gct act aaa tcg    1200
Met Thr Asn Gln Asp Asn Lys Ile Val Val Lys Asn Ala Thr Lys Ser
385                 390                 395                 400 aat gtt aac aac gca gta aat aca tta gtg gaa aga tgg aat gaa aaa    1248
Asn Val Asn Asn Ala Val Asn Thr Leu Val Glu Arg Trp Asn Glu Lys
                405                 410                 415 tat gct caa gct tat ccg aat gta agt gca aaa att gat tat gat gac    1296
Tyr Ala Gln Ala Tyr Pro Asn Val Ser Ala Lys Ile Asp Tyr Asp Asp
            420                 425                 430 gaa atg gct tac agt gaa tca caa tta att gca aaa ttt ggt act gca    1344
Glu Met Ala Tyr Ser Glu Ser Gln Leu Ile Ala Lys Phe Gly Thr Ala
        435                 440                 445 ttt aaa gct gta aat aat agt ttg aat gta aac ttc ggc gca atc agt    1392
Phe Lys Ala Val Asn Asn Ser Leu Asn Val Asn Phe Gly Ala Ile Ser
450                 455                 460 gaa ggg aaa atg caa gaa gaa gtc att agt ttt aaa caa att tac tat    1440
Glu Gly Lys Met Gln Glu Glu Val Ile Ser Phe Lys Gln Ile Tyr Tyr
465                 470                 475                 480 aac gtg aat gtt aat gaa cct aca aga cct tcc aga ttt ttc ggc aaa    1488
Asn Val Asn Val Asn Glu Pro Thr Arg Pro Ser Arg Phe Phe Gly Lys
                485                 490                 495 gct gtt act aaa gag cag ttg caa gcg ctt gga gta aat gca gaa aat    1536
Ala Val Thr Lys Glu Gln Leu Gln Ala Leu Gly Val Asn Ala Glu Asn
            500                 505                 510 cct cct gca tat atc tca agt gtg gca tac ggc cgt caa gtt tat ttg    1584
Pro Pro Ala Tyr Ile Ser Ser Val Ala Tyr Gly Arg Gln Val Tyr Leu
        515                 520                 525 aaa tta tcg act aat tcc cat agt act aaa gta aaa gct gct ttt gat    1632
Lys Leu Ser Thr Asn Ser His Ser Thr Lys Val Lys Ala Ala Phe Asp
530                 535                 540 gct gcc gta agt ggg aaa tct gtc tca ggt gat gta gaa tta aca aat    1680
Ala Ala Val Ser Gly Lys Ser Val Ser Gly Asp Val Glu Leu Thr Asn
545                 550                 555                 560 atc atc aaa aat tct tcc ttc aaa gcc gta att tac ggt ggt tcc gca    1728
Ile Ile Lys Asn Ser Ser Phe Lys Ala Val Ile Tyr Gly Gly Ser Ala
                565                 570                 575 aaa gat gaa gtt caa atc atc gat ggc aac ctc gga gac tta cga gat    1776
Lys Asp Glu Val Gln Ile Ile Asp Gly Asn Leu Gly Asp Leu Arg Asp
            580                 585                 590 att ttg aaa aaa ggt gct act ttt aat cga gaa aca cca gga gtt ccc    1824
Ile Leu Lys Lys Gly Ala Thr Phe Asn Arg Glu Thr Pro Gly Val Pro
        595                 600                 605 att gct tat aca aca aat ttc tta aaa gac aat gaa tta gct gtt att    1872
Ile Ala Tyr Thr Thr Asn Phe Leu Lys Asp Asn Glu Leu Ala Val Ile
610                 615                 620 aaa aac aac tca gaa tat att gaa aca act tca aaa gct tat aca gat    1920
Lys Asn Asn Ser Glu Tyr Ile Glu Thr Thr Ser Lys Ala Tyr Thr Asp
625                 630                 635                 640 gga aaa att aat att gat cac tct gga ggc tac gtt gct caa ttc aac    1968
Gly Lys Ile Asn Ile Asp His Ser Gly Gly Tyr Val Ala Gln Phe Asn
```

```
atc tct tgg gat gaa ata aat tat gat cct gaa ggt aac gaa att gtt      2016
Ile Ser Trp Asp Glu Ile Asn Tyr Asp Pro Glu Gly Asn Glu Ile Val
        660                 665                 670 caa cat aaa aac tgg agc gaa aac aat aaa agc aag cta gct cat ttc      2064
Gln His Lys Asn Trp Ser Glu Asn Asn Lys Ser Lys Leu Ala His Phe
            675                 680                 685 aca tcg tcc atc tat ttg cca ggt aac gca aga aat att aat gtt tac      2112
Thr Ser Ser Ile Tyr Leu Pro Gly Asn Ala Arg Asn Ile Asn Val Tyr
    690                 695                 700 gcc aaa gaa tgc act ggt tta gct tgg gaa tgg tgg aga acg gta att      2160
Ala Lys Glu Cys Thr Gly Leu Ala Trp Glu Trp Trp Arg Thr Val Ile
705                 710                 715                 720 gat gac cgg aac tta cca ctt gtg aaa aat aga aat atc tcc atc tgg      2208
Asp Asp Arg Asn Leu Pro Leu Val Lys Asn Arg Asn Ile Ser Ile Trp
                725                 730                 735 ggc act acg ctt tat ccg aaa tat agt aat agt gta gat aat cca atc      2256
Gly Thr Thr Leu Tyr Pro Lys Tyr Ser Asn Ser Val Asp Asn Pro Ile
            740                 745                 750 gaa gcg gcc gca ctc gag cac cac cac cac cac cac                      2292
Glu Ala Ala Ala Leu Glu His His His His His His
        755                 760
```

<210> SEQ ID NO 28
<211> LENGTH: 764
<212> TYPE: PRT
<213> ORGANISM: Artificial
<220> FEATURE:
<223> OTHER INFORMATION: synthetic human anti-carcinoembryonic antigen
    (CEA) monoclonal antibody recombinant single chain variable
    fragment (scFv) fusion protein having E. coli Pel B leader
    sequence (scFvDIATHIS-1) with listeriolysin-O (LLO) delta PEST
    insert at C-terminus

<400> SEQUENCE: 28

```
Met Lys Tyr Leu Leu Pro Thr Ala Ala Ala Gly Leu Leu Leu Leu Ala
1               5                   10                  15

Ala Gln Pro Ala Met Ala Met Ala Glu Val Gln Leu Ala Glu Ser Gly
            20                  25                  30

Gly Gly Leu Val Gln Pro Gly Gly Ser Leu Arg Leu Ser Cys Ala Ala
        35                  40                  45

Ser Gly Phe Thr Phe Ser Ser Asp Ala Met Ser Trp Val Arg Gln Ala
    50                  55                  60

Pro Gly Lys Gly Leu Glu Trp Val Ser Ala Ile Ser Gly Ser Gly Gly
65                  70                  75                  80

Ser Thr Tyr Tyr Ala Asp Ser Val Lys Gly Arg Phe Thr Ile Ser Arg
                85                  90                  95

Asp Asn Ser Lys Asn Thr Leu Tyr Leu Gln Met Asn Ser Leu Arg Ala
            100                 105                 110

Glu Asp Thr Ala Val Tyr Tyr Cys Ala Lys Ser Asn Glu Phe Leu Phe
        115                 120                 125

Asp Tyr Trp Gly Gln Gly Thr Leu Val Thr Val Ser Arg Gly Gly Gly
    130                 135                 140

Gly Ser Gly Gly Gly Gly Ser Gly Gly Gly Gly Ser Ser Glu Leu Thr
145                 150                 155                 160

Gln Asp Pro Ala Val Ser Val Ala Leu Gly Gln Thr Val Arg Ile Thr
                165                 170                 175

Cys Gln Gly Asp Ser Leu Arg Ser Ser Tyr Ala Ser Trp Tyr Arg Gln
            180                 185                 190
```

```
Arg Pro Gly Gln Ala Pro Val Pro Val Ile Tyr Gly Lys Asn Asn Trp
        195                 200                 205

Pro Ser Gly Ile Pro Asp Arg Phe Ser Gly Ser Ser Ser Gly Asn Thr
210                 215                 220

Ala Ser Leu Thr Ile Thr Gly Ala Gln Ala Glu Asp Glu Ala Asp Tyr
225                 230                 235                 240

Tyr Cys Asn Ser Ser Tyr Ala Trp Leu Pro Tyr Val Val Phe Gly Gly
                245                 250                 255

Gly Thr Lys Leu Thr Val Leu Gly Ala Ala Ser Ser Ser Ser Ser Gly
                260                 265                 270

Ser Ser Ser Ser Gly Ser Ser Ser Gly Met Glu Ile Asp Lys Tyr
        275                 280                 285

Ile Gln Gly Leu Asp Tyr Asn Lys Asn Val Leu Val Tyr His Gly
        290                 295                 300

Asp Ala Val Thr Asn Val Pro Pro Arg Lys Gly Tyr Lys Asp Gly Asn
305                 310                 315                 320

Glu Tyr Ile Val Val Glu Lys Lys Lys Ser Ile Asn Gln Asn Asn
                325                 330                 335

Ala Asp Ile Gln Val Val Asn Ala Ile Ser Ser Leu Thr Tyr Pro Gly
        340                 345                 350

Ala Leu Val Lys Ala Asn Ser Glu Leu Val Glu Asn Gln Pro Asp Val
        355                 360                 365

Leu Pro Val Lys Arg Asp Ser Leu Thr Leu Ser Ile Asp Leu Pro Gly
        370                 375                 380

Met Thr Asn Gln Asp Asn Lys Ile Val Val Lys Asn Ala Thr Lys Ser
385                 390                 395                 400

Asn Val Asn Asn Ala Val Asn Thr Leu Val Glu Arg Trp Asn Glu Lys
                405                 410                 415

Tyr Ala Gln Ala Tyr Pro Asn Val Ser Ala Lys Ile Asp Tyr Asp Asp
        420                 425                 430

Glu Met Ala Tyr Ser Glu Ser Gln Leu Ile Ala Lys Phe Gly Thr Ala
        435                 440                 445

Phe Lys Ala Val Asn Asn Ser Leu Asn Val Asn Phe Gly Ala Ile Ser
450                 455                 460

Glu Gly Lys Met Gln Glu Glu Val Ile Ser Phe Lys Gln Ile Tyr Tyr
465                 470                 475                 480

Asn Val Asn Val Asn Glu Pro Thr Arg Pro Ser Arg Phe Phe Gly Lys
                485                 490                 495

Ala Val Thr Lys Glu Gln Leu Gln Ala Leu Gly Val Asn Ala Glu Asn
                500                 505                 510

Pro Pro Ala Tyr Ile Ser Ser Val Ala Tyr Gly Arg Gln Val Tyr Leu
        515                 520                 525

Lys Leu Ser Thr Asn Ser His Ser Thr Lys Val Lys Ala Ala Phe Asp
        530                 535                 540

Ala Ala Val Ser Gly Lys Ser Val Ser Gly Asp Val Glu Leu Thr Asn
545                 550                 555                 560

Ile Ile Lys Asn Ser Ser Phe Lys Ala Val Ile Tyr Gly Gly Ser Ala
                565                 570                 575

Lys Asp Glu Val Gln Ile Ile Asp Gly Asn Leu Gly Asp Leu Arg Asp
                580                 585                 590

Ile Leu Lys Lys Gly Ala Thr Phe Asn Arg Glu Thr Pro Gly Val Pro
        595                 600                 605
```

```
Ile Ala Tyr Thr Thr Asn Phe Leu Lys Asp Asn Glu Leu Ala Val Ile
    610                 615                 620

Lys Asn Asn Ser Glu Tyr Ile Glu Thr Thr Ser Lys Ala Tyr Thr Asp
625                 630                 635                 640

Gly Lys Ile Asn Ile Asp His Ser Gly Gly Tyr Val Ala Gln Phe Asn
                645                 650                 655

Ile Ser Trp Asp Glu Ile Asn Tyr Asp Pro Glu Gly Asn Glu Ile Val
            660                 665                 670

Gln His Lys Asn Trp Ser Glu Asn Lys Ser Lys Leu Ala His Phe
        675                 680                 685

Thr Ser Ser Ile Tyr Leu Pro Gly Asn Ala Arg Asn Ile Asn Val Tyr
690                 695                 700

Ala Lys Glu Cys Thr Gly Leu Ala Trp Glu Trp Trp Arg Thr Val Ile
705                 710                 715                 720

Asp Asp Arg Asn Leu Pro Leu Val Lys Asn Arg Asn Ile Ser Ile Trp
                725                 730                 735

Gly Thr Thr Leu Tyr Pro Lys Tyr Ser Asn Ser Val Asp Asn Pro Ile
                740                 745                 750

Glu Ala Ala Ala Leu Glu His His His His His His
            755                 760
```

```
<210> SEQ ID NO 29
<211> LENGTH: 1278
<212> TYPE: DNA
<213> ORGANISM: Artificial
<220> FEATURE:
<223> OTHER INFORMATION: synthetic human anti-carcinoembryonic antigen
      (CEA) monoclonal antibody recombinant single chain variable
      fragment (scFv) fusion protein having E. coli Pel B leader
      sequence (scFvDIATHIS-1) with interleukin 2 insert at C-terminus
      (scFvDIATHIS-1:IL-2)
<220> FEATURE:
<221> NAME/KEY: CDS
<222> LOCATION: (1)..(1278)
<223> OTHER INFORMATION: scFvDIATHIS-1:Interleukin 2 (IL-2)

<400> SEQUENCE: 29
```

```
atg aaa tac ctg ctg ccg acg gct gct gct ggt ctg ctg ctc ctc gct    48
Met Lys Tyr Leu Leu Pro Thr Ala Ala Ala Gly Leu Leu Leu Leu Ala
1               5                   10                  15 gcc cag ccg gcg atg gcc atg gcc gag gtg cag ctg gcg gag tct ggg    96
Ala Gln Pro Ala Met Ala Met Ala Glu Val Gln Leu Ala Glu Ser Gly
                20                  25                  30 gga ggc ttg gta cag cct ggg ggg tcc ctg aga ctc tcc tgt gcc gcc   144
Gly Gly Leu Val Gln Pro Gly Gly Ser Leu Arg Leu Ser Cys Ala Ala
            35                  40                  45 tct gga ttc acc ttt agc agc gat gcc atg agc tgg gtc cgc cag gct   192
Ser Gly Phe Thr Phe Ser Ser Asp Ala Met Ser Trp Val Arg Gln Ala
50                  55                  60 cca ggg aag ggg ctg gag tgg gtc tca gct att agt ggt agt ggt ggt   240
Pro Gly Lys Gly Leu Glu Trp Val Ser Ala Ile Ser Gly Ser Gly Gly
65                  70                  75                  80 agc aca tac tac gca gac tcc gtg aag ggc cgg ttc acc atc tcc aga   288
Ser Thr Tyr Tyr Ala Asp Ser Val Lys Gly Arg Phe Thr Ile Ser Arg
                85                  90                  95 gac aat tcc aag aac acg ctg tat ctg caa atg aac agc ctg aga gcc   336
Asp Asn Ser Lys Asn Thr Leu Tyr Leu Gln Met Asn Ser Leu Arg Ala
            100                 105                 110 gag gac acg gcc gta tat tac tgt gcg aaa agt aat gag ttt ctt ttt   384
Glu Asp Thr Ala Val Tyr Tyr Cys Ala Lys Ser Asn Glu Phe Leu Phe
        115                 120                 125
```

-continued

```
gac tac tgg ggc cag gga act ctg gtc acc gtg tcg aga ggt gga ggc      432
Asp Tyr Trp Gly Gln Gly Thr Leu Val Thr Val Ser Arg Gly Gly Gly
    130                 135                 140 ggt tca ggc gga ggt ggc tct ggc ggt ggc gga tcg tct gag ctg act      480
Gly Ser Gly Gly Gly Gly Ser Gly Gly Gly Gly Ser Ser Glu Leu Thr
145                 150                 155                 160 cag gac cct gct gtg tct gtg gcc ttg gga cag aca gtc agg atc aca      528
Gln Asp Pro Ala Val Ser Val Ala Leu Gly Gln Thr Val Arg Ile Thr
                165                 170                 175 tgc caa gga gac agc ctc aga agc tct tat gca agc tgg tac cgg cag      576
Cys Gln Gly Asp Ser Leu Arg Ser Ser Tyr Ala Ser Trp Tyr Arg Gln
            180                 185                 190 agg cca gga cag gcc cct gta cct gtc atc tat ggt aag aac aac tgg      624
Arg Pro Gly Gln Ala Pro Val Pro Val Ile Tyr Gly Lys Asn Asn Trp
        195                 200                 205 ccc tca ggg atc cca gac cgg ttc tct ggc tcc agc tca gga aac aca      672
Pro Ser Gly Ile Pro Asp Arg Phe Ser Gly Ser Ser Ser Gly Asn Thr
    210                 215                 220 gct tcc ttg acc atc act ggg gct cag gcg gaa gat gag gct gac tat      720
Ala Ser Leu Thr Ile Thr Gly Ala Gln Ala Glu Asp Glu Ala Asp Tyr
225                 230                 235                 240 tac tgt aac tcc tct tat gcg tgg ctg ccc tat gtg gta ttc ggc gga      768
Tyr Cys Asn Ser Ser Tyr Ala Trp Leu Pro Tyr Val Val Phe Gly Gly
                245                 250                 255 ggg acc aag ctg acc gtc cta ggc gcg gcc gca tct tcc tca tcg ggt      816
Gly Thr Lys Leu Thr Val Leu Gly Ala Ala Ala Ser Ser Ser Ser Gly
            260                 265                 270 agt agc tct tcc ggc tca tcg tcc agc ggc gca cct act tca agt tct      864
Ser Ser Ser Ser Gly Ser Ser Ser Ser Gly Ala Pro Thr Ser Ser Ser
        275                 280                 285 aca aag aaa aca cag cta caa ctg gag cat tta ctg ctg gat tta cag      912
Thr Lys Lys Thr Gln Leu Gln Leu Glu His Leu Leu Leu Asp Leu Gln
    290                 295                 300 atg att ttg aat gga att aat aat tac aag aat ccc aaa ctc acc agg      960
Met Ile Leu Asn Gly Ile Asn Asn Tyr Lys Asn Pro Lys Leu Thr Arg
305                 310                 315                 320 atg ctc aca ttt aag ttt tac atg ccc aag aag gcc aca gaa ctg aaa     1008
Met Leu Thr Phe Lys Phe Tyr Met Pro Lys Lys Ala Thr Glu Leu Lys
                325                 330                 335 cat ctt cag tgt cta gaa gaa gaa ctc aaa cct ctg gag gaa gtg cta     1056
His Leu Gln Cys Leu Glu Glu Glu Leu Lys Pro Leu Glu Glu Val Leu
            340                 345                 350 aat tta gct caa agc aaa aac ttt cac tta aga ccc agg gac tta atc     1104
Asn Leu Ala Gln Ser Lys Asn Phe His Leu Arg Pro Arg Asp Leu Ile
        355                 360                 365 agc aat atc aac gta ata gtt ctg gaa cta aag gga tct gaa aca aca     1152
Ser Asn Ile Asn Val Ile Val Leu Glu Leu Lys Gly Ser Glu Thr Thr
    370                 375                 380 ttc atg tgt gaa tat gct gat gag aca gca acc att gta gaa ttt ctg     1200
Phe Met Cys Glu Tyr Ala Asp Glu Thr Ala Thr Ile Val Glu Phe Leu
385                 390                 395                 400 aac aga tgg att acc ttt tgt caa agc atc atc tca aca ctg act gcg     1248
Asn Arg Trp Ile Thr Phe Cys Gln Ser Ile Ile Ser Thr Leu Thr Ala
                405                 410                 415 gcc gca ctc gag cac cac cac cac cac cac                             1278
Ala Ala Leu Glu His His His His His His
            420                 425
```

<210> SEQ ID NO 30

<211> LENGTH: 426
<212> TYPE: PRT
<213> ORGANISM: Artificial
<220> FEATURE:
<223> OTHER INFORMATION: synthetic human anti-carcinoembryonic antigen
(CEA) monoclonal antibody recombinant single chain variable
fragment (scFv) fusion protein having E. coli Pel B leader
sequence (scFvDIATHIS-1) with interleukin 2 insert at C-terminus
(scFvDIATHIS-1:IL-2)

<400> SEQUENCE: 30

```
Met Lys Tyr Leu Leu Pro Thr Ala Ala Ala Gly Leu Leu Leu Leu Ala
1               5                   10                  15

Ala Gln Pro Ala Met Ala Met Ala Glu Val Gln Leu Ala Glu Ser Gly
            20                  25                  30

Gly Gly Leu Val Gln Pro Gly Gly Ser Leu Arg Leu Ser Cys Ala Ala
        35                  40                  45

Ser Gly Phe Thr Phe Ser Ser Asp Ala Met Ser Trp Val Arg Gln Ala
    50                  55                  60

Pro Gly Lys Gly Leu Glu Trp Val Ser Ala Ile Ser Gly Ser Gly Gly
65                  70                  75                  80

Ser Thr Tyr Tyr Ala Asp Ser Val Lys Gly Arg Phe Thr Ile Ser Arg
                85                  90                  95

Asp Asn Ser Lys Asn Thr Leu Tyr Leu Gln Met Asn Ser Leu Arg Ala
            100                 105                 110

Glu Asp Thr Ala Val Tyr Tyr Cys Ala Lys Ser Asn Glu Phe Leu Phe
        115                 120                 125

Asp Tyr Trp Gly Gln Gly Thr Leu Val Thr Val Ser Arg Gly Gly Gly
    130                 135                 140

Gly Ser Gly Gly Gly Gly Ser Gly Gly Gly Gly Ser Ser Glu Leu Thr
145                 150                 155                 160

Gln Asp Pro Ala Val Ser Val Ala Leu Gly Gln Thr Val Arg Ile Thr
                165                 170                 175

Cys Gln Gly Asp Ser Leu Arg Ser Ser Tyr Ala Ser Trp Tyr Arg Gln
            180                 185                 190

Arg Pro Gly Gln Ala Pro Val Pro Val Ile Tyr Gly Lys Asn Asn Trp
        195                 200                 205

Pro Ser Gly Ile Pro Asp Arg Phe Ser Gly Ser Ser Ser Gly Asn Thr
    210                 215                 220

Ala Ser Leu Thr Ile Thr Gly Ala Gln Ala Glu Asp Glu Ala Asp Tyr
225                 230                 235                 240

Tyr Cys Asn Ser Ser Tyr Ala Trp Leu Pro Tyr Val Val Phe Gly Gly
                245                 250                 255

Gly Thr Lys Leu Thr Val Leu Gly Ala Ala Ala Ser Ser Ser Ser Gly
            260                 265                 270

Ser Ser Ser Ser Gly Ser Ser Ser Gly Ala Pro Thr Ser Ser Ser
        275                 280                 285

Thr Lys Lys Thr Gln Leu Gln Leu Glu His Leu Leu Leu Asp Leu Gln
    290                 295                 300

Met Ile Leu Asn Gly Ile Asn Asn Tyr Lys Asn Pro Lys Leu Thr Arg
305                 310                 315                 320

Met Leu Thr Phe Lys Phe Tyr Met Pro Lys Lys Ala Thr Glu Leu Lys
                325                 330                 335

His Leu Gln Cys Leu Glu Glu Glu Leu Lys Pro Leu Glu Glu Val Leu
            340                 345                 350

Asn Leu Ala Gln Ser Lys Asn Phe His Leu Arg Pro Arg Asp Leu Ile
```

```
                    355                 360                 365
Ser Asn Ile Asn Val Ile Val Leu Glu Leu Lys Gly Ser Glu Thr Thr
        370                 375                 380

Phe Met Cys Glu Tyr Ala Asp Glu Thr Ala Thr Ile Val Glu Phe Leu
385                 390                 395                 400

Asn Arg Trp Ile Thr Phe Cys Gln Ser Ile Ile Ser Thr Leu Thr Ala
                405                 410                 415

Ala Ala Leu Glu His His His His His His
            420                 425
```

ANTIBODY DERIVATIVES

REFERENCE TO A "SEQUENCE LISTING," A TABLE, OR A COMPUTER PROGRAM LISTING APPENDIX SUBMITTED AS AN ASCII TEXT FILE

The Sequence Listing written in file 95195-860662.TXT, created on Mar. 27, 2013, 77,824 bytes, machine format IBM-PC, MS-Windows operating system, is hereby incorporated by reference in its entirety for all purposes.

The present invention relates to single chain variable fragment (scFv), to its mono- and oligomeric forms, and to processes for the production thereof.

Conventional pharmacological approaches for the therapy of tumours suffer from poor selectivity, thus compromising dose escalation to more therapeutically active levels. Therefore, the development of selective, and better tolerated, cancer therapeutics represents an important goal in the research of new and more effective treatment. One way to improve the selectivity of therapeutic molecules is to target the tumour site, thereby sparing normal tissues. Antibody-based cancer treatments offer a solution to this problem and have given promising results in several malignancies (4).

The widespread success of murine hybridoma technology has resulted in the discovery of numerous well characterised monoclonal antibodies (mAbs) with unique specificities. Many of these mAbs display considerable therapeutic potential by inhibiting cell proliferation or as vehicles for targeting radionuclides, cytotoxic agents and immunomodulators (5). A major breakthrough in the field of antibody engineering was the generation of antibody fragments as recombinant proteins in the periplasmic space of *Escherichia coli* (6).

Single-chain Fv's (ScFv) is the smallest antibody fragment that retains the binding properties of the parent antibody. They are structured as single polypeptide chains incorporating a heavy chain variable and a light chain variable region, linked by a polypeptide linker. Monoclonal antibodies in scFv format represent valuable molecules suitable for clinical applications such as targeted delivery of drugs, toxins or for tumour imaging. Compared to full length monoclonal antibody, they have better tumour penetration (7; 8; 9) without any significant toxicity, but have a rapid blood clearance (10). To slow down scFv clearance, these molecules can also be engineered to incorporate a carboxy terminal cysteine residue, thereby enabling formation of a (scFv)$_2$ fragment by virtue of disulphide bridging (11; 12). Another bivalent molecule is a "diabody" (13), which is formed from two scFvs linked noncovalently by a short linker. A further possibility is a "minibody," in which 2 scFv fragments are linked by a component of the heavy-chain region (for example, $CH_3$), resulting in a bivalent molecule (14) or by chemical crosslinking (15).

Carcinoembryonic antigen (CEA) is an attractive target for immunotherapeutic purposes because of its expression profile, its role in tumour progression, and its immunogenicity. CEA belongs to the CD66 immunoglobulin superfamily that also comprises CEACAM1, which has recently received considerable interest as a cancer antigen target (16). Preclinical studies in melanomas show that expression of the cell adhesion molecule, CEACAM1, is an independent factor of metastasis risk, with a predictive value superior to that of tumour thickness (17). In fact, CEACAM1 also appears to be a promising endothelial target for bladder cancer therapy; this molecule is involved in the switch from non-invasive and non-vascularised to invasive and vascularised bladder cancer (18). Furthermore, CEACAM1, which is not expressed in the lung, has been identified in carcinoma from this tissue (19).

During the past two decades, a number of mAbs to the extracellular domains of CEA and CEACAM1 have been produced and characterised. However, the selective delivery of bioactive components to tumour-expressing CEA cells using this class of antibodies presents several limitations, including the human anti-mouse antibody (HAMA) response (20). Hence the isolation of a CEA specific antibody is a first step toward the construction of new anticancer monoclonal antibodies designed for selectively delivering of bioactive agents.

Phage antibody technology may help to provide a solution, as human antibody fragments can be isolated from repertoires of fragments displayed on filamentous bacteriophage (21; 22). The process does not require immunisation of humans, and antibody fragments can be made against both foreign and human antigens. These immunocompetent fragments are secreted into the bacterial periplasm and culture medium and they can be produced in a large scale by using stable and safe prokaryotic cell systems (23).

The usefulness of phage antibody libraries as a tool for generating scFvs against tumour associated antigens has been widely used in the past 5 years and more than 50 human antibodies developed with this technique are under clinical evaluation for safety and efficacy in the treatment of cancers (24). The efficient display of recombinant antibodies on filamentous phage has also been explored by us, showing that soluble human scFvs selected from the ETH-2 library (25) may yield agents capable of specifically recognising metastatic melanoma, breast, colon and lung cancer cells (1).

Surprisingly, we have now found that an anti-CEA scFv having an uncleaved Pel B leader sequence is capable of forming oligomers, is stable and is highly specific for CEA and CEACAM1.

Thus, in a first aspect, the present invention provides a fusion protein comprising a single chain variable fragment (scFv) specific for CEA and CEACAM, and a leader sequence cleavable by *E. coli* Pel B peptidase.

In an alternative aspect, there is provided a fusion protein comprising a single chain variable fragment (scFv) specific for each of carcinoembryonic antigen (CEA) and CEA related Cell Adhesion Molecule1 (CEACAM1), and a leader sequence, said leader sequence comprising all, or substantially all, of the *E. coli* Pel B leader sequence, a linker sequence being optionally present between said leader sequence and said scFv.

The leader sequence is preferably as identified in amino acids 1-22 of SEQ ID NO: 2. A leader sequence that comprises substantially all of the Pel B leader sequence will retain the effect on scFv E8 when linked thereto, of encouraging the formation of oligomers, and will contain at least 18 of the 22 amino acids of the Pel B leader sequence, preferably 19, more preferably 20, yet more preferably 21, and particularly preferably all 22 of the amino acids shown for Pel B leader sequence of SEQ ID NO: 2.

CEACAM1 belongs to the CEA gene family that in turn belong to the immunoglobulin gene superfamily. CEA and CEACAM1 are encoded by two different genes, CEACAM5 and CEACAM1, respectively. As noted above, CEACAM1 has recently received considerable interest as a cancer antigen target, especially in melanoma and lung cancer. The preferred scFv, of DIATHIS1, derives from the known E8 scFv, which is specific for CEA and CEACAM1, in the accompanying Examples, we demonstrate the reactivity of scFv with CEACAM1-positive primary melanoma cell line MelP5.

The fusion proteins of the present invention have surprisingly good half lives, beating other known forms of scFv specific for CEA, such as diabodies and dimers, by some considerable margin. Further, they are highly specific for CEA, with the currently preferred fusion protein exhibiting a greater than 30% increase in affinity over scFvE8. Furthermore, the fusion proteins of the invention can deliver four times more radiolabel than the next best scFv.

Without being bound by theory, what appears to be responsible for this enhanced activity is the presence of the leader sequence, which seems to encourage the formation of oligomers of the scFv. Lower number oligomers seem to have both high affinity and good stability.

For the isolation of anti-CEA human mAbs in scFv format, we biopanned the human scFv ETH-2 phage antibody library on purified CEA protein as target antigen. The isolated anti-CEA antibody (1) was further engineered by adding a leader sequence (pel B) and 3 new mutations causing three amino acid changes. The thus obtained fusion protein had surprisingly high stability and, in vivo, proved to be a convenient pharmacokinetic with very high tumour targeting capacity. This new recombinant scFv was named DIATHIS-1 and meets several criteria for a biological compound to be used for diagnosis and therapy of cancer: it is human, hence poorly or not at all immunogenic, and it hinds selectively to the cell surface CEACAM1 epitope expressed exclusively on carcinoma cells, such as melanoma, lung and gastric carcinoma. In addition, the simple and flexible genetic structure of DIATHIS-1 permits the construction and isolation of oligomeric scFv fragments with an optimum balance between diffusion and retention.

A preferred fusion protein, DIATHIS-1, of the invention was obtained by DNA recombinant techniques starting from the antibody fragment scFvE8 specific for the carcinoembryonic antigen (CEA)(1). DIATHIS-1 differs from the original E8 by 3 amino acids and by having a specific Pel B sequence leader of 22 amino acids. Surprisingly, DIATHIS-1 displays the formation of dimers and oligomers which show unusual stability. Without the Pel B sequence, DIATHIS-1 behaves as a monomer. This new fusion protein, or scFv, possesses a very high affinity for recombinant CEA antigen and efficient recognition of CEACAM1 proteins in human metastatic melanoma. Moreover, the isolation of selected oligomeric forms obtained by an original isolation method confers to this scFv a pharmacokinetic performance superior to that of the previously reported scFvs and better than conventional diabodies (2; 3).

The fusion protein of the invention is referred to herein as an scFv, and no particular significance is to be attached to either usage, in the absence of any indication to the contrary. It will be appreciated, therefore, that reference to the fusion protein of the invention also includes reference to the scFv fused with a leader sequence and an effector sequence, for example.

The scFv initially identified in the art as being useful was scFvE8 (1), and corresponds to the $V_H$-Linker-$V_L$ portion of scFvDIATHIS-1, SEQ ID NO: 1 or SEQ ID NO:2, in the accompanying Sequence Listing, and in FIG. 15, but wherein C>W, P>L and W>R in those positions marked with an asterisk. These positions are C, P and W, respectively, in scFvDIATHIS-1, and W, L and R respectively in scFvE8.

In general the scFv portion of the fusion protein of the invention may be any scFv that has specificity for the carcinoembryonic antigen (CEA), preferably CEACAM1. More particularly, it is preferred to identify the scFv anti-CEA portion from a phage antibody library, using CEA as substrate antigen. More preferably the scFv portion of the fusion protein of the invention is scFvE8.

It is particularly preferred to further stabilise scFvE8 in the present invention by reversing the C>W mutation at position 243, thereby permitting the formation of a disulphide bridge between this position and the cysteine at position 178. The L>P mutation at position 201 is not essential, but is preferred. The R>W mutation at position 209 is not essential, but is preferred. The L>P and R>W mutations may both be present, or only one present. It is also possible for neither mutation to be present.

Other mutations, such as by point mutation, replacement, insertion, deletion, and inversion of both the encoding nucleic acid sequence and amino acid sequence are possible, provided that the resulting scFv portion of the fusion protein of the present invention is not recognised as foreign, or non-human, when administered to a patient, and that it continues to have specificity for CEA, and preferably CEACAM1, of at least 50% that of scFvDIATHIS-1 as measured in accordance with the accompanying Examples. Preferably, the specificity is at least 80%, and more preferably at least 90% of that of scFvDIATHIS-1, and may exceed 100%.

Further mutations may be incorporated for reasons of increased stability or for manufacturing requirements, for example. A particularly preferred scFv portion corresponds to the $V_H$ and $V_L$ portions of scFvDIATHIS-1 as shown in SEQ ID NO: 1 or SEQ ID NO:2 of the accompanying Sequence Listing and in FIG. 15, linked by an appropriate linker, such as that shown for scFvDIATHIS-1, SEQ ID NO: 1 or SEQ ID NO:2, in the Sequence Listing, and in FIG. 15.

A linker is not essential, although it is preferred to use a linker. A suitable linker includes one or more units of GGGGS (SEQ ID NO:15).

The length of the linker between the $V_H$ and $V_L$ portions of the scFv has an effect on dimerisation in the scFv's of the art, and diabodies are induced by shortening the linker to about 5 to 10 aa. An scFv with a 15 aa linker is expected not to form oligomers, and this represents a surprising finding for the DIATHIS-1 scFv, which we have shown to form oligomers, even with loner linkers.

The leader sequence should be cleavable by the E. coli Pel B peptidase, which is found in the periplasmic space surrounding E. coli. In general, this leader sequence is used to encourage secretion of fusion proteins across the cellular membrane to enable continuous production of the fusion protein without building up levels of the fusion protein in the host that can poison or otherwise inhibit further production. In the present invention, it is preferred to collect the fusion protein before it has been secreted, and while it is still present in inclusion bodies in the host. This can be achieved by transforming the host with a suitable plasmid or vector, culturing the host under permissive conditions to a sufficiently high optical density (OD) and collecting and rupturing the cells, such as by homogenisation and centrifugation of the lysate, to obtain the fusion proteins as inclusion bodies in the pellet. It will be appreciated that it is preferred to disable or remove the Pel B peptidase before rupturing the cell membrane, to minimise loss of target fusion protein.

It will be appreciated that the leader sequence may vary in a similar manner to that described above for the scFv portion of the fusion protein, but wherein the functional limitation is the ability to be cleaved by E. coli Pel B peptidase. It is preferred that leader sequence functionality is also retained, such that the fusion protein will be secreted across E. coli cell membrane if cultivated for sufficient time under permissive conditions.

It is preferred that the fusion protein, or scFv, of the invention is provided with a tag. In the accompanying Examples, a D3SD3-FLAG-His6 versatile tag (26) is used. This includes a phosphorylation site (D3SD3), the FLAG M2 tag sequence (for detection with an anti-FLAG M2 antibody) and the 6×His (SEQ ID NO:16) tag, allowing rapid purification by metal affinity chromatography (IMAC). There is no requirement for a tag, but tags can be used to assist with purification and detection of the scFv. In the above example, any one or more of the components, D3SD3, FLAG and His6 (SEQ ID NO:16), may be omitted. Of the components, the His6 (SEQ ID NO:16) tag is particularly useful for permitting the use of IMAC, but other tags may be used as are well known to those skilled in the art.

The fusion protein, or scFv, of the present invention may be used on its own to detect cancerous tissue, for example. In this respect, it may be radio-labelled, such as by radio-iodination. Other labels will be apparent to those skilled in the art.

In a preferred embodiment, the fusion protein of the present invention further comprises an effector. The effector is a portion of the fusion protein that is able to exert a particular function when the fusion protein comes into contact with the target CEA or CEACAM1 antigen. For example, HIV1 vpr and LLOΔPEST are two toxins derived from HIV1 and *L. monocytogenes* respectively. These effectors have different mechanism of action, and both cause the death of eukaryotic cells, Yeast Cytosine Deaminase (YCD) is an enzyme from yeast able to convert the non-toxic antifungal agent 5-fluorocytosine (5-FC) into the known anticancer agent, 5-fluorouracil (5-FU). Ubiquitin is a well known and ubiquitous protein that is internalised in some cells and increases the probability of the scFv being labelled with radiolabelled iodine. IL2 is a cytokine used for the treatment of melanoma and its fusion with DIATHIS-1 allows it to be targeted. Other effectors will be apparent to those skilled in the art. We have demonstrated that the inclusion of an effector need not result in a significant loss of specificity of the scFv for CEA and CEACAM1.

As with the $V_H$ and $V_L$ regions, the effector may be linked directly to the scFv portion, or via a linker, such as SSSSG (SEQ ID NO:17), which may be present as a monomeric unit or 2 or more, typically 2-5, units.

Expression of the scFv of the invention is generally achieved by incorporation into a suitable expression plasmid, such as the pET22b(+) vector. In the pET vector system the cloned gene is under the control of the strong bacteriophage T7 promoter, and expression is induced by providing a source of T7 RNA polymerase in the host cell. This promoter was selected for its strength, but other promoters can be used, such as the phage T5 promoter, lac promoter, and other promoters suitable for prokaryotic protein expression. It will be apparent to the skilled person that the choice of other promoters may influence protein expression and final yield.

It will also be appreciated that the expression cassette for the fusion protein of the invention will generally comprise other elements essential for expression or that may assist, such as a stop codon, for example.

The original scFv from which derive the E8 clone has been tested and show reduced affinity for the antigen (Pavoni et al 2006). Random mutations were introduced in the E8 clone to increase the affinity (there are 8 amino acid changes between the original scFv and E8 clone). One of this mutation is a C>W change. In the DIATHIS-1 this mutation was reversed by another point mutation, in which the nucleotide was changed back to its original state, to recover the cysteine in order to enhance stability of the scFv. The other two mutations were introduced casually. Surprisingly, although E8 was modified to enhance affinity for CEA (1), the affinity of DIATHIS-1 for CEA is higher than that of ES ($1.88\times10^8 M^{-1}$ and $1.39\times10^8 M^{-1}$ respectively), There are generally two basic strategies for obtaining recombinant antibody fragments from *Escherichia coli*. The first is to produce antibody proteins as cytoplasmic inclusion bodies, followed by refolding in vitro. In this strategy, the protein is expressed without a signal sequence, under a strong promoter. The inclusion bodies contain the recombinant protein in a non-native and nonactive conformation. To obtain functional antibody, the recombinant polypeptide chains must be dissolved and folded into the right shape, by using a laborious and time-consuming refolding procedure (Kipriyanov, S. M., and Little, M. Mol. Biotechnol, (1999)), The second approach for obtaining functional antibody fragments is to imitate the situation in the eukaryotic cell for secreting a correctly folded antibody. Antibody fragments are secreted into the periplasmic space and even into the medium of *E. coli*, by fusing a bacterial signal peptide to the antibody N-terminus (Better, M., Science (1988); Skerra, A., Science (1988)). scFvs are usually correctly processed in the periplasm; they contain intramolecular disulphide bonds and are soluble.

In the present invention, we used the second method described above for the purification of scFv by extracting DIATHIS-1 (fused at the N-terminus to pelB) from *E. coli* periplasm, but the final product contained high levels of endotoxins and the final yield was poor. In order to increase the yield, protein expression was performed in *E. coli* high cell density cultures. Surprisingly, under these conditions, the protein was found exclusively in the inclusion bodies. Refolding then occurred during the first step of elution.

The present invention will be further illustrated with reference to the accompanying, non-limiting Figures, in which:

FIG. 1 shows the structure of the expression construct of DIATHIS-1;

FIG. 2 shows the amino acid sequence (SEQ ID NO:18) and secondary structure prediction of scFv DIATHIS-1 including Pel B and the D3SD3-FLAG-His6 tag;

FIG. 3(A) shows the flow scheme for the up-stream process, while (B) shows SDS-PAGE 12% analysis of scFvDIATHIS-1 expression;

FIG. 4 provides a flow scheme of the scFvDIATHIS-1 down stream process;

FIG. 5 shows (A) Chromatogram of the third purification step showing the two elution peaks corresponding to 0.2M NaCl and 0.5 M NaCl. (B) SDS-PAGE 12% analysis of purified scFv DIATHIS-1 eluted with 0.2M NaCl (0.2M) and 0.5 M NaCl (0.5M). (C) Native PAGE analysis of the same proteins. (D) Native PAGE analysis after the addition of β-mercaptoethanol as reducing agent in the sample. (E) Native PAGE analysis after the addition of the detergent Sodium Dodecyl Sulphate in the sample;

FIG. 6 shows antigen recognition by the two forms of DIATHIS-1. The ELISA assay was performed with different amounts of DIATHIS-1 0.5 M (A) and 0.2 M (B) respectively on plates coated with 100 ng of CEA antigen;

FIG. 7 shows the specificity of DIATHIS-1 0.2M determined by cytometric assay (FacScan analysis). Cytograms display the results obtained on melanoma cell population (solid peaks) with respect to CEA negative cells COS1 (grey, middle lines). The black lines represent melanoma cells that have received only the secondary antibodies;

FIG. 8 illustrates the specificity of DIATHIS-1 for CEACAM1 positive cells;

FIG. 9 shows size exclusion chromatography performed using an ÄKTA Chromatography system in isocratic condition (phosphate buffer 50 mM pH 7.5 and NaCl 0.15 M);

FIG. 10 shows (A) in vivo pharmacokinetic over short and long time intervals of DIATHIS-1. Estimated half life $t_{1/2}\alpha$: 0.07±0.013 hr; $t_{1/2}\beta$: 8.58±3.15 hr; $AUC_{24\,h}$: 113±115. (B) Pharmacokinetic over a long period. Half life $t_{1/2}$: 8.84±33 h (calculation performed with Origin 8.1);

FIG. 11 shows biodistribution in tumour-bearing nude mice. Mice were injected intravenously with [124I]-DIATHIS-1. Tumour and normal tissue uptake was expressed as percentage ID/gr;

FIG. 13 shows the structure of various fusion proteins, comprising an effector, of the present invention (His6=SEQ ID NO:16: (SSSSG)$_2$=SEQ ID NO:19; (SSSSG)$_3$=SEQ ID NO:20);

FIG. 15 shows nucleotide sequence (SEQ ID NO:1) and corresponding amino acid sequence (SEQ ID NO:2) for scFv-DIATHIS-1. Nucleotidic and amino acidic sequences of scFv DIATHIS-1 including the pelB signal, the V$_L$, the linker, the V$_H$ and the C-terminus D3SD3-FLAG-His6 tag. The mutations inserted in scFv DIATHIS-1 relative to scFvE8 are marked with an asterisk;

FIG. 16 shows nucleotide sequence (SEQ ID NO:21) and corresponding amino acid sequence (SEQ ID NO:22) for scFvDIATHIS-1:Ubiquitin. Nucleotidic and amino acidic sequences of scFv DIATHIS-1 including the pelB signal, the V$_L$, the linker, the V$_H$, and the C-terminus His tag and of Ubiquitin. The mutations inserted in scFv DIATHIS-1 relative to scFvE8 are marked with an asterisk;

FIG. 17 shows nucleotide sequence (SEQ ID NO:23) and corresponding amino acid sequence (SEQ ID NO:24) for scFvDIATHIS-1:HIV-vpr. Nucleotidic and amino acidic sequences of scFv DIATHIS-1 including the pelB signal, the V$_L$, the linker, the V$_H$, and the C-terminus His tag and of HIV-vpr. The mutations inserted in scFv DIATHIS-1 relative to scFvE8 are marked with an asterisk;

FIG. 18 shows nucleotide sequence (SEQ ID NO:25) and corresponding amino acid sequence (SEQ ID NO:26) for scFvDIATHIS-1:YCD. Nucleotidic and amino acidic sequences of scFv DIATHIS-1 including the pelB signal, the V$_L$, the linker, the V$_H$, and the C-terminus His tag and of YCD. The mutations inserted in scFv DIATHIS-1 relative to scFvE8 are marked with an asterisk;

FIG. 19 shows nucleotide sequence (SEQ ID NO:27) and corresponding amino acid sequence (SEQ ID NO:28) for scFvDIATHIS-1:LLOΔPEST. Nucleotidic and amino acidic sequences of scFv DIATHIS-1 including the pelB signal, the V$_L$, the linker, the V$_H$, and the C-terminus His tag and of LLOΔPEST. The mutations inserted in scFv DIATHIS-1 relative to scFvE8 are marked with an asterisk; and FIG. 20 shows the nucleotide sequence (SEQ ID NO:29) and corresponding amino acid sequence (SEQ ID NO:30) for scFvDIATHIS-1:IL-2. Nucleotidic and amino acidic sequences of scFv DIATHIS-1 including the pelB signal, the V$_L$, the linker, the V$_H$, and the C-terminus His tag and of IL-2. The mutations inserted in scFv DIATHIS-1 relative to scFvE8 are marked with an asterisk.

Figure 4:
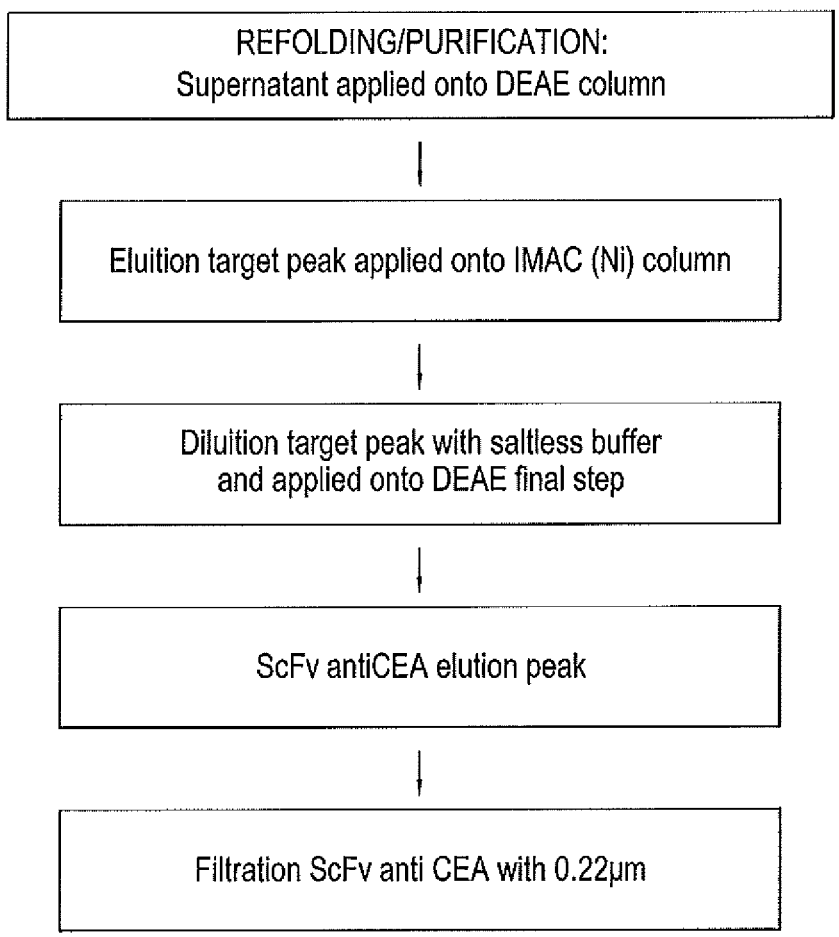

The preferred purification method used herein is based on three chromatographic steps (c.f. FIG. 4). The chromatographic process may be performed using an AKTA explorer chromatography system (GE Healthcare, Bucks, UK). The first step is anion exchange DEAE chromatography. This can use a BPG 100/500 column with DEAE fast flow resin, for example. The column is equilibrated, using a 50 mM phosphate buffer; NaCl 50 mM; urea 8M; pH 7.5, for example. The supernatant solution is charged onto the column and a linear gradient step, for example, used to eliminate urea. Bound material may be eluted with 50 mM phosphate buffer; NaCl 0.5M; glycerol 10% pH7.5. The second step is an IMAC chromatography. This may be performed by loading the DEAE elute pool onto a BPG 100/500 column packed with IMAC (Ni) Sepharose resin, which can be equilibrated with 20 mM phosphate buffer, NaCl 0.5M, 20 Mm imidazole, pH 7.5. Bound material can be eluted with 20 mM phosphate buffer, containing NaCl 0.5M and 250 Mm imidazole pH 7.5. The IMAC eluate pool is then diluted. This can be done using 1:10 in 20 mM phosphate buffer, 1.5 mM EDTA, 10% (v/v) glycerol, pH 7.5, and is suitably loaded onto a Sepharose fast flow resin in a column, such am BPG 100/500 column, for the third chromatographic step. The column is equilibrated using, for example, 20 mM phosphate buffer containing NaCl 50 mM, 1.5 mM EDTA and 10% (v/v) glycerol, pH 7.5. The resulting ScFv DIATHIS-1, or other scFv, may be eluted with 20 mM phosphate buffer, NaCl 0.2M or 0.5M, and 1.5 mM EDTA and 10% glycerol as stabilising agents.

The process used in the Examples provides high yields of refolded protein with very low levels of endotoxins.

Interestingly, the final elution step elutes lower, more functional oligomeric scFv preparations using a first run of about 0.2M NaCl, while a second run of about 0.5M NaCl elutes higher molecular weight aggregates with lower functionality. While both are useful, the oligomeric preparations are preferred.

The following Examples are for illustrative purposes only, and do not restrict the present invention in any way.

EXAMPLES

Engineering scFv DIATHIS-1 Anti CEA

Human scFv anti-CEA was isolated from ETH-2 human antibody phage library (25, 2) by phage display while E8 clone, with increased antigen affinity, was obtained by affinity maturation as previously described (1). In the pDN332 vector, the scFvE8 construct contains at the C-terminus, a D3SD3-FLAG-His6 versatile tag (26), including a phosphorylation site (D3SD3), the FLAG M2 tag sequence (for detection with an anti-FLAG M2 antibody) and the 6×His (SEQ ID NO: 16) tag allowing rapid purification by metal affinity chromatography (IMAC). The scFv DIATHIS-1 construct was cloned into a pET22b(+) vector by cloning the scFvE8 sequence from pDN332 including the D3SD3-FLAG-His6 tag. In the pET vector system, the cloned gene is under the control of the strong bacteriophage T7 promoter and expression is induced by providing a source of T7 RNA polymerase in the host cell. We chose this promoter for its strength, but other promoters can be used, for example phage T5 promoter, lac promoter, and all promoters suitable for prokaryotic protein expression. The choice of promoter is likely to influence protein expression and final yield.

We chose to include the bacterial signal peptide pal B at the N-terminus of scFv, which enables the export of soluble scFv into the periplasm (FIG. 1) (27; 6) in order to increase the protein expression level (28, 29). The sequence was amplified from pDN332 vector with degenerated primers: aCEANcoI5'forward primer 5'-CCAGCCGGCCATGGC-CGAGGTG-3', SEQ ID NO: 3, and a CEA EcoRI3'reverse primer 5'-ACAACCATATGCAGTCTAATGGTGATGGTG-3', SEQ ID NO: 4, to create an NcoI and an EcoRI sites at 5' and 3'termini respectively. Amplicons were digested together with the pET22b(+) vector, with NcoI and EcoRI at 37° C. for 2 hours. The digested products were purified and ligated together with T4 DNA ligase at 4° C. overnight. The ligation mix was transformed into *E. coli* strain JM109. Positive clones were screened for the correct insertion by colony PCR.

Figure 1:

Accompanying FIG. 1 shows the structure of the expression construct of DIATHIS-1. The gene encoding the human scFv DIATHIS-1 antibody to CEA is fused at the N-terminus to the Pel B sequence leader peptide and, at C-terminus, to the D3SD3-FLAG-His6 tag, and the resulting construct inserted in a prokaryotic pET vector under the control of the strong T7 promoter.

In order to improve the stability of the antibody domains, the C>W mutation introduced in E8 clone during maturation in the CD3 region of variable light chain ($V_L$) (1), was reversed by in vitro site-directed mutagenesis. This cysteine in fact, is involved in the formation of disulphide bond between the CDR regions of $V_L$. The stabilising effect of the disulphide bonds has been tested experimentally (30). The few antibodies that are functional despite having lost one of the conserved cysteine residues through somatic mutation (31) appear to have above average thermodynamic stability after the missing disulphide bond has been restored (32). The final sequence of the new scFv DIATHIS-1 was obtained by sequencing reaction. We observed that, surprisingly, two new mutations had been introduced into the $V_L$, probably during PCR amplification for cloning procedures. These are: L>P and R>W.

Figure 2:
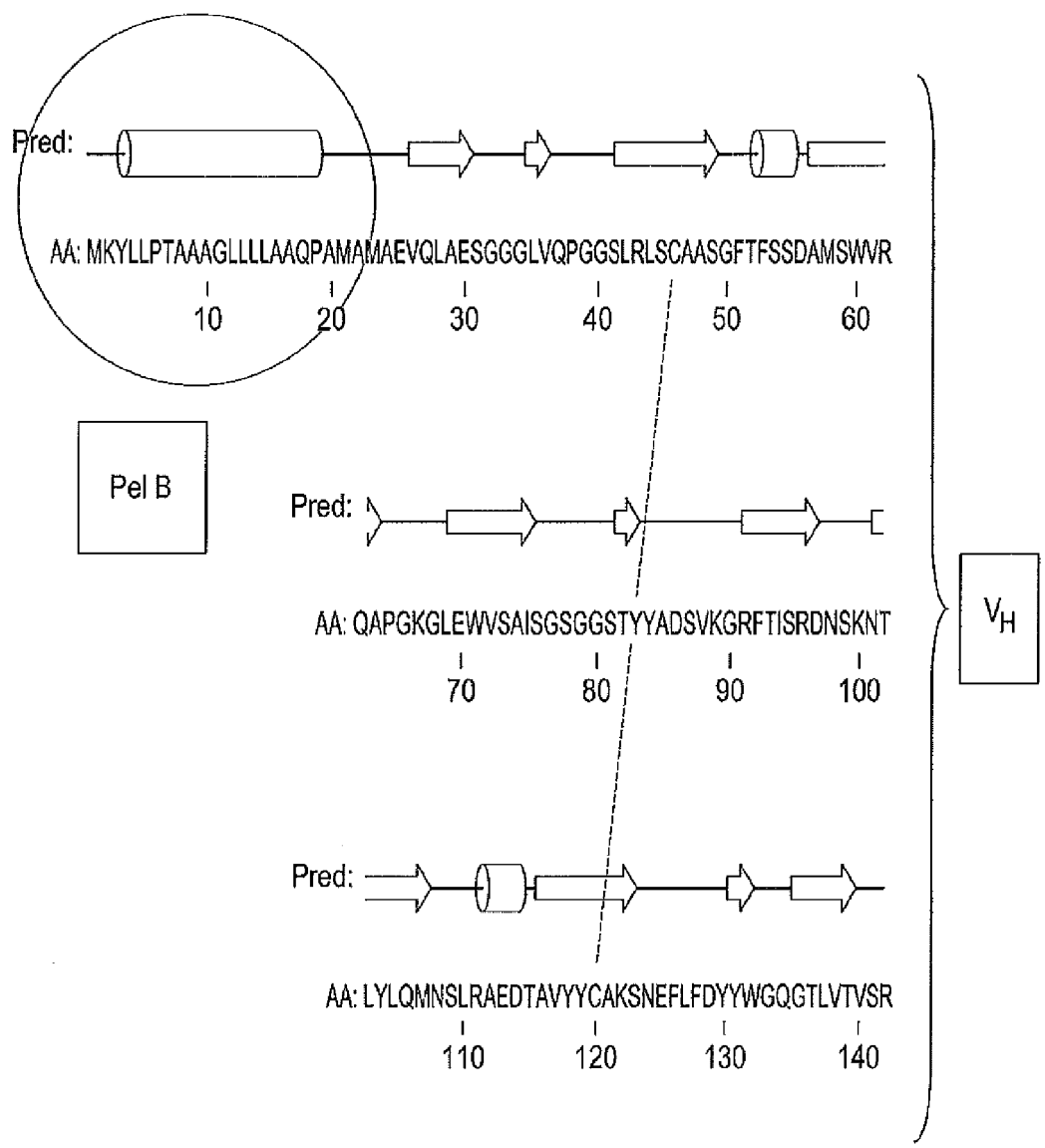
Figure 2:
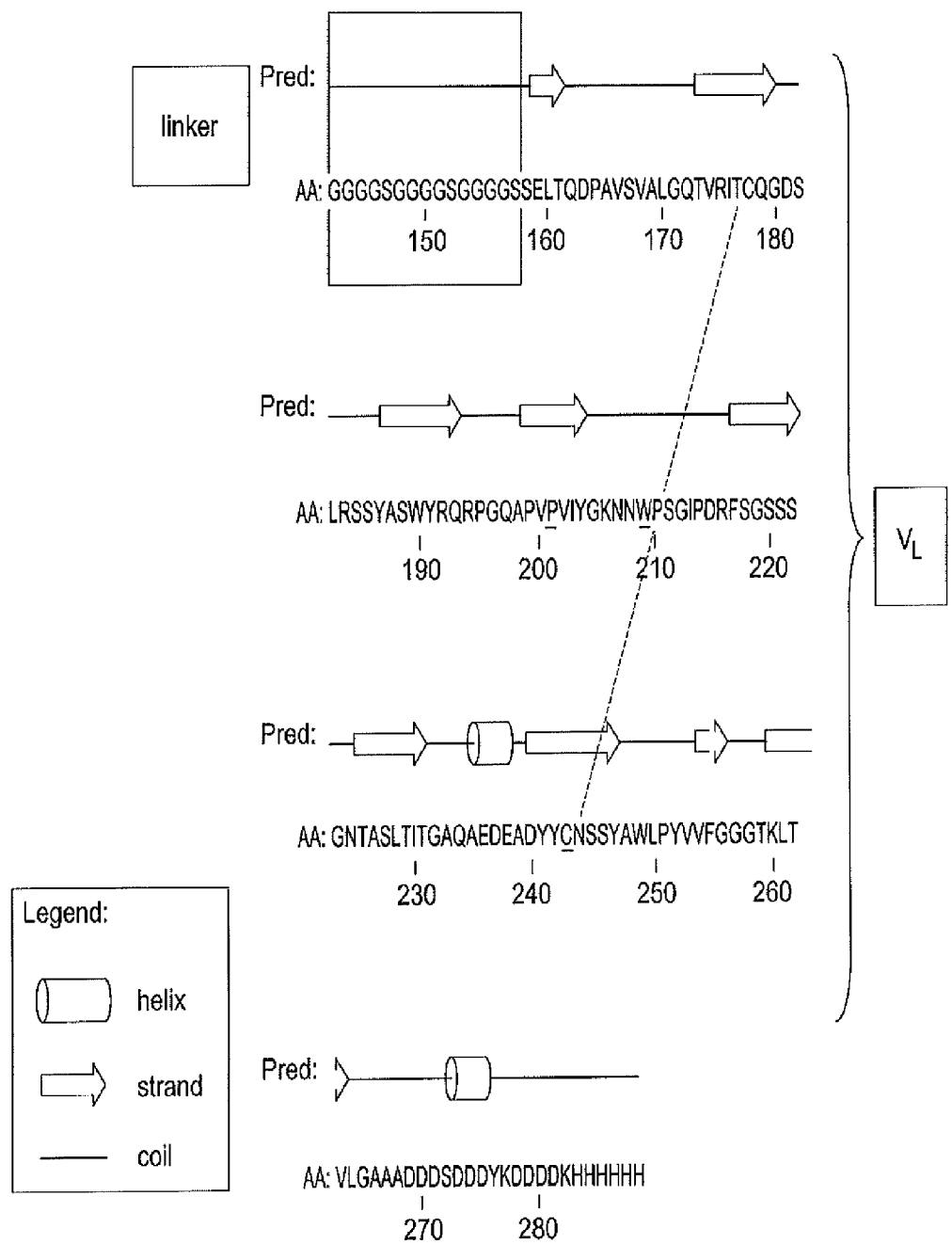

Thus, we used the E8 clone and added a leader sequence (Pel B) and 3 new mutations, causing three amino acid changes from the E8 sequence. In particular the conversion of W to C confers more stability because this cysteine is involved in the formation of the intra-chain disulphide bond. The amino acid sequence and secondary structure prediction of scFv DIATHIS-1 including Pel B and the D3SD3-FLAG-His6 tag is illustrated in FIG. 2. The final construct was transferred into *E. coli* BL21(DE3) host strain (F-ompT hsdSB(rB-mB-)gal dcm (DE3))]) containing a chromosomal copy of T7 RNA polymerase gene under the control of lacUV5 promoter, to induce scFv expression.

FIG. 2 shows a schematic representation of the engineered scFv DIATHIS-1 anti-CEA. Amino acid sequence (AA) and predictive secondary structure (pred) of scFv DIATHIS-1 anti-CEA. The mutations inserted into scFv DIATHIS-1 are underlined and the disulphide bridges between antibody domains are represented as dotted lines.

Manufacture of Recombinant scFv Anti-CEA DIATHIS-1

For the large scale production of scFv DIATHIS-1 we used *E. coli* high cell density cultures (for review see 33) and optimised a feeding strategy and fermentation variables enabling high level production of scFv DIATHIS-1 in the inclusion bodies (FIG. 3B). The flow diagram of the up-stream process is represented in FIG. 3A. The overnight *E. coli* BL21 (DE3) starter cultures were inoculated into a Biostat C15 vessel containing the fermenter synthetic basic media (pH 7.5): potassium dihydrogenorthophosphate 13.3 g/L, ammonium hydrogen phosphate 4 g/L, citric acid monohydrate 1.7 g/L, iron (III) citrate hydrate 100.8 mg/L, cobalt (II) chloride hexahydrate 2.5 mg/L, manganese (II) chloride tetrahydrate 15 mg/L, copper (II) chloride dehydrate 1.5 mg/L, boric acid 3.0 mg/L, sodium molybdate dehydrate 2.1 mg/L, zinc acetate dehydrate 33.8 mg/L, and EDTA 1.4.1 mg/L. Afterwards, ampicillin 100 mg/L, thiamine 2.25 mg/L, Mg solution 300 mg/L and glucose 7.56 g/L were added. Diluted bacteria were then incubated at 37° C. with glucose exponential feeding up to an optical density of at least 10. For the expression of scFv DIATHIS-1 1 mM IPTG and 40 mM sucrose were added. The fermentation was continued for 4 hours at 37° C. then cells were harvested by centrifugation at 5,000 rpm for 30 min at 4° C.

For the extraction of DIATHIS-1 from the insoluble fraction of the cytoplasm, the cell paste was resuspended in 20 ml/gr of bacterial pellet in lysis buffer (50 mM phosphate buffer; 50 mM NaCl; pH 7.5) and the cell lysis solution was processed through the microfluidiser for one pass only at 680 Bar and centrifuged at 8,000 rpm for 60 min at 4° C. For the solubilisation of inclusion bodies, the pellet was resuspended in 20 ml/gr of Solubilisation Buffer (50 mM phosphate buffer; 50 mM NaCl; Urea 8M; pH 7.5) and incubated for 16 hours with agitation. The processed product was pelleted at 8,000 rpm for 1 h at 4° C. The supernatant solution containing the scFv DIATHIS-1, was filtered through 0.45 μm filter and processed for protein purification.

FIG. 3(A) shows the flow scheme for the up-stream process, while (B) shows SDS-PAGE 12% analysis of scFvDIATHIS-1 expression, in which; Lane 1: Low range molecular weight marker; Lane 2: scFv standard 1 μg; Lane 3: Uninduced sample; Lane 4: Induced sample 2 h; Lane 5: Induced sample 3 h; Lane 6: Induced sample 4 h, We developed a purification method based on three chromatographic steps (FIG. 4). The chromatography process was performed using an AKTA explorer chromatography system (GE Healthcare, Bucks, UK). The first step is anion exchange DEAE chromatography in a BPG 100/500 column with DEAF fast flow resin. The column was equilibrated with 50 mM phosphate buffer; NaCl 50 mM; urea 8M; pH 7,5. The supernatant solution was charged onto the column and a linear gradient step was used to eliminate urea. Bound material was elated with 50 mM phosphate buffer; NaCl 0.5M; glycerol 10% pH7.5. The second step is an IMAC chromatography in which the DEAE elute pool was loaded onto a BPG 100/500 column packed with IMAC (Ni) Sepharose resin. The column was equilibrated with 20 mM phosphate buffer, NaCl 0.5M, 20 mM imidazole, pH 7.5. Bound material was eluted with 20 mM phosphate buffer, containing NaCl 0.5M and 250 mM imidazole pH 7.5. The IMAC chute pool was diluted 1:10 in 20 mM phosphate buffer, 1.5 mM EDTA, 10% (v/v) glycerol, pH 7.5, and loaded onto a BPG 100/500 column with DEAE Sepharose fast flow resin for the third chromatographic step. The column was equilibrated with 20 mM phosphate buffer containing NaCl 50 mM, 1.5 mM EDTA and 10% (v/v) glycerol, pH 7.5. ScFv DIATHIS-1 was eluted with 20 mM phosphate buffer, NaCl 0.2M, and 1.5 mM EDTA and 10% glycerol as stabilising agents.

FIG. 4 provides a flow scheme of the scFvDIATHIS-1 down stream process.

Separation of Stable Oligomeric DIATHIS-1 Forms with High Affinity and High Molecular Weight Multimers with Reduced Affinity While developing a strategy to purify DIATHIS-1, we found that good recovery of protein can be obtained by eluting the third DEAE chromatography with 0.5 M NaCl. However, if the sample is eluted first with 0.2M NaCl and then with 0.5 M NaCl in the final eluomatographic step, we found that two peaks of DIATHIS-1 are recovered (FIG. 5A), surprisingly. Both eluted proteins have the same behaviour in SDS-PAGE but the purity estimated by densitometric analysis, as well as the final yield, is higher in those eluted with 0.2M NaCl (FIG. 5B Table 1). Furthermore, we investigated the conformation of purified scFvs eluted with 0.2M NaCl and with 0.5 M NaCl on PAGE analysis under different conditions. In SDS-PAGE both proteins migrate as monomers of expected size of about 35 kDa (FIG. 5B). In native-PAGE, the scFv DIATHIS-1 protein eluted with 0.2M NaCl migrates as three clearly distinguishable forms, differently represented, which show unusual stability in both non-reducing (FIG. 5C) and reducing (FIG. 5D) conditions while those eluted with 0.5M NaCl form higher molecular weight aggregates (FIGS. 5C and D). The PAGE monomer behaviour is ripristinated by the addition of SDS in the sample (FIG. 5E). These results are consistent with the formation of oligomeric forms of DIATHIS-1 due to non covalent interactions. Thus, with the optimised purification method developed we are able to discriminate between oligomeric forms and higher molecular weight aggregates that elute with 0.5M NaCl (FIG. 5C-D).

TABLE 1 features of scFv DIATHIS-1 at different steps of the production process. The yield values refer to the total amount of protein, and the purity to DIATHIS-1.

| PURIFICATION STEP | Yield (g) | % purity | Endotoxin Content (EU/µg) |
|---|---|---|---|
| Supernatant Urea 8M | 3.5 g | 40% | — |
| First chromatographic step | 1.5 g | 75% | <5 EU/µg |
| Second chromatographic step | 1.2 g | 95% | <3 EU/µg |
| Third chromatographic step 0.2M NaCl | 0.927 g | 99% | <1 EU/µg |
| Third chromatographic step 0.5M NaCl | 0.270 g | 90% | — |

Figure 5:
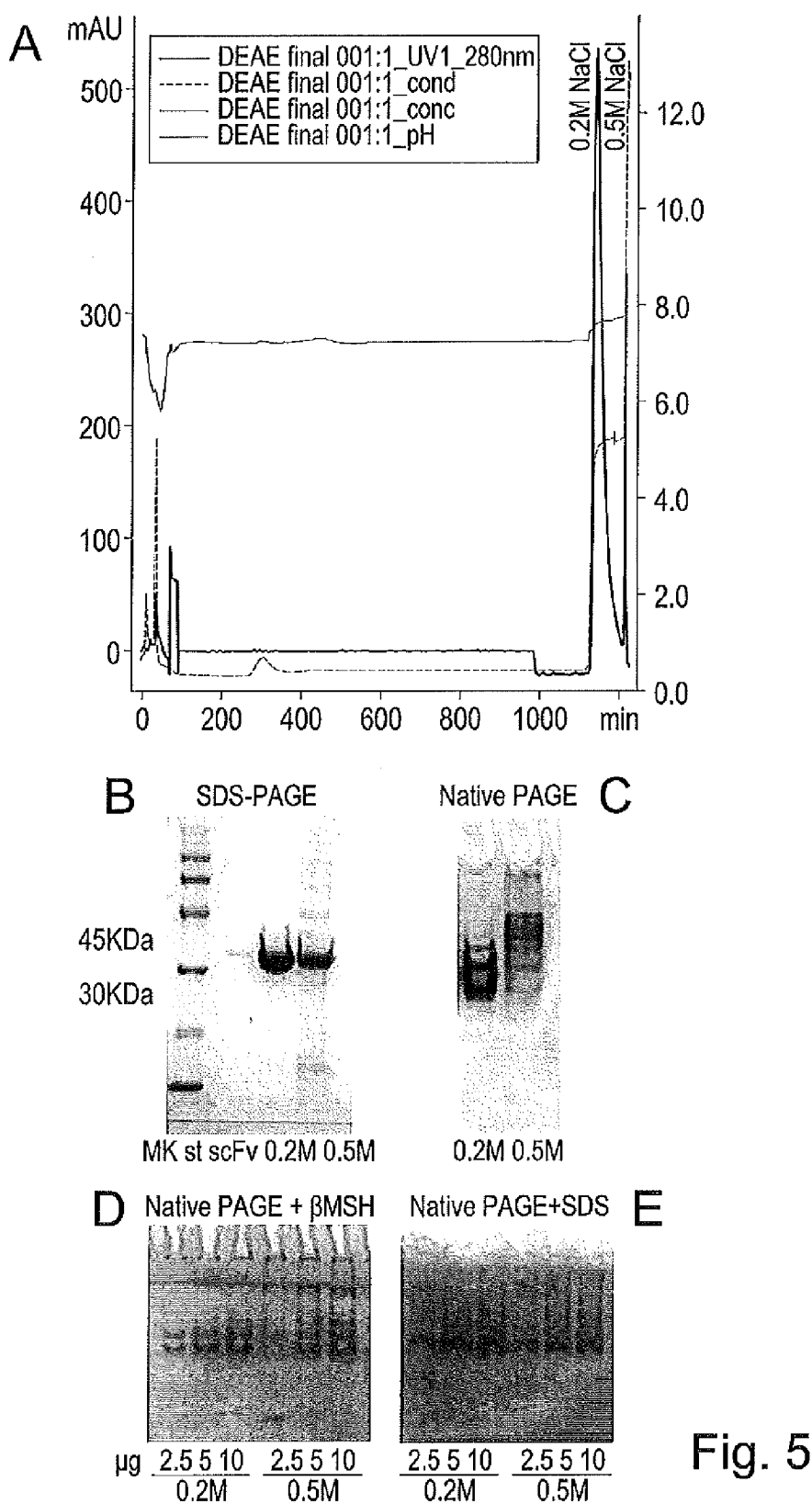

FIG. 5 shows (A) Chromatogram of the third purification step showing the two elution peaks corresponding to 0.2M NaCl and 0.5 M NaCl. (B) SDS-PAGE 12% analysis of purified scFv DIATHIS-1 eluted with 0.2M NaCl (0.2M) and 0.5 M NaCl (0.5M). (C) Native PAGE analysis of the same proteins. (D) Native PAGE analysis after the addition of β-mercaptoethanol as reducing agent in the sample. (E) Native PAGE analysis after the addition of the detergent Sodium Dodecyl Sulphate in the sample.

The two scFv DIATHIS-1 separated in the final chromatographic step, were evaluated for binding efficacy on pure CEA antigen in ELISA assays.

Different concentrations of scFv were utilised to perform the titration on 100 ng of CEA antigen coated per well. The results (FIG. 6) showed linearity and a better affinity for the DIATHIS-1 elated with 0.2M NaCl (B) compared to DIATHIS-1 elated with 0.5M NaCl (A).

FIG. 6 shows antigen recognition by the two forms of DIATHIS-1. The ELISA assay was performed with different amounts of DIATHIS-1 0.5 M (A) and 0.2 M (B) respectively on plates coated with 100 ng of CEA antigen.

The determination of antibody affinity by direct ELISA was performed according to S. Rath et al., 1988, with minor modifications (34). Microtiter plates were coated with 100 ng of the antigen in PBS buffer and incubated overnight at 4° C. After three washes plates were blocked with nonfat dry milk 2% (v/v) in PBS, pH 7.4 (PBSM) for 60 minutes at 37° C. The plates were then washed and incubated for 2 hours at room temperature (RT) with 100 µl of serial dilutions of scFv DIATHIS-1 0.2M NaCl in blocking buffer, together with 10 µl of a freshly prepared mixture consisting of an anti-FLAG M2 and an anti-mouse HRP-conjugated antibody. After the incubation time, the plates were washed, and the colorimetric reaction was developed using ABTS as substrate and the colour read at 405 nm. The direct ELISA results were background subtracted to account for non-specific binding and the data were best fitted using a statistical software package, GraphPad4, to an hyperbolic Michaelis-Menten curve. The $EC_{50}$ (concentration exhibiting 50% binding) was calculated based on obtained absorbance values. Antigen-coated microtiter plates (prepared as above) were also used for competitive ELISA assay. Serial dilutions (300 pg/ml to 100 µg/ml) of free CEA used as an inhibitor for the binding of DIATHIS-1 to bound CEA were made in blocking buffer, incubated with DIATHIS-1 0.2 M NaCl antibody at the determined $EC_{50}$ (calculated from the direct ELISA) and allowed to react for about 90 min.

After the blocking step, the solutions were added to the designated antigen-coated wells together with a freshly prepared mixture consisting of an anti-FLAG M2 and an anti-mouse HRP-conjugated antibody. The microtiter plates were rinsed thoroughly, the substrate solution applied and the enzyme reaction developed and measured as already described. All data were best fitted with GraphPad4 statistical software using a monoexponential decay equation. The molar inhibitor concentrations required for 50% inhibition ($IC_{50}$) were then determined. The $EC_{50}$ and $IC_{50}$ values were used to calculate the average antibody affinity. The scFv DIATHIS-1 eluted with 0.2M NaCl reached a $K_d$ value of $1.88 \times 10^8$ $M^{-1}$. The $K_d$ of 0.5M NaCl DIATHIS-1 could not be detected because of the non-linear binding of the antibody. The affinity of scFv CEA clone E8—reached a $K_d$ value of $1.39 \times 10^8$ $M^{-1}$ (1).

Generally upon conversion of the scFv monomer to diabody, the $K_d$ decreases over 10-15 times showing a higher affinity (35). Nevertheless, the oligomeric scFv DIATHIS-1 displays similar affinity compared to the monomeric scFv E8. This is a desirable feature. Different authors, in fact, showed that the total concentration and penetration of scFv into the tumour decreases with the affinity for the antigen (36, 37) while cellular cytotoxicity increases with the affinity.

The affinity and specificity of the two separated scFv DIATHIS-1 against CEACAM1 antigen were determined by flow cytometry analysis on CEACAM1-positive primary melanoma cell line MelP5. We used COS1 cell line as negative control. Adherent cells in exponential phase of growth were resuspended in PBS and 1% of BSA (PBSB) and then counted. For cytofluorimetric assay $5 \times 10^5$ cells were dispensed onto the tube and collected at 1,200 rpm for 10 minutes. The pellet was resuspended in 200 µl of PBSB added with the different preparations of scFv DIATHIS-1 and maintained at 4° C. for 60 minutes. After washes, pellets were suspended with 200 µl of PBSB and a mouse anti FLAG M2 diluted 1:400 (Sigma Aldrich) was added and incubated for 30 minutes at room temperature. The immune complexes were revealed by addition of a goat anti-mouse FITC conjugated antibody diluted 1:50. After 30 minutes of incubation at room temperature in the dark, the cells were washed and the fluorescence revealed by FACScan cytofluorimetry.

The results showed a high percentage of positive cells for both scFv at every concentration tested. The highest mean values, representing a parameter for the affinity of the antibody for the antigen, are obtained by using an scFv concentration of 5 µg/ml and were higher for the scFv eluted with NaCl 0.2. M compared to those obtained with elution with 0.5 M (146.6 and 95.27 respectively; Table 2), showing again the better affinity of DIATHIS-1 0.2M. The lowering of the mean values at the increasing of scFv concentration is due to the antigen binding competition characteristic of monoclonal antibodies. The results obtained on CEA negative cells (COS-1) show the specificity of scFv DIATHIS-1 anti-CEA (FIG. 7).

TABLE 2

Flow cytometry analysis of scFv DIATHIS-1. In this table are reported the percentages values of fluorescent melanoma cells MelP5 and CEA negative COS-1 reacted with the two differently eluted scFv DIATHIS-1. In the third column are reported the mean values representing the affinity of antibodies.

| | Facs Scan on CEA+ cells (Mel P5) | | Facs Scan on CEA− cells (COS-1) | |
|---|---|---|---|---|
| | % fluorescent cells | Mean (affinity) | % fluorescent cells | Mean (affinity) |
| cells | 0.56 | 5.21 | 0.40 | 4.55 |
| negative CTR | 28.34 | 19.79 | 17.66 | 15.64 |
| DIATHIS-1 0.2M 5 µg/ml | 98.28 | 146.44 | 18.16 | 15.6 |
| DIATHIS-1 0.2M 10 µg/ml | 97.50 | 114.72 | 8.58 | 11.95 |
| DIATHIS-1 0.2M 20 µg/ml | 95.80 | 85.23 | 9.91 | 13.14 |
| DIATHIS-1 0.2M 40 µg/ml | 95.43 | 66.46 | 7.80 | 12.22 |
| DIATHIS-1 0.5M 5 µg/ml | 95.91 | 95.27 | 10.46 | 14.59 |
| DIATHIS-1 0.5M 10 µg/ml | 97.75 | 85.63 | 13.62 | 14.64 |
| DIATHIS-1 0.5M 20 µg/ml | 96.29 | 91.67 | 20.83 | 16.08 |
| DIATHIS-1 0.5M 40 µg/ml | 91.57 | 80.3 | 15.74 | 16.35 |

FIG. 7 shows the specificity of DIATHIS-1 0.2M determined by cytometric assay (FacScan analysis). Cytograms display the results obtained on melanoma cell population (solid peaks) with respect to CEA negative cells COS1 (grey, middle lines). The black lines represent melanoma cells that have received only the secondary antibodies.

The antigen binding specificity of scFv DIATHIS-1 was also tested by fluorescence microscopy immunostaining as a qualitative method. MelP5 and COS-1 cells were grown on glass cover slips washed and fixed with 4% (v/v) of formaldehyde for 15 minutes at room temperature. Samples were incubated in PBS containing 1% (w/v) BSA and 0.1% (w/v) gelatine to saturate non-specific binding sites. The scFv was suspended at 5 µg/ml in blocking solution and added to the cells. After 60 minutes of incubation at room temperature 1 ml of a mouse anti FLAG M2 antibody diluted 1:400 (Sigma Aldrich) was added and the cells further incubated for 30 minutes at room temperature. After washing, an anti-mouse antibody FITC conjugate, diluted 1:200 in blocking solution, was added to the samples and the fluorescence detected using a Leica DMLB fluorescence microscope equipped with a DC300F CCD digital camera. The nuclei were stained with DAPI solution diluted 1:10000. Melanoma cells MelP5 were highly positive for scFv DIATHIS-1 staining showing a clear cellular rim signal proportional to immunocomplexes on cellular membrane, while no signal was detected on COS-1 CEA negative cells, demonstrating the specificity of DIATHIS-1 (FIG. 8).

Figure 8:
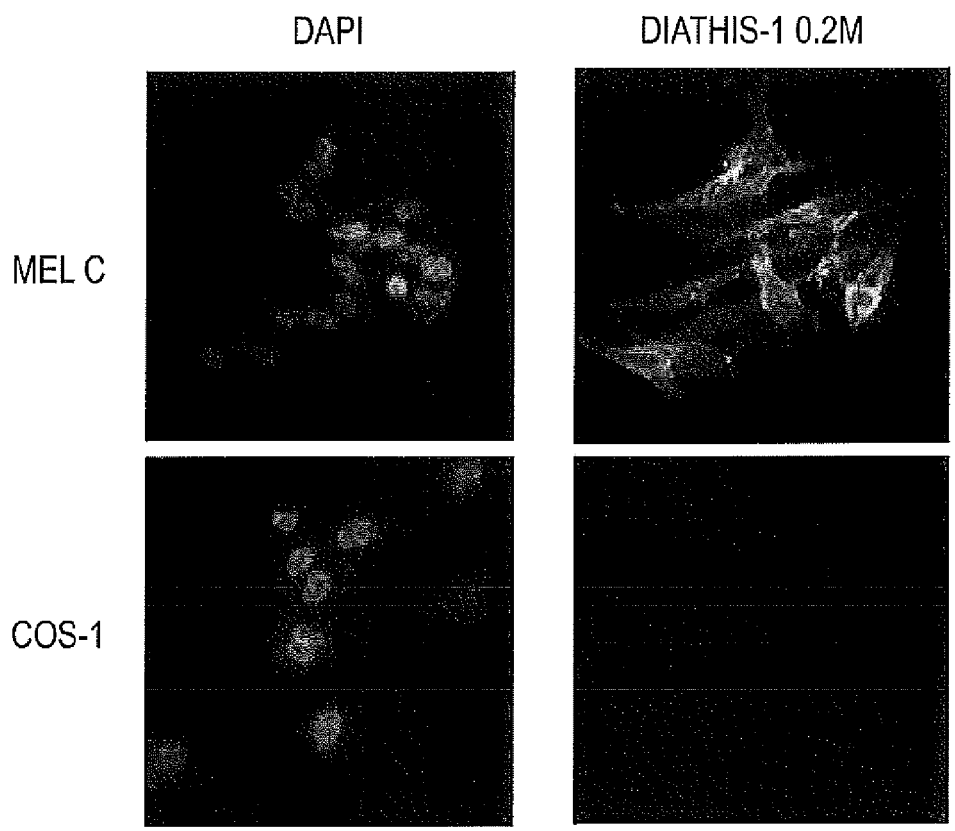

FIG. 8 illustrates the specificity of DIATHIS-1 for CEACAM1 positive cells.

Pel B is Essential for the Oligomeric Conformation of DIATHIS-1

The formation of stable oligomeric structures was an unexpected finding for a scFv having a 15 amino acid linker. One difference between the scFv of the invention and that of the art is that DIATHIS-1 retains the pel B sequence. Generally, scFv are fused to a leader sequence and then recovered in the periplasm or in the culture medium, and the leader sequence is removed by the Pel B peptidase present in the plasma membrane. In preparing DIATHIS-1, we started from the inclusion bodies, so that Pel B is not removed but it is retained, and this may influence oligomer formation.

Figure 9:
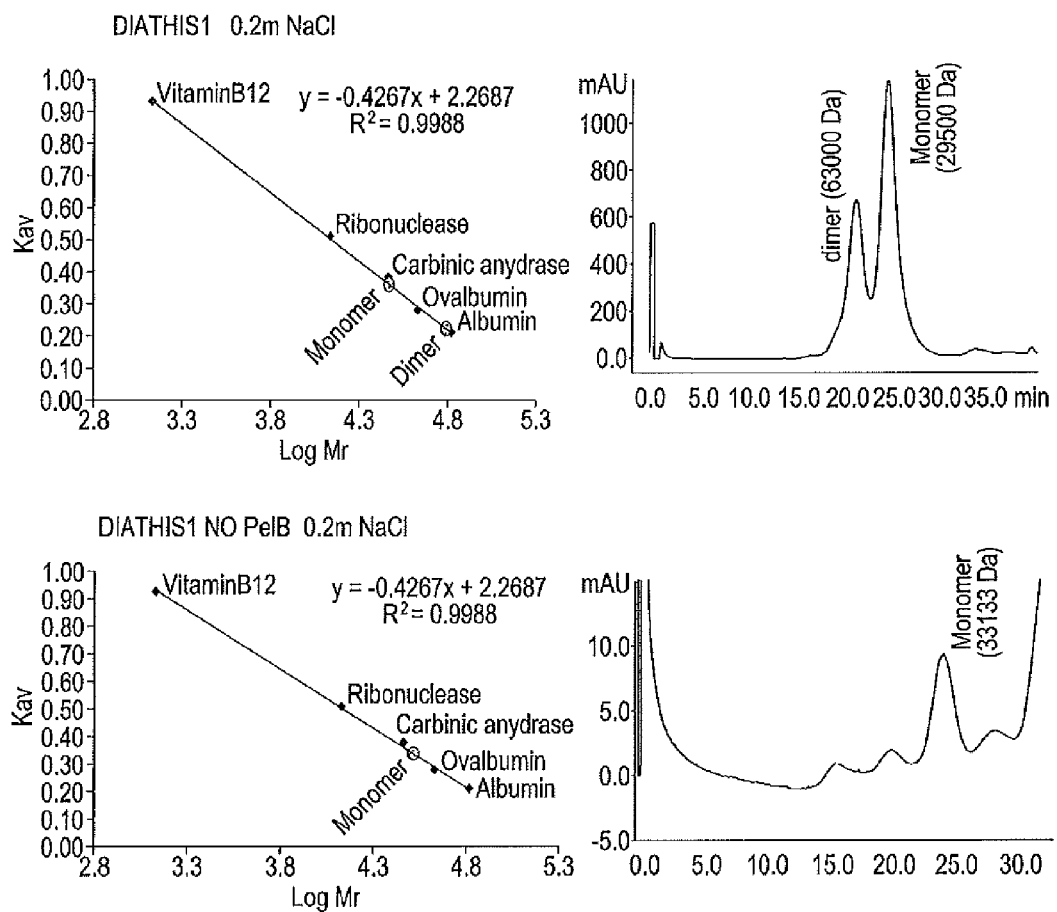

To test whether the presence of Pel B can induce the formation of scFv oligomers, we cloned the same scFv anti-CEA without the pel B sequence in a pET 45b(+) vector and purified this protein using the same method. To evaluate the behaviour of the two recombinant antibodies, we performed size exclusion chromatography (Superdex 75) with DIATHIS-1 and with the same protein without Pel B sequence. The results obtained are illustrated in FIG. 9 and demonstrate a different conformation that is not dependent on the linker (the same for both), but on the presence of Pel B. In fact, while the scFv DIATHIS-1 elutes in two different forms of about 30 Kda and 60 KDa, the same protein without the Pel B signal peptide elutes in a unique peak of 33 KDa corresponding to the monomeric form.

FIG. 9 shows size exclusion chromatography performed using an ÄKTA Chromatography system in isocratic condition (phosphate buffer 50 mM pH 7.5 and NaCl 0.15 M). The molecular weights were calculated based on Standard Curve obtained calibrating the system with proteins of known molecular weight: Albumin 67,000 Da, Ovalbumin 43,000 Da, Carbonic Anhydrase 29,000 Da, Ribonuclease 13,700 Da and Vitamin B12 1,315 Da.

The pharmacokinetics scFv DIATHIS-1 was determined in Swiss mice (CD-1 IGS). Radio-iodination of sail anti-CEA with $I^{124}$ was performed using the Iodogen methodology. Pharmacokinetics were determined after a single dose (18 µg) i.v. injection into the tail vein of mice and blood sample collected at 0, 5, 10 and 30 minutes and 2, 3, 4, 6, 24, 48 hours from injection for pharmacokinetics estimated over short and long time intervals (FIG. 10A) and 2, 3, 4, 6, 24, 48 hours for pharmacokinetics estimated over long time intervals (FIG. 10B). Plasma radioactivity was measured by a γ-counter. Many studies have reported the accelerated clearance of different scFvs and a short half-life in circulation. Unexpectedly, the scFv of the present invention showed a half life value of $t_{1/2}\alpha=0.07$ h±0.013 and $t_{1/2}\beta=8.58\pm3.15$ similar (or superior) to those obtained with bivalent scFv (scFvDb) (Table 3).

By comparison with other anti-CEA scFv molecules, scFv DIATHIS-1 has a lower elimination rate from circulation which can contribute to antibody accumulation in the tumour. Thus, the presence of the Pel B peptide at the N-terminus scFv DIATHIS-1 appears to affect oligomer formation in DIATHIS-1, which shows as an improved half-life in circulation.

Figure 10:
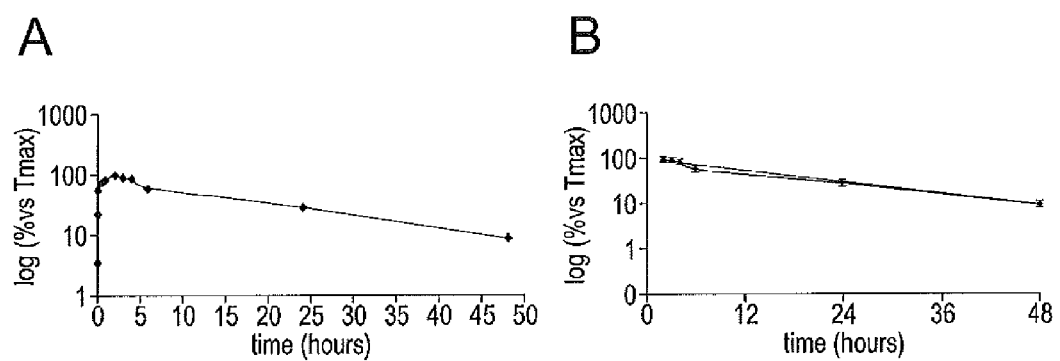

FIG. 10 shows (A) in vivo pharmacokinetic over short and long time intervals of DIATHIS-1, Estimated half life $t_{1/2}\alpha$: 0.07±0.013 hr; $t_{1/2}\beta$:8.58±3.15 hr; $AUC_{24\ h}$: 113+15. (B) Pharmacokinetic over a long period. Half life $t_{1/2}$: 8.84±3.3 h (calculation performed with Origin 8.1)

TABLE 3

Differences in pharmacokinetic performance between scFv
DIATHIS-1 and other monomeric or dimeric anti CEA scFvs.

|  | $t_{1/2} \alpha$ (hr) | $t_{1/2} \beta$ (hr) | AUC (0-24 h) | References |
|---|---|---|---|---|
| scFv T84.66/ 212 monomer | 0.12 ± 0.003 hr | 4.8 ± 0.20 | 26 | (38) |
| scFv T84.66/ 212 dimer | 0.15 ± 0.004 | 3.3 ± 0.14 | 51.72 | (38) |
| scFv T84.66 diabody | — | 2.89 | — | (39) |
| scFv MFE-23 | 0.08 ± 1 | 4 ± 1 | 18 ± 1 | (40) |
| scDbCEA | 0.17 ± 3.6 hr | 5.6 ± 1.8 | 61 ± 22 | (3) |
| scFv DIATHIS-1 | 0.07 ± 0.013 hr | 8.58 ± 3.15 | 113 ± 20 |  |

In Vivo Biodistribution and Imaging Studies in Tumour-Bearing Athymic Mice.

Xenografts were established in 7-8 weeks old CD-1 female nude mice by subcutaneous inoculation in the flank region of $5 \times 10^6$ human melanoma cancer cells Mel P5, After 20 days, when tumour masses reached 200-400 mg of weight, the mice were treated with [$^{124}$I]-DIATHIS-1. Radioiodination of scFv DIATHIS-1 was performed with $^{124}$I with the addition of a NaIO$_3$/NaI as carrier, significantly improving the yield of labelling, using the Iodogen-coated MAb protocol (41). This method has been validated to minimise chemical—as well as radiation—induced damage of the MAb (the chemical regeneration method provides a means to synchronise the I/MAb molar ratio and at the same time regenerates $^{124}$I into the iodide form. With the introduction of a regeneration method it has been possible to maximise the labelling efficiency of MAbs with $^{124}$I). For biodistribution studies of DIATHIS-1, 10 tumour-bearing mice were injected i.v. with 290 µCi of I$^{124}$DIATHIS-1 and sacrificed 4 hours post treatment.

Figure 11:
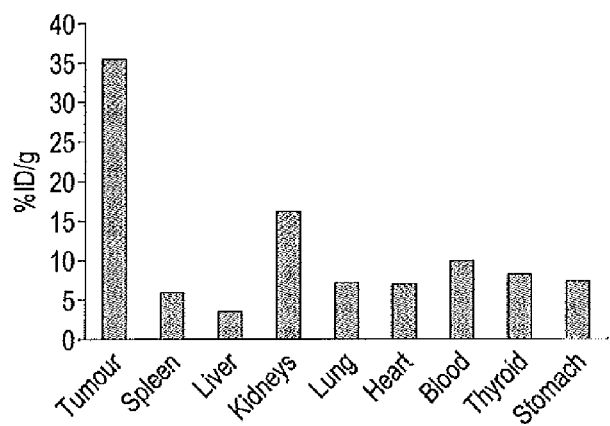

Major organs (tumour, spleen, liver, kidneys, lung, heart, blood, thyroid, stomach) were weighed and the radioactivity counted with γ-counter. The results indicate a strong localisation of DIATHIS-1 in the tumour mass, reaching values up to 35.5% injected dose/gr (Table 4; FIG. 11).

Figure 12:
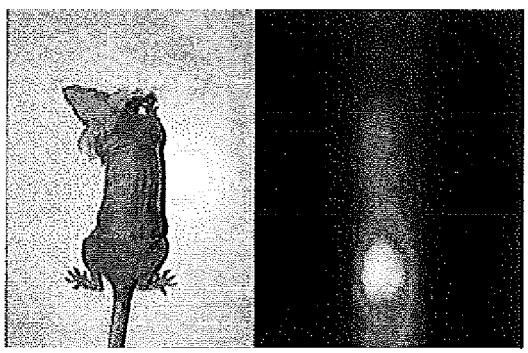
FIG. 12 shows PET imaging of [$^{124}$I]-DIATHIS-1. 290 μCu of [$^{124}$I]-scFv anti-CEACAM antibody was intravenously injected into tumour-bearing CD-I nude mice, and microPET imaging was performed under isoflurane anaesthesia.

For positron emission tomography (PET) imaging, mice were injected with 290 µCu of [$^{124}$I]-DIATHIS-1 and analysed after 4 and 6 hours post injection. Image processing and analysis were performed with standard microPET software. The results show that DIATHIS-1 localises almost exclusively in the tumour masses and that successful imaging has been achieved (FIG. 12).

TABLE 4

Biodistribution of I$^{124}$DIATHIS-1 in
athymic mice bearing MelP5 xenografts

| Organs | % ID/g |
|---|---|
| Tumor | 35.58 |
| Blood | 9.80 |
| Spleen | 5.82 |
| Liver | 3.35 |
| Kidneys | 16.06 |
| Lung | 7.08 |
| Heart | 6.90 |
| Thyroid | 8.16 |
| Stomach | 7.20 |
| Ratios |  |
| Tumor/blood | 3.62 |
| Tumor/kidney | 2.21 |
| Tumor/liver | 10.59 |

FIG. 11 shows biodistribution in tumour-bearing nude mice. Mice were injected intravenously with [124I]-DIATHIS-1. Tumour and normal tissue uptake was expressed as percentage ID/gr.

FIG. 12 shows PET imaging of [$^{124}$I]-DIATHIS-1. 290 µCu of [$^{124}$I]-scFv anti-CEACAM antibody was intravenously injected into tumour-bearing CD-1 nude mice, and microPET imaging was performed under isoflurane anaesthesia. Image acquisition time was 4 h post injection.

ScFv DIATHIS-1 anti-CEA of the present invention, when evaluated in an athymic mouse tumour xenograft model by PET, demonstrated excellent targeting and imaging properties when labelled with $^{124}$I. The tumour uptake level after 4 hours from injection was 35.5% ID/g, and was very much higher with respect to those obtained by other groups with the use of $^{124}$I. Sundaresan et al., (43) reported a tumour uptake at 18 h of 4.53±0.50% ID/g in LS174T xenograft mice treated with $^{124}$I T84.66 anti-CEA diabody. The same antibody labelled with $^{123}$I reach a maximum of 13.68±1.49% ID/g 2 h after administration (41), while the monomeric format labelled with $^{125}$I reach a maximum of 6.57±0.68% ID/g 1 h after administration and 3.66±0.62% ID/g after 6 h (38).

The scFv of the present invention can be used as imaging agent in complement to the existing diagnostic techniques and can provide a basis for a selective therapeutic approach to malignant disease.

TABLE 5

Differences on tumour uptake levels between scFv DIATH1S-1
and other monomeric or dimeric scFvs anti CEA.

|  | % ID/g | Time (hr) | References |
|---|---|---|---|
| $^{124}$I T84.66 anti-CEA diabody | 4.53 ± 0.50 | 18 | (43) |
| $^{123}$I T84.66 anti-CEA diabody | 13.68 ± 1.49 | 2 | (41) |
| $^{125}$I scFv T84.66 | 6.57 ± 0.68 | 1 | (39) |
| $^{124}$I scFv DIATHIS-1 | 35.58 ± 0.13 | 4 |  |

DIATHIS-1 Derivatives

A number of fusion proteins of DIATHIS-1 and partners of potential therapeutic interest, which fusion proteins maintain the binding properties of DIATHIS-1, have been made. Examples shown below include DIATHIS-1 fused with ubiquitin (a small peptide able to affect a number of cell properties), Vpr (a viral protein able to arrest cell growth), cytosine deaminase (an enzyme), listeriolysin (a toxin) and interleukin-2 (IL-2, a cytokine). All of the fusion proteins retained the ability to recognise melanoma cells.

scFv DIATHIS-1:Ubiquitin

The human ubiquitin sequence was amplified by PCR from the cDNA inserted in the pET3a vector with the forward primer Ub WT NotI5': 5'-GAAGGAGCGCCCGCTATGCA-GATCTTC-3'. SEQ ID NO: 5, and reverse primer UbWT-NotI3': 5'-CAAGAATGCGGCCGCACCTCTTAGTCTTA-3', SEQ ID NO: 6, which introduce a restriction site for the endonuclease NotI at both termini of ubiquitin. The amplified sequence was inserted in the pET22b(+) vector at the C-terminus of the scFvDIATHIS-1 anti-CEA. This included only the His6 (SEQ ID NO:16) tag, as the other tags were removed during the cloning procedure due to the digestion of vector with the restriction enzyme NotI. This also applies to the subsequent constructs illustrated hereinbelow. The assembled construct was transferred into E. coli BL21(DE3) for protein expression.

As for the following fusion proteins, the structure is shown in FIG. 13.

scFv DIATHIS-1:HIV-1 vpr

The HIV-1 Vpr sequence was amplified by PCR from the cDNA inserted in pGEX-2T (GE Healthcare) with the forward primer VPRNotI+link5': 5'-TTCCGCGTGCGGCCG-CATCfTTCCTCATCGGGTAGTAGCTCT-TCCGGCATGGACAAG CCCCAGAAGACCA-3', SEQ ID NO: 7, which appends a restriction site for the endonuclease NotI followed by a (SSSSG)$_2$ (SEQ ID NO:19) linker at the 5' terminus of Vpr sequence, and the reverse primer VPRNotI3': 5'-ATTCCCGGGGCGGCCGCGGATCTACTGGCTCC ATTT-3', SEQ ID NO: 8, which introduces a restriction site for the endonuclease NotI at the 3' terminus of Vpr. The amplified sequence was inserted in the pET22b vector at the C-terminus of the scFvDIATHIS-1 anti-CEA. The assembled construct was transferred into *E. coli* BL21(DE3) for protein expression.

scFv DIATHIS-1:Yeast Cytosine Deaminase (YCD)

The yeast cytosine deaminase (YCD) sequence including the (SSSSG)$_3$ (SEQ ID NO:20) linker at the 5'-terminus, was amplified by PCR from the scFvE8:YCD construct (Zamboni et al., 2008; Int. J. Oncol.) inserted in the pQE30Xa with the forward primer Lin YCD NotI5':5'-CTAGGCGCGGC-CGCTTCCCATICGGGT-3', SEQ ID NO: 9, and with the reverse primer YCD NotI3': 5'-GGCTGCGCGGCCGCCT-CAGGAATATCT-3'. SEQ ID NO: 10, which introduce a restriction site for the endonuclease NotI at both termini. The amplified sequence was inserted in the pET22b(+) vector at the C-terminus of the scFvDIATHIS-1 anti-CEA. The assembled construct was transferred into *E. coli* BL21(DE3) for protein expression.

scFv DIATHIS-1:Listeriolysin-O (LLO) Δ PEST

The listeriolysin-O (LLO) sequence, depleted of the PEST degradation signal, was amplified by PCR from the cDNA inserted in pET3d vector with the forward primer LLONotI+link5':5'-TGACCGTCCTAGGCTCTTCCTCATCGGG-TAGTAGCTCTTCCGGCTCATCGTCCAGCG GCTC-CATGGAAATCG-3'. SEQ ID NO: 11, which appends a restriction site for the endonuclease NotI followed by a (SSSSG)$_3$ (SEQ ID NO:20) linker at the 5' terminus of LLO sequence and with the reverse primer LLONotI3': 5'-ATC-GAAGCGGCCGCAGCTAGCATGACTGGTG-3', SEQ ID NO: 12, which introduces a restriction site for the endonuclease NotI at the 3' terminus of LLO. The amplified sequence was inserted in the pET22b(+) vector at the C-terminus of the scFvDIATHIS-1 anti-CEA. The assembled construct was transferred into *E. coli* BL21(DE3) for protein expression.

scFv DIATHIS-1:Interleukin 2 (IL-2)

The interleukin-2 (IL-2) sequence including the (SSSSG)$_3$ (SEQ ID NO:20) linker at the 5'-terminus, was amplified by PCR from the scFvE8:IL-2 construct inserted in the eukaryotic pcDNA3.1 vector with the forward primer Lin-IL2 Not 5': 5'-CTGACCGCGGCCGCCTCTTCCT-CATCGGGTAGTAG-3', SEQ ID NO: 13, and with the reverse primer IL2-NotI 3': 5'-AGACTCGGCGGCCG-CAGTCAGTGTTGAGATGAT-3', SEQ ID NO: 14, which introduce a restriction site for the endonuclease NotI at both termini. The amplified sequence was inserted in the pET22b (+) vector at the C-terminus of the scFvDIATHIS-1 anti-CEA. The assembled construct was transferred into *E. coli* BL21(DE3) for protein expression.

CEA Binding Activity of Selected Fusion Proteins

Figure 14:
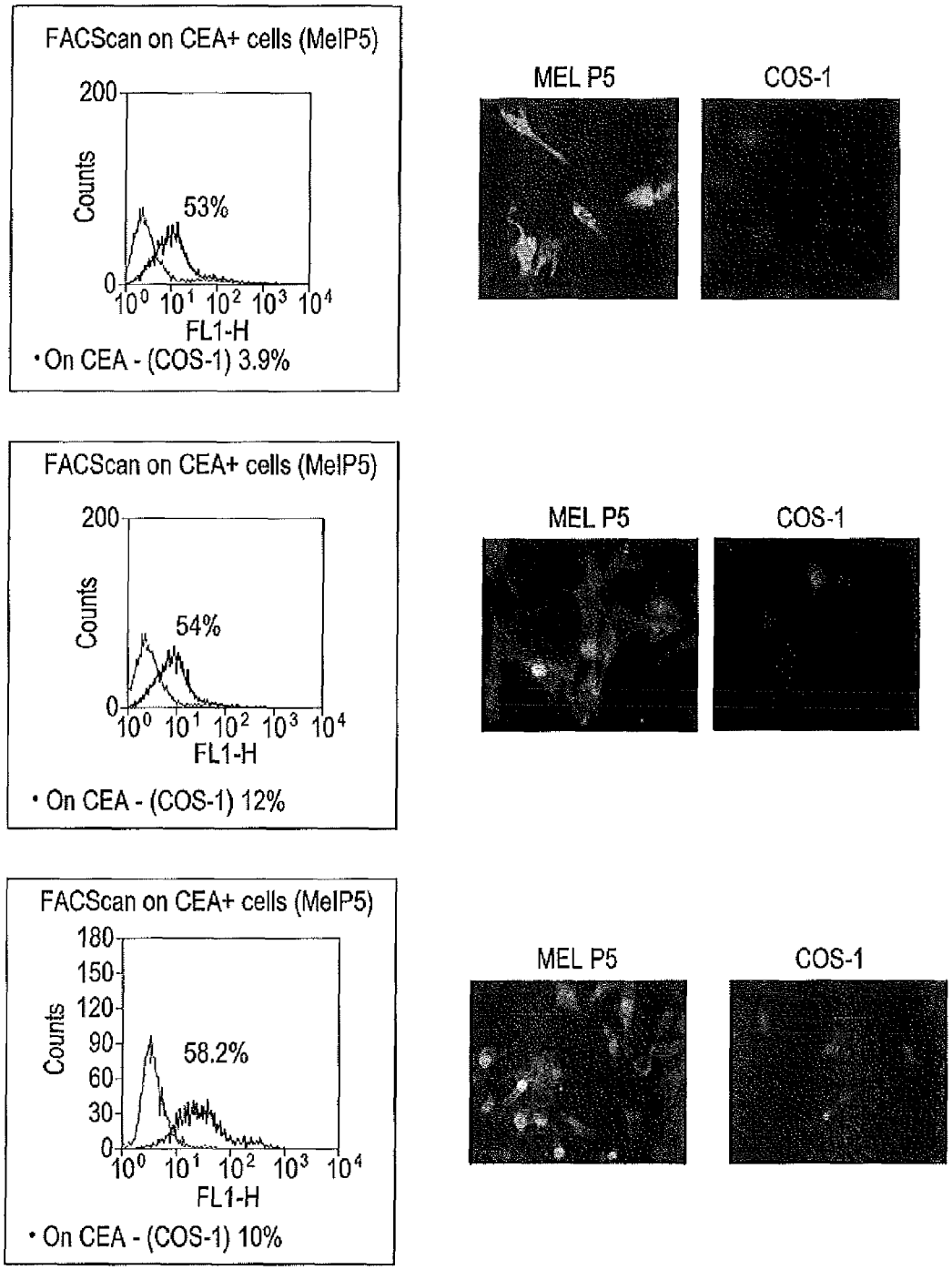
FIG. 14 shows the affinity and specificity of scFv DIATHIS-1 derivatives for CEA antigen, determined by flow cytometry (left panel) and immunofluorescence analysis (right panel) on CEA-positive primary melanoma cell line MelP5.

Accompanying FIG. 14 shows the affinity and specificity of scFv DIATHIS-1 derivatives for CEA antigen, determined by flow cytometry (left panel) and immunofluorescence analysis (right panel) on CEA-positive primary melanoma cell line MelP5. We used COS1 cell line as CEA negative control. (A) Data obtained with scFvDIATHIS-1:ubiquitin fusion protein. (B) Data obtained with scFvDIATHIS-1:HIV-1 vpr fusion protein. (C) Data obtained with scFvDIATHIS-1:YCD fusion protein.

REFERENCES

1. Pavoni E, Flego M, Dupuis M L, Barca S, Petronzelli F, Anastasi A M, D'Alessio V, Pelliccia A, Vaccaro P. Monteriu G, Ascione A, De Santis R, Felici F, Cianfriglia M, Minenkova O. Selection, affinity maturation, and characterization of a human ScFv antibody against CEA protein. *BMC Cancer.* 2006 24; 6:41.
2. Alexander A. Kortt, Olan Dolezal, Narbara E. Power and Feted. Hudson "Diemeric and trimeric antibodies: high avidity scFvs for cancer targeting. *Biomolecular Engineering* 2001 18:95-108
3. Roland Srtork, Kirstin A. Zettlitz, Duffle Muller, Miriam Rether, Franz-Georg Haniseh, and Roland E. Kontermann, N-Glycosylation as Novel Strategy to improve pharmacokinetic Properties of Bispecific Single-Chain Diabodies, *the journal of biological chemistry* 2008; 283:7804-7812.
4. Carter P J. Potent antibody therapeutics by design. *Nat Rev Immunol.* 2006; 6(5):343-57.
5. Sharkey R M and Goldenberg D M. Targeted therapy of cancer: new prospects for antibodies and immunoconjugates. *CA Cancer J Clin.* 2006; 56(4):226-43.
6. Skerra A, Pluckthun A. Assembly of a functional immunoglobulin Fv fragment in *Escherichia coli.* *Science* 1988; 240: 1038-1041.
7. Milenic D E, Yokota T, Filpula D R, Finkelman M A, Dodd S W, Wood J F, Whitlow M, Snoy P, Schlom J. Construction, binding properties, metabolism, and tumor targeting of a single-chain Fv derived from the pancarcinoma monoclonal antibody CC49. *Cancer Res.* 1991; 51:6363-71.
8. Yokota T, Milenic D E, Whitlow M, Schlom J. Rapid tumor penetration of a single-chain Fv and comparison with other immunoglobulin forms. *Cancer Res.* 1992; 52(12):3402-8.
9. Adams G P, McCartney J E, Tai M S, Oppermann H, Huston J S, Stafford W F 3rd, Bookman M A, F and I, Houston L L, Weiner L M. Highly specific in vivo tumor targeting by monovalent and divalent forms of 741F8 anti-c-erbB-2 single-chain Fv. *Cancer Res.* 1993; 53(17):4026-34
10. George A J, Titus J A, Jost C R, Kurucz I, Perez P, Andrew S M, Nicholls P J, Huston J S, Segal D M. Redirection of cellular cytotoxicity. A two-step approach using recombinant single-chain Fv molecules, *Cell Biophys.* 1995; 26(3): 153-65.
11. Albrecht H, Burke P A, Natarajan A, Xiong C Y, Kalicinsky M, DeNardo G L, DeNardo S J. Production of soluble ScFvs with C-terminal-free thiol for site-specific conjugation or stable dimeric ScFvs on demand. *Bioconjug Chem.* 2004; 15(1):16-26.
12. Kim S j, Park Y, and Hong H J. Antibody Engineering for the Development of Therapeutic Antibodies. *Mol. Cells,* 2005; 20:17-29
13. Holliger P, Prospero T, Winter G "Diabodies": small bivalent and bispecific antibody fragments. *Proc Natl Acad Sci USA,* 1993; 90:6444-8.
14. Hu S, Shively L, Raubitschek A, Sherman M, Williams L E, Wong J Y, Shively J E, Wu A M. Minibody: A novel engineered anti-carcinoembryonic antigen antibody fragment (single-chain Fv-CH3) which exhibits rapid, high-level targeting of xenografts. *Cancer Res.* 1996; 56:3055-61.
15. Nolan, O. And O'Kennedy R. Bifunctional antibodies: concept, production and applications. *Biochim. Biophys. Acta.* 1990; 1040:1.

16. Hammarstrom S, The carcinoembryonic antigen (CEA) family: structures, suggested functions and expression in normal and malignant tissues. *Semin Cancer Biol.* 1999; 9:67-81.
17. Thies A, Schachner M, Moll I, Berger J, Schulze H J, Brunner G, Schumacher U. Overexpression of the cell adhesion molecule L1 is associated with metastasis in cutaneous malignant melanoma, *Eur J Cancer.* 2002; 38:1708-16.
18. Oliveira-Ferrer L, Tilki D, Ziegeler G, Hauschild J, Loges S. Irmak S, E, Huiland H, Friedrich M, Ergün S. Dual role of carcinoembryonic antigen-related cell adhesion molecule 1 in angiogenesis and invasion of human urinary bladder cancer. *Cancer Res.* 2004 15; 64:8932-8.
19. Laack E, Nikbakht H, Peters A, Kugler C, Jasiewicz Y, Edler L, Brümmer J, Schumacher U, Hossfeld D K. Expression of CEACAM1 adenocarcinoma of the lung: a factor of independent prognostic significance, *J Clin Oncol.* 2002; 20:4279-84.
20. Mirick G R, Bradt B M, Denardo S J, Denardo G L. A review of human anti-globulin antibody (HAGA, HAMA, HACA, HAHA) responses to monoclonal antibodies. Not four letter words. *Q J Nucl Med Mol Imaging.* 2004; 48(4): 251-7.
21. Hoogenboom H R, Selecting and screening recombinant antibody libraries. *Nat Biotechnol.* 2005; 23(9);1105-16.
22. Benhar I. Design of synthetic antibody libraries. *Expert Opin Biol Ther.* 2007; 7(5):763-79.
23. Graumarm K and Premstaller A, Manufacturing of recombinant therapeutic proteins in microbial systems. *Biotechnol J.* 2006; 1(23:164-86.
24. Holliger P, Hudson P J. Engineered antibody fragments and the rise of sing domains. *Nat Biotechnol.* 2005; 23: 1126-1136.
25. Viti F, Nilsson F, Demartis S, Huber A, Neri D. Design and use of phage display libraries for the selection of antibodies and enzymes, *Methods Enzymol* 2000, 326: 480-505.
26. Nor D, Petrul H, Winter G, Light Y, Marais R, Britton K E, Creighton A M. Radioactive labeling of recombinant antibody fragments by phosphorylation using human casein kinase II and [gamma-32P]-ATP. *Nat Biotechnol.* 1996; 14(4):485-90.
27. Better, M., Chang, C. P., Robinson, R. R., and Horwitz, A. H. (1988) *Escherichia coli* secretion of an active chimeric antibody fragment. *Science* 240, 1041-1043
28. Paetzel M, Karla A, Strynadka N C, Dalbey R E, Signal peptidases. *Chem Rev* 2002; 102:4549-4580.
29. Sletta H, Tøndervik A, Hakvåg S, Aune T E, Nedal A, Anne R, Evensen G, Valla S, Ellingsen T E, Brautaset T. The presence of N-terminal secretion signal sequences loads to strong stimulation of the total expression levels of three tested medically important proteins during high-cell-density cultivations of *Escherichia coli. Appl Environ Microbiol.* 2007; 73(3):906-12.
30. Goto, Y. and Hamaguchi, K. The role of the intrachain disulfide bond in the conformation and stability of the constant fragment of the immunoglobulin light chain. *J. Biochem,* 1979; 86, 1433:1441.
31. Rudikoff, S. and Pumphrey, J. G. Functional antibody lacking a variable-region disulfide bridge. *Proc. Natl Acad. Sci. USA,* 1986; 83, 7875±7878.
32. Proba, K., Honegger, A. & PluÉ ckthun, A. A natural antibody missing a cysteine VH: consequences for thermodynamic stability and folding. *J. Mol. Biol.* 1997; 265, 161±172.
33. Choi J H, Keum K C and Lee S Y, Production of recombinant proteins by high cell density culture of *Escherichia coli. Chem Eng Science* 2006; 61:876-885.
34. S. Rath, C. M. Stanley and M. W. Steward, An inhibition enzyme immunoassay for estimating relative antibody affinity and affinity heterogeneity. *J Immunol Methods.* 1988 10; 106(2):245-9.
35. S I Rudnick and Adams G P. Affinity and avidity in Antibody-Based Tumor Targeting. *Cancer Biother Radiopharm.* 2009; 24(2):155-61.
36. Adams G P, Schier R, McCall A M, Crawford R S, Wolf E J, Weiner L M, Marks J D. Prolonged in vivo tumor retention of a human diabody targeting the extracellular domain of humanHER2/neu. *Br j. Cancer* 1998; 77:1405
37. Verel I, Heider K E, Siegmund M, Ostermann E, Patzeit E, Sproll M, Snow G B, Adolf G R, van Dongen G A. Tumor targeting of antibodies with different affinity for target antigen CD44V6 in nude mice bearing head and neck cancer xenograft. *Int J Cancer* 2002; 99:396-402.
38. Wu A M, Chen W, Raubitschek A, Williams L E, Neumaier M, Fischer R, Hu S Z, Odom-Maryon T, Wong J Y, Shively J R Tumor localization of anti-CEA single-chain Fvs:improved targeting by non-covalent dimers. *Immunotechnology* 1996; 2:21-36
39. Yazaki, P. J Wu, A. M., Tsai, S. W., Williams, L. E., Ikler, L. E., Wong, J. Y., Shively, J. E. and Raubitsehek, A. A. Tumor targeting of radiometal labeled anti-CEA recombinant T84.66 diabody and t84.66 minibody: comparison to radioiodinated fragments. *Bioconjug. Chem.,* 2001; 12, 220-228
40. Muller D, Katie A, Meißburger B, Ho I, Stork R, and Konteman R E. Improved harmacokineties of Recombinant Bispecific Antibody Molecules by Fusion to Human Serum Albumin. *J biological chemistry* 2007; 282: 12650-42660
41. Wu A M, Williams L E, et al, Anti-carcinoembryonic antigen (CEA) diabody for rapid tumor targeting and imaging. *Tumor Targeting* 1999; 4:47-58
42. Olafsen T, Cheung C W, Yazaki P J, Li L, Sundaresan G, Gambhir S S, Sherman M A, Williams L E, Shively J E, Raubitschek A A, Wu A M. Covalent disulfide-linked anti-CEA diabody allows site-specific conjugation and radiolabeling for tumor targeting applications. *Protein Eng Des Sel.* 2004 January; 17(1):21-7.
43. Sundaresan G, Yazaki P J., Shively E., Finn R D, Larson S M, Raubitschek A A., Williams L E, Chatzlioannou A F, Gambhir S S, and Wu A M, 124I-Labeled Engineered Anti-CEA Minibodies and Diabodies Allow High-Contrast, Antigen-Specific Small-Animal PET Imaging Xenografts Athymic Mice. *J Nucl Med* 2003; 44:1962-1969

The invention claimed is:

1. A fusion protein comprising:
    a single chain variable fragment (scFv) specific for both carcinoembryonic antigen (CEA) and CEA related Cell Adhesion Molecule 1 (CEACAM1), and
    a leader sequence, said leader sequence comprising all, or substantially all, of the *E. coli* Pel B leader sequence,
    a linker sequence being optionally present between said leader sequence and said scFv,
    wherein:
        the $V_H$ and the $V_L$ portion of the scFv are as shown in SEQ ID NO: 2,
        the $V_H$ and the $V_L$ portion of the scFv are as shown in SEQ ID NO: 2 with the Pro at position 200 mutated to Leu,
        the $V_H$ and the $V_L$ portion of the scFv are as shown in SEQ ID NO: 2 with the Pro at position 200 of SEQ ID NO: 2 mutated to Leu and the Cys at position 242 of SEQ ID NO: 2 mutated to Trp,
        the $V_H$ and the $V_L$ portion of the scFv are as shown in SEQ ID NO: 2 with the Trp at position 208 of SEQ ID NO: 2 mutated to Arg,
        the $V_H$ and the $V_L$ portion of the scFv are as shown in SEQ ID NO: 2 with the Trp at position 208 of SEQ ID NO: 2 mutated to Arg and the Cys at position 242 of SEQ ID NO: 2 mutated to Trp, or
        the $V_H$ and the $V_L$ portion of the scFv are as shown in SEQ ID NO: 2 with the Cys at position 242 of SEQ ID NO: 2 mutated to Trp.

2. The fusion protein of claim 1, wherein the $V_H$ and the $V_L$ portion of the scFv are as shown in SEQ ID NO: 2 with the Cys at position 242 of SEQ ID NO: 2 mutated to Trp.

3. The fusion protein of claim 1, wherein the $V_H$ and the $V_L$ portion of the scFv are as shown in SEQ ID NO: 2 with the Pro at position 200 mutated to Leu.

4. The fusion protein of claim 1, wherein the $V_H$ and the $V_L$ portion of the scFv are as shown in SEQ ID NO: 2 with the Trp at position 208 of SEQ ID NO: 2 mutated to Arg.

5. The fusion protein of claim 1, wherein the scFv portion comprises the amino acid sequence of the VH and VL portion of SEQ ID NO: 2.

6. The fusion protein of claim 1, comprising the amino acid sequence of SEQ ID NO:2.

7. The fusion protein of claim 1, wherein the functionality of the leader sequence, which allows the protein to be secreted across the cell membrane and the leader sequence cleaved therefrom, is retained.

8. The fusion protein of claim 1, further comprising a tag.

9. The fusion protein of claim 8, wherein the tag comprises any one or more of the components D3SD3, FLAG and His6 (SEQ ID NO:16).

10. The fusion protein of claim 1, which is radiolabeled.

11. The fusion protein of claim 1, further comprising an effector.

12. The fusion protein of claim 11, wherein a linker sequence is optionally present between said scFv and said effector, and wherein said effector is downstream of said scFv.

13. The fusion protein of claim 11, wherein the effector is HIV-1 Vpr; LLOΔPEST; Yeast Cytosine Deaminase (YCD); ubiquitin; or IL-2.

14. A process for the preparation of a fusion protein as defined in claim 1, from a bacterial host cell cultured to express the fusion protein as inclusion bodies, comprising
    (a) applying supernatant containing the inclusion bodies to a chromatographic column loaded with DEAE fast flow resin, and eluted with salt buffer to refold the fusion protein;
    (b) subjecting the eluent to IMAC chromatography and eluting with a salt buffer and diluting the eluent with a non-salt buffer; and
    (c) loading the diluted eluent onto a Sepharose fast flow resin in a column, and eluting with a salt buffer
    thereby recovering the fusion protein from the inclusion bodies.

15. The process according to claim 14, wherein the final salt buffer is at about 0.2 M.

16. The process according to claim 14, wherein the final salt buffer is at about 0.5 M.

17. The process according to claim 14, wherein the final salt buffer is at about 0.2 M followed by about 0.5 M.

18. The fusion protein of claim 1, wherein said scFv consists of a $V_H$ chain, a $V_L$ chain, and a linker, said linker connecting said $V_H$ and $V_L$ chains.

19. The fusion protein of claim 18, wherein said linker is between 5 and 15 amino acid residues in length, inclusive.

20. The fusion protein of claim 18, wherein said linker includes one or more units of GGGGS (SEQ ID NO:15).

21. The fusion protein of claims 18, wherein said linker includes one, two or three units of GGGGS (SEQ ID NO:15).

22. The fusion protein of claim 1, comprising the amino acid sequence of SEQ ID NO:22.

23. The fusion protein of claim 1, comprising the amino acid sequence of SEQ ID NO:24.

24. The fusion protein of claim 1, comprising the amino acid sequence of SEQ ID NO:26.

25. The fusion protein of claim 1, comprising the amino acid sequence of SEQ ID NO:28.

26. The fusion protein of claim 1, comprising the amino acid sequence of SEQ ID NO:30.

* * * * *

UNITED STATES PATENT AND TRADEMARK OFFICE
CERTIFICATE OF CORRECTION

PATENT NO. : 8,822,648 B2  
APPLICATION NO. : 13/725712  
DATED : September 2, 2014  
INVENTOR(S) : Maurizio Cianfriglia et al.

Page 1 of 1

It is certified that error appears in the above-identified patent and that said Letters Patent is hereby corrected as shown below:

On the title page, column 1, line 34 insert

Item -- (30)      Foreign Application Priority Data
     Jun. 21, 2010     (GB) ............................... 1010389.3 --

Signed and Sealed this
Twenty-third Day of December, 2014

Michelle K. Lee
*Deputy Director of the United States Patent and Trademark Office*